United States Patent [19]
MacPherson et al.

[11] Patent Number: 5,646,167
[45] Date of Patent: Jul. 8, 1997

[54] ARYLSULFONAMIDO-SUBSTITUTED HYDROXAMIX ACIDS

[75] Inventors: Lawrence J. MacPherson, Hampton; David T. Parker, Livingston, both of N.J.

[73] Assignee: Ciba-Geigy Corporation, Tarrytown, N.Y.

[21] Appl. No.: 475,166

[22] Filed: Jun. 7, 1995

Related U.S. Application Data

[63] Continuation-in-part of Ser. No. 333,676, Nov. 3, 1994, Pat. No. 5,552,419, which is a continuation-in-part of Ser. No. 265,296, Jun. 24, 1994, Pat. No. 5,506,242, which is a continuation-in-part of Ser. No. 1,136, Jan. 6, 1993, Pat. No. 5,455,258.

[51] Int. Cl.$^6$ ................. A61K 31/44; C07D 213/42
[52] U.S. Cl. ................. 514/357; 546/336; 546/337
[58] Field of Search .................. 546/175, 247, 546/265, 276.4, 336, 337; 548/205, 335.1, 338.1; 544/168; 549/13, 65, 426; 564/84, 92, 94, 90; 514/237.8, 311, 331, 332, 341, 357, 365, 396, 445, 602, 604, 406, 432, 451

[56] References Cited

U.S. PATENT DOCUMENTS

| | | | |
|---|---|---|---|
| 4,743,587 | 5/1988 | Dickens et al. | 514/575 |
| 4,885,027 | 12/1989 | Pomidor | 71/103 |
| 4,996,358 | 2/1991 | Handa et al. | 562/621 |
| 5,114,953 | 5/1992 | Galardy et al. | 514/323 |
| 5,137,914 | 8/1992 | Ohtani et al. | 514/507 |
| 5,240,958 | 8/1993 | Campion et al. | 514/445 |

FOREIGN PATENT DOCUMENTS

| | | | |
|---|---|---|---|
| 0236872 | 9/1987 | European Pat. Off. | 514/307 |
| 0423943 | 4/1991 | European Pat. Off. | 514/307 |
| 0606046 | 7/1994 | European Pat. Off. | 514/507 |
| 9005719 | 5/1990 | WIPO | 514/507 |
| 91/02716 | 3/1991 | WIPO . | |
| 91/05763 | 5/1991 | WIPO . | |
| 9209566 | 6/1992 | WIPO | 514/507 |
| 9209565 | 6/1992 | WIPO | 514/507 |
| 9213831 | 8/1992 | WIPO | 514/507 |
| 93/02194 | 11/1993 | WIPO . | |
| 9410990 | 5/1994 | WIPO | 514/507 |

OTHER PUBLICATIONS

Tibtech, Jun. 1992, vol. 10, pp. 200–207.
J. M. Ray et al., European Respiratory Journal, 7, 2062–2072, 1994.
Nature, vol. 370, Jul. 1994, pp. 218–220.
Nature, vol. 370, Aug. 1994, pp. 558–561.
Nature, vol. 370, Aug. 1994, pp. 555–557.
BioEssays, vol. 14, No. 7, Jul. 1992, pp. 455–463.
Annual Reports in Medicinal Chemistry, 25, pp. 177–184, 1989.
J. Med Chem., 1989, 32, pp. 145–151.
Synthesis, 1985, pp. 929–931.
Chemical Abstr. 93:81521r, 1978.
Chemical Abstr. 59:3824a (1963).
Microchemical Journal, 40, pp. 226–232 (1989).
Chemical Abstr. 70:88228j, 1985.
Chemical Abstr. 59:3824b, 1963.
Trends Biotechnol, vol. 10, No. 6, 1992, pp. 200–207.
J. Clin Invest., vol. 94, Dec. 1994, pp. 2177–2182.

*Primary Examiner*—Zinna Northington Davis
*Attorney, Agent, or Firm*—Norbert Gruenfeld

[57] ABSTRACT

Disclosed are compounds of formula I

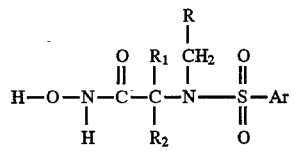

(I)

wherein R, $R_1$, $R_2$ and Ar have meanings as defined; pharmaceutically acceptable prodrug derivatives and pharmaceutically acceptable salts thereof; methods for preparation thereof; pharmaceutical compositions comprising said compounds; and methods of inhibiting matrix-degrading metalloproteinase and of treating matrix-degrading metalloproteinase dependent conditions in mammals using such compounds.

16 Claims, No Drawings

ARYLSULFONAMIDO-SUBSTITUTED HYDROXAMIX ACIDS

CROSS REFERENCE TO RELATED APPLICATIONS

This application is a continuation-in-part of application Ser. No. 08/333,676 filed Nov. 3, 1994, now U.S. Pat. No. 5,552,419, which is a continuation-in-part application of application Ser. No. 08/265,296 filed Jun. 24, 1994, now U.S. Pat. No. 5,506,242 which is a continuation-in-part application of application Ser. No. 08/001,136 filed Jan. 6, 1993, now U.S. Pat. No. 5,455,258.

SUMMARY OF THE INVENTION

The present invention relates to novel arylsulfonamido-substituted hydroxamic acids, as matrix metalloproteinase inhibitors, methods for preparation thereof, pharmaceutical compositions comprising said compounds, a method of inhibiting matrix-degrading metalloproteinases and a method of treating matrix metalloproteinase dependent diseases or conditions in mammals which are responsive to matrix metalloprotease inhibition, using such compounds or pharmaceutical compositions comprising such compounds of the invention.

Matrix-degrading metalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor growth, tumor metastasis, tumor progression or invasion, tumor angiogenesis, as well as HIV-infection (as reported in J. Leuk. Biol. 52 (2): 244–248, 1992), atherosclerosis and restenosis in angioplasty.

Macrophage metalloelastase is a further matrix-degrading metalloproteinase which is involved in the degradation of elastin and has been implicated in pathological conditions, e.g. pulmonary disorders such as emphysema.

The compounds of the invention are inhibitors of stromelysin, gelatinase and/or collagenase activity, inhibit matrix degradation and are useful for the treatment of gelatinase, stromelysin and collagenase dependent pathological conditions in mammals, such as those cited above, including rheumatoid arthritis, osteoanhritis, tumor growth, tumor metastasis, tumor progression or invasion, tumor angiogenesis, periodontal disease, as well as the progression of HIV-infection and associated disorders, atherosclerosis, osteoporosis, and restenosis associated with angioplasty. Relevant tumors include human breast, lung, bladder, colon, ovarian and skin cancer.

The compounds of the invention are also inhibitors of macrophage elastase, inhibit elastin degradation and are useful for the treatment of bronchial disorders, such as emphysema.

Ocular applications of the compounds of the invention include the treatment of corneal ulcerations, pterygium, keratitis, keratoconus, open angle glaucoma, retinopathies, and also their use in conjunction with refractive surgery (laser or incisional) to minimize adverse effects.

Certain metalloproteinase inhibitors have been reported to also inhibit the production and release of tumor necrosis factors (TNF) e.g. TNF-α which is an important mediator of inflammation. Thus, compounds of the invention are potential anti-inflammatory agents in mammals.

Matrix-degrading metalloproteinases are involved in plaque rupture (destabilization of plaques), which is a contributing factor to acute coronary syndrome, heart attacks and strokes occurring under atherosclerotic conditions in mammals. Thus, compounds of the invention should stabilize atherosclerotic plaques (inhibit their rupture) and be useful for the treatment of atherosclerotic conditions, such as acute coronary syndrome, heart attacks (cardiac ischemia) and strokes (cerebral ischemia).

Furthermore, matrix metalloproteinases are involved in post-angioplasty and post-atherectomy vascular remodeling and the compounds of the invention should be useful for the treatment or prevention thereof.

In addition, matrix metalloproteinases have been implicated in inflammatory demyelinating disorders of the nervous system in which myelin destruction or loss is involved, such as multiple sclerosis, optic neuritis, neuromyelitis optica (Devic's disease), diffuse and transitional sclerosis (Schilder's disease) and acute disseminated encephalomyelitis, also demyelinating peripheral neuropathies such as Landry-Guillain-Barre-Strohl syndrome for motor defects. Thus, the compounds of the invention should also be useful for the treatment of such demyelinating diseases in mammals.

DETAILED DESCRIPTION OF THE INVENTION

The present invention relates to the compounds of formula I

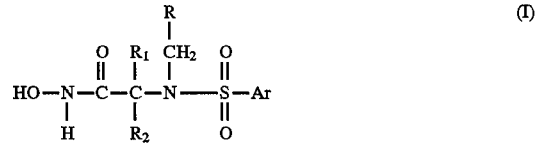

(a) wherein

Ar is carbocyclic or heterocyclic aryl;

R is hydrogen, lower alkyl, carbocyclic aryl-lower alkyl, carbocyclic aryl, heterocyclic aryl, biaryl, biaryl-lower alkyl, heterocyclic aryl-lower alkyl, mono- or poly-halo-lower alkyl, $C_3$–$C_7$-cycloalkyl, $C_3$–$C_7$-cycloalkyl-lower alkyl, (oxa or thia)-$C_3$–$C_6$-cycloalkyl, [(oxa or thia)-$C_3$–$C_6$-cycloalkyl]-lower alkyl, hydroxy-lower alkyl, acyloxy-lower alkyl, lower alkoxy-lower alkyl, lower alkyl-(thio, sulfinyl or sulfonyl)-lower alkyl, (amino, mono- or di-lower alkylamino)-lower alkyl, acylamino-lower alkyl, (N-lower alkyl-piperazino or N-carbocyclic or heterocyclic aryl-lower alkylpiperazino)-lower alkyl, or (morpholino, thiomorpholino, piperidino, pyrrolidino, piperidyl or N-lower alkylpiperidyl)-lower alkyl;

$R_1$ is hydrogen, lower alkyl, carbocyclic aryl-lower alkyl, carbocyclic aryl, heterocyclic aryl, biaryl, biaryl-lower alkyl, heterocyclic aryl-lower alkyl, mono- or poly-halo-lower alkyl, $C_3$–$C_{10}$-cycloalkyl, $C_3$–$C_7$-cycloalkyl-lower alkyl, hydroxy-lower alkyl, acyloxy-lower alkyl, lower alkoxy-lower alkyl, (carbocyclic or heterocyclic aryl)-lower alkoxy-lower alkyl, lower alkyl-(thio, sulfinyl or sulfonyl)-lower alkyl, (amino, mono- or di-lower alkylamino)-lower alkyl, (N-lower alkyl-piperazino or N-carbocyclic or heterocyclic aryl-lower alkylpiperazino)-lower alkyl, (morpholino, thiomorpholino, piperidino, pyrrolidino, piperidyl, N-acyl or N-lower alkylpiperidyl)-lower alkyl, acylamino-lower alkyl, piperidyl, (morpholino, thiomorpholino, piperidino, pyrrolidino, piperidyl, N-acyl or N-lower alkylpiperidyl)-(hydroxy or lower alkoxy) lower alkyl, pyrrolidinyl, hexahydroazepinyl, N-lower alkyl or N-acyl(hexahydroazepinyl, piperidyl or pyrrolidinyl), $C_5$–$C_{10}$-oxacycloalkyl, $C_5$–$C_{10}$-thiacycloalkyl, (hydroxy- or oxo-) $C_5$–$C_{10}$-cycloalkyl, (hydroxy- or oxo-) $C_5$–$C_{10}$-thiacycloalkyl, (hydroxy- or oxo-) $C_5$–$C_{10}$-oxacycloalkyl, (amino, mono- or dialkylamino or acylamino)-$C_5$–$C_{10}$-cycloalkyl, 2-oxo(pyrrolidinyl, piperidyl or hexahydroazepinyl), (carbocyclic or heterocyclic aryl)-(thio, sulfinyl or sulfonyl)-lower alkyl;

$R_2$ is hydrogen or lower alkyl;

(b) or wherein R and $R_1$ together with the chain to which they are attached form a 1,2,3,4-tetrahydro-isoquinoline, piperidine, oxazolidine, thiazolidine or pyrrolidine ring, each unsubstituted or substituted by lower alkyl; and Ar and $R_2$ have meaning as defined under (a);

(c) or wherein $R_1$ and $R_2$ together with the carbon atom to which they are attached form a ring system selected from $C_3$–$C_7$-cycloalkane which is unsubstituted or substituted by lower alkyl; oxa-cyclohexane, thia-cyclohexane, indane, tetralin, piperidine or piperidine substituted on nitrogen by acyl, lower alkyl, carbocyclic or heterocyclic aryl-lower alkyl, (carboxy, esterified or amidated carboxy)-lower alkyl or by lower alkylsulfonyl; and Ar and R have meaning as defined under (a);

pharmaceutically acceptable prodrug derivatives thereof; and pharmaceutically acceptable salts thereof;

further to a process for the preparation of these compounds, to pharmaceutical compositions comprising these compounds, to the use of these compounds for the therapeutic treatment of the human or animal body or for the manufacture of a pharmaceutical composition.

The compounds of formula I defined under (b) above can be represented by formula Ia

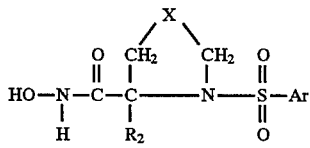

wherein X represents methylene or 1,2-ethylene each unsubstituted or substituted by lower alkyl, or X represents oxygen, sulfur, or 1,2-phenylene; and Ar and $R_2$ have meaning as defined above.

The compounds of formula I defined under (c) above can be represented by formula Ib

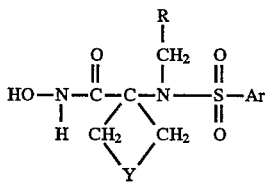

wherein Y is a direct bond, $C_1$–$C_4$-straight chain alkylene optionally substituted by lower alkyl, $CH_2OCH_2$, $CH_2SCH_2$, 1,2-phenylene, $CH_2$-1,2-phenylene or $CH_2N(R_6)$-$CH_2$ in which $R_6$ represents hydrogen, lower alkanoyl, di-lower alkylamino-lower alkanoyl, aroyl, carbocyclic aryl-lower alkanoyl, lower alkyl, carbocyclic or heterocylic aryl-lower alkyl, (carboxy, esterified or amidated carboxy)-lower alkyl or lower alkylsulfonyl; and Ar and R have meaning as defined above.

A preferred embodiment of the compounds of formula Ib relates to the compounds of formula Ic

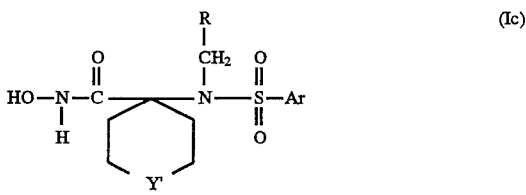

in which Y' represents oxygen, sulfur, a direct bond, methylene or methylene substituted by lower alkyl, or $NR_6$; $R_6$ represents hydrogen, lower alkanoyl, di-lower alkylamino-lower alkanoyl, carbocyclic aryl-lower alkanoyl, lower alkyl, carbocyclic or heterocyclic aryl-lower alkyl, (carboxy, esterified or amidated carboxy)-lower alkyl or lower alkylsulfonyl; Ar and R have meaning as defined above; pharmaceutically acceptable prodrug derivatives; and pharmaceutically acceptable salts thereof.

Preferred are said compounds of formula I, Ia, Ib and Ic wherein Ar is monocyclic carbocyclic aryl such as phenyl or phenyl mono-, di- or tri-substituted by $C_1$–$C_{10}$-alkoxy, hydroxy, carbocyclic or heterocyclic aryl-lower alkoxy, $C_3$–$C_7$-cycloalkyl-lower alkoxy, (lower alkyl, carbocyclic or heterocyclic aryl-lower alkyl or $C_3$–$C_7$-cycloalkyl-lower alkyl)-thio, lower alkyloxy-lower alkoxy, halogen, lower alkyl, cyano, nitro, trifluoromethyl, lower alkyl-(sulfinyl or sulfonyl), amino or mono- or di-lower alkylamino; or Ar is phenyl substituted on adjacent carbon atoms by $C_1$–$C_2$-alkylenedioxy or oxy-$C_2$–$C_3$-alkylene; or Ar is heterocyclic monocyclic aryl such as thienyl or thienyl substituted by lower alkyl; the other symbols have meaning as defined; pharmaceutically acceptable prodrug derivatives thereof; and pharmaceutically acceptable salts thereof.

Further preferred are the compounds of formula I (a) wherein Ar is phenyl which is unsubstituted or mono-, di- or tri-substituted by $C_1$–$C_{10}$-alkoxy, hydroxy; phenyl-lower alkoxy wherein phenyl is unsubstituted or substituted by lower alkyl, lower alkoxy, halogen or trifluoromethyl; heterocyclic aryl-lower alkoxy wherein heterocyclic aryl is selected from pyridyl, tetrazolyl, triazolyl, thiazolyl, thienyl, imidazolyl and quinolinyl, each unsubstituted or mono- or di-substituted by lower alkyl or halogen; or Ar is phenyl substituted by $C_3$–$C_7$-cycloalkyl-lower alkoxy, (lower alkyl, phenyl-lower alkyl or $C_3$–$C_7$-cycloalkyl-lower alkyl)-thio, lower alkyloxy-lower alkoxy, halogen, lower alkyl, cyano, nitro, trifluoromethyl, lower alkyl-(sulfinyl or sulfonyl), amino, mono- or di-lower alkylamino; or Ar is phenyl substituted on adjacent carbon atoms, by $C_1$–$C_2$-alkylenedioxy or oxy-$C_2$–$C_3$-alkylene; or Ar is thienyl, isoxazolyl or thiazolyl each of which is unsubstituted or mono- or di-substituted by lower alkyl;

R is hydrogen, lower alkyl, phenyl-lower alkyl wherein phenyl is unsubstituted or substituted by lower alkyl, lower alkoxy, halogen or trifluoromethyl; phenyl which is unsubstituted or mono-, di- or tri-substituted by lower alkoxy, hydroxy, halogen, lower alkyl, cyano, nitro, trifluoromethyl, lower alkyl-(thio, sulfinyl or sulfonyl), amino, mono- or di-lower alkylamino or, on adjacent carbon atoms, by $C_1$–$C_2$-alkylenedioxy or oxy-$C_2$–$C_3$-alkylene; or a heterocyclic aryl radical selected from pyridyl, tetrazolyl, triazolyl, thiazolyl, thienyl, imidazolyl and quinolinyl, each unsubstituted or mono- or di-substituted by lower alkyl or halogen; biphenylyl which is unsubstituted or substituted by lower alkyl, lower alkoxy, halogen, trifluoromethyl or cyano; biphenylyl-lower alkyl wherein biphenylyl is unsubstituted or substituted by lower alkyl, lower alkoxy, halogen, trifluoromethyl or cyano; (pyridyl, thienyl, quinolinyl or thiazolyl)-lower alkyl, trifluoromethyl, $C_3$–$C_7$-cycloalkyl, $C_3$–$C_7$-cycloalkyl-lower alkyl, (oxa or thia)-$C_3$–$C_6$-cycloalkyl, [(oxa or thia)-$C_3$–$C_6$-cycloalkyl]-lower alkyl, hydroxy-lower alkyl, lower alkanoyloxy-lower alkyl, lower alkoxy-lower alkyl, lower alkyl-(thio, sulfinyl or sulfonyl)-lower alkyl, (amino, mono- or di-lower alkylamino)-lower alkyl, lower alkanoylamino-lower alkyl, (N-lower alkyl-piperazino or N-phenyl-lower alkylpiperazino)-lower alkyl or (morpholino, thiomorpholino, piperidino, pyrrolidino, piperidyl or N-lower alkylpiperidyl)-lower alkyl;

$R_1$ is hydrogen; lower alkyl; phenyl-lower alkyl wherein phenyl is unsubstituted or substituted by lower alkyl, lower alkoxy, halogen, trifluoromethyl or, on adjacent carbon atoms, by $C_1$–$C_2$-alkylenedioxy or oxy-$C_2$–$C_3$-alkylene; phenyl which is unsubstituted or substituted by lower alkyl, lower alkoxy, halogen or trifluoromethyl; pyridyl; thienyl, biphenylyl; biphenylyl-lower alkyl; heterocyclic aryl-lower alkyl wherein heterocyclic aryl is selected from thiazolyl, pyrazolyl, pyridyl, imidazolyl and tetrazolyl each unsubstituted or substituted by lower alkyl; trifluoromethyl; $C_3$–$C_7$-cycloalkyl, $C_3$–$C_7$-cycloalkyl-lower alkyl; hydroxy-lower alkyl; lower alkanoyloxy-lower alkyl; lower alkoxy-lower alkyl; (phenyl or pyridyl)-lower alkoxy-lower alkyl; lower alkyl-(thio, sulfinyl or sulfonyl)-lower alkyl; (amino, mono- or di-lower alkylamino)-lower alkyl; (N-lower alkyl-piperazino or N-phenyl-lower alkylpiperazino)-lower alkyl; (morpholino, thiomorpholino, piperidino, pyrrolidino, piperidyl or N-lower alkylpiperidyl)-lower alkyl; lower alkanoylamino-lower alkyl; $R_3$-CONH-lower alkyl wherein $R_3$ represents (di-lower alkylamino, N-lower alkylpiperazino, morpholino, thiomorpholino, piperidino, pyrrolidino or N-alkylpiperidyl)-lower alkyl; piperidyl; pyrrolidinyl; hexahydroazepinyl; N-lower alkyl- or N-acyl-(hexahydroazepinyl, piperidyl or pyrrolidinyl); $C_5$–$C_{10}$-oxacycloalkyl; $C_5$–$C_{10}$-thiacycloalkyl; (hydroxy- or oxo-) $C_5$–$C_{10}$-cycloalkyl; (hydroxy- or oxo-) $C_5$–$C_{10}$-thiacycloalkyl; (hydroxy- or oxo-) $C_5$–$C_{10}$-oxacycloalkyl; (amino, mono- or dialkylamino or lower alkanoylamino)-$C_5$–$C_{10}$-cycloalkyl; phenyl-thio-lower alkyl wherein phenyl is unsubstituted or substituted by lower alkyl, lower alkoxy, halogen, trifluoromethyl, or, on adjacent carbon atoms, by $C_1$–$C_2$-alkylenedioxy or oxy-$C_2$–$C_3$-alkylene; heterocyclic aryl-thio-lower alkyl wherein heterocyclic aryl is selected from thiazolyl, pyrazolyl, pyridyl, imidazolyl, thienyl and furanyl, each unsubstituted or substituted by lower alkyl;

$R_2$ is hydrogen or lower alkyl;

(b) or wherein R and $R_1$ together with the chain to which they are attached form a 1,2,3,4-tetrahydro-isoquinoline, piperidine, oxazolidine, thiazolidine or pyrrolidine ring, each unsubstituted or mono- or di-substituted by lower alkyl; and Ar and $R_2$ have meaning as defined under (a);

(c) or wherein $R_1$ and $R_2$ together with the carbon atom to which they are attached form a ring system selected from $C_3$–$C_7$-cycloalkane which is unsubstituted or substituted by lower alkyl; oxa-cyclohexane, thia-cyclohexane, indane, tetratin and piperidine which is unsubstituted or substituted on nitrogen by lower alkanoyl, di-lower alkylamino-lower alkanoyl, lower alkoxycarbonyl, (morpholino, thiomorpholino or piperidino)-carbonyl, lower alkyl, (phenyl or pyridyl)-lower alkyl, (carboxy, lower alkoxycarbonyl, benzyloxycarbonyl, aminocarbonyl or mono- or di-lower alkylaminocarbonyl)-lower alkyl or by lower alkylsulfonyl; and Ar and R have meaning as defined under (a);

a pharmaceutically acceptable prodrug derivative thereof; or a pharmaceutically acceptable salt thereof.

Especially preferred are the compounds of formula I (a) wherein Ar is phenyl which is unsubstituted or mono-, di- or fi-substituted by $C_1$–$C_7$-alkoxy, hydroxy, phenyl-lower alkoxy, $C_3$–$C_7$-cycloalkyl-lower alkoxy, lower alkyloxy-lower alkoxy, halogen, lower alkyl, cyano, nitro, trifluoromethyl, lower alkyl-(sulfinyl or sulfonyl), amino, mono- or di-lower alkylamino or, on adjacent carbon atoms, by $C_1$–$C_2$-alkylenedioxy or oxy-$C_2$–$C_3$-alkylene; or Ar is thienyl, isoxazolyl or thiazolyl each of which is unsubstituted or mono- or di-substituted by lower alkyl;

R is hydrogen; lower alkyl, phenyl-lower alkyl; phenyl which is unsubstituted or mono-, di- or tri-substituted by lower alkoxy, hydroxy, halogen, lower alkyl, trifluoromethyl, or, on adjacent carbon atoms, by $C_1$–$C_2$-alkylenedioxy or oxy-$C_2$–$C_3$-alkylene; a heterocyclic aryl radical selected from pyridyl, thiazolyl and quinolinyl, each unsubstituted or mono- or di-substituted by lower alkyl; biphenylyl; biphenylyl-lower alkyl; (pyridyl or thienyl)-lower alkyl; trifluoromethyl; $C_3$–$C_7$-cycloalkyl, $C_3$–$C_7$-cycloalkyl-lower alkyl, (oxa or thia)-$C_3$–$C_6$-cycloalkyl, [(oxa or thia)-$C_3$–$C_6$-cycloalkyl]-lower alkyl; hydroxy-lower alkyl; (N-lower alkyl-piperazino or N-phenyl-lower alkylpiperazino)-lower alkyl or (morpholino, thiomorpholino, piperidino, pyrrolidino, piperidyl or N-lower alkylpiperidyl)-lower alkyl;

$R_1$ is hydrogen; lower alkyl; phenyl-lower alkyl wherein phenyl is unsubstituted or substituted by lower alkyl, lower alkoxy, halogen, trifluoromethyl or, on adjacent carbon atoms, by $C_1$–$C_2$-alkylenedioxy; biphenylyl-lower alkyl; heterocyclic aryl-lower alkyl wherein heterocyclic aryl is selected from thiazolyl, pyrazolyl, pyridyl, imidazolyl and tetrazolyl each unsubstituted or substituted by lower alkyl; $C_3$–$C_{10}$-cycloalkyl; $C_3$–$C_7$-cycloalkyl-lower alkyl; hydroxy-lower alkyl, (phenyl or pyridyl)-lower alkoxy-lower alkyl; lower alkyl-(thio, sulfinyl or sulfonyl)-lower alkyl; (amino, mono- or di-lower alkylamino)-lower alkyl; (N-lower alkyl-piperazino or N-phenyl-lower alkylpiperazino)-lower alkyl; (morpholino, thiomorpholino, piperidino, pyrrolidino, piperidyl or N-lower alkylpiperidyl)-lower alkyl; lower alkanoylamino-lower alkyl; $R_3$-CONH-lower alkyl wherein $R_3$ represents (di-lower alkylamino, N-lower alkylpiperazino, morpholino, thiomorpholino, piperidino, pyrrolidino or N-alkylpiperidyl)-lower alkyl; piperidyl; pyrrolidinyl; hexahydroazepinyl; N-lower alkyl- or N-acyl-(hexahydroazepinyl, piperidyl or pyrrolidinyl); $C_5$–$C_{10}$-oxacycloalkyl; $C_5$–$C_{10}$-thiacycloalkyl; (hydroxy- or oxo-) $C_5$–$C_{10}$-cycloalkyl; (hydroxy- or oxo-) $C_5$–$C_{10}$-thiacycloalkyl; (hydroxy- or oxo-) oxacycloalkyl; (amino, mono- or dialkylamino or lower alkanoylamino)-$C_5$–$C_{10}$-cycloalkyl; phenyl-thio-lower alkyl wherein phenyl is unsubstituted or substituted by lower alkyl, lower alkoxy, halogen or trifluoromethyl; heterocyclic aryl-thio-lower alkyl wherein heterocyclic aryl is selected from thienyl and furanyl, each unsubstituted or substituted by lower alkyl;

$R_2$ is hydrogen or lower alkyl;

(b) or wherein R and $R_1$ together with the chain to which they are attached form a thiazolidine or pyrrolidine ring, each unsubstituted or mono- or di-substituted by lower alkyl; and Ar and $R_2$ have meaning as defined under (a);

(c) or wherein $R_1$ and $R_2$ together with the carbon atom to which they are attached form a ring system selected from $C_3$–$C_7$-cycloalkane which is unsubstituted or substituted by lower alkyl; oxa-cyclohexane; thia-cyclohexane; and piperidine which is unsubstituted or substituted on nitrogen by lower alkanoyl, di-lower alkylamino-lower alkanoyl, lower alkoxycarbonyl, (morpholino, thiomorpholino or piperidino)-carbonyl, lower alkyl, (phenyl or pyridyl)-lower alkyl, (carboxy, lower alkoxycarbonyl, aminocarbonyl or mono- or di-lower alkylaminocarbonyl)-lower alkyl or by lower alkylsulfonyl; and Ar and R have meaning as defined under (a);

a pharmaceutically acceptable prodrug derivative thereof; or a pharmaceutically acceptable salt thereof.

A particular embodiment of the invention relates to the compounds of formula II

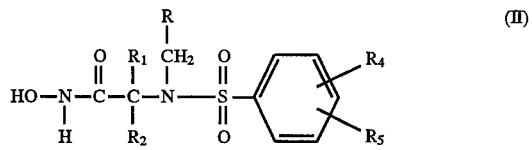

wherein

R is hydrogen, lower alkyl, carbocyclic aryl-lower alkyl, carbocyclic aryl, heterocyclic aryl, biaryl, biaryl-lower alkyl, heterocyclic aryl-lower alkyl, mono- or poly-halo-lower alkyl, $C_3$–$C_7$-cycloalkyl, $C_3$–$C_7$-cycloalkyl-lower alkyl, (oxa or thia)-$C_3$–$C_6$-cycloalkyl, [(oxa or thia)-$C_3$–$C_6$-cycloalkyl]-lower alkyl, hydroxy-lower alkyl, acyloxy-lower alkyl, lower alkoxy-lower alkyl, lower alkyl-(thio, sulfinyl or sulfonyl)-lower alkyl, (amino, mono- or di-lower alkylamino)-lower alkyl, acylamino-lower alkyl, (N-lower alkyl-piperazino or N-carbocyclic or heterocyclic aryl-lower alkylpiperazino)-lower alkyl, or (morpholino, thiomorpholino, piperidino, pyrrolidino or N-lower alkylpiperidyl)-lower alkyl;

$R_1$ is hydrogen, lower alkyl, carbocyclic aryl-lower alkyl, carbocyclic aryl, heterocyclic aryl, biaryl, biaryl-lower alkyl, heterocyclic aryl-lower alkyl, mono- or poly-halo-lower alkyl, $C_5$–$C_8$-cycloalkyl, $C_5$–$C_7$-cycloalkyl-lower alkyl, hydroxy-lower alkyl, acyloxy-lower alkyl, lower alkoxy-lower alkyl, lower alkyl-(thio, sulfinyl or sulfonyl)-lower alkyl, (amino, mono- or di-lower alkylamino)-lower alkyl, (N-lower alkyl-piperazino or N-carbocyclic or heterocyclic aryl-lower alkylpiperazino)-lower alkyl, (morpholino, thiomorpholino, piperidino, pyrrolidino, piperidyl or N-lower alkylpiperidyl)-lower alkyl, piperidyl, N-lower alkylpiperidyl, or acylamino-lower alkyl represented by $R_3$-CONH-lower alkyl, pyrrolidinyl, hexahydroazepinyl or N-lower alkyl (pyrrolidinyl or hexahydroazepinyl), $C_5$–$C_7$-oxacycloalkyl, $C_5$–$C_7$-thiacycloalkyl, hydroxy or oxo-cyclohexyl, (amino, mono- or di-lower alkylamino) cyclohexyl or 2-oxohexahydroazepinyl; phenyl-thio-lower alkyl wherein phenyl is unsubstituted or substituted by lower alkyl; heterocyclic aryl-thio-lower alkyl wherein heterocyclic aryl is selected from thienyl and furanyl, each unsubstituted or substituted by lower alkyl;

$R_2$ is hydrogen;

$R_3$ in $R_3$-CONH-lower alkyl is lower alkyl, carbocyclic or heterocyclic aryl, di-lower alkylamino, N-lower alkylpiperazino, morpholino, thiomorpholino, piperidino, pyrrolidino, N-alkylpiperidyl, or (di-lower alkylamino, N-lower alkylpiperazino, morpholino, thiomorpholino, piperidino, pyrrolidino, pyridyl or N-lower alkylpiperidyl)-lower alkyl;

$R_4$ is hydrogen, lower alkoxy, hydroxy, carbocyclic or heterocyclic aryl-lower alkoxy, lower alkylthio or carbocyclic or heterocyclic aryl-lower alkylthio, lower alkyloxy-lower alkoxy, halogen, trifluoromethyl, lower alkyl, nitro or cyano;

$R_5$ is hydrogen, lower alkyl or halogen;

or $R_4$ and $R_5$ together on adjacent carbon atoms represent methylenedioxy, ethylenedioxy, oxyethylene or oxypropylene;

or a pharmaceutically acceptable prodrug derivative thereof; or a pharmaceutically acceptable salt thereof.

Another preferred embodiment of the invention relates to the compounds of formula II wherein R and $R_1$ together with the chain to which they are attached form an 1,2,3,4-tetrahydro-isoquinoline, piperidine, thiazolidine or pyrrolidine ring; and $R_2$, $R_4$ and $R_5$ have meaning as defined above; pharmaceutically acceptable prodrug derivatives; and pharmaceutically acceptable salts thereof. Such compounds correspond to compounds of formula Ia wherein Ar is optionally substituted phenyl as defined above.

Another preferred embodiment of the invention relates to the compounds of formula II wherein $R_1$ and $R_2$ together with the carbon atom to which they are attached form a ring system selected from cyclohexane, cyclopentane, oxacyclohexane, thiacyclohexane, indane, tetralin, piperidine or piperidine substituted on nitrogen by acyl, lower alkyl, carbocyclic or heterocyclic aryl-lower alkyl or by lower alkylsulfonyl; and R, $R_4$ and $R_5$ have meaning as defined above; pharmaceutically acceptable prodrug derivatives; and pharmaceutically acceptable salts thereof. Such compounds correspond to compounds of formula Ib wherein Ar is optionally substituted phenyl as defined above.

Particularly preferred are the compounds of formula III

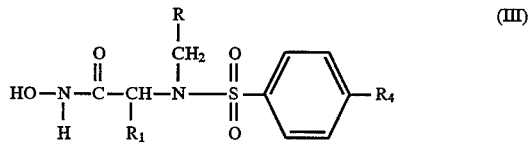

wherein R represents lower alkyl, trifluoromethyl, $C_5$–$C_7$-cycloalkyl, (oxa or thia)-$C_4$–$C_5$-cycloalkyl, biaryl, carbocyclic monocyclic aryl or heterocyclic monocyclic aryl; $R_1$ represents hydrogen, lower alkyl, $C_5$–$C_8$-cycloalkyl, monocyclic carbocyclic aryl, carbocyclic aryl-lower alkyl, heterocyclic aryl-lower alkyl, lower alkoxy-lower alkyl, hydroxy-lower alkyl, lower alkyl-(thio, sulfinyl or sulfonyl) -lower alkyl, di-lower alkylamino-lower alkyl, (N-lower alkylpiperazino, morpholino, thiomorpholino, piperidino or pyrrolidino)-lower alkyl, $C_5$–$C_7$-oxacycloalkyl, (hydroxy, oxo or di-lower alkylamino) cyclohexyl, $R_3$-CONH-lower alkyl, phenyl-thio-lower alkyl wherein phenyl is unsubstituted or substituted by lower alkyl, lower alkoxy, halogen or trifluoromethyl, heterocyclic aryl-thio-lower alkyl wherein heterocyclic aryl is selected from thiazolyl, pyridyl, imidazolyl, thienyl and furanyl, each unsubstituted or substituted by lower alkyl; $R_3$ represents lower alkyl, carbocyclic aryl, heterocyclic aryl, di-lower alkylamino, N-lower alkylpiperazino, morpholino, thiomorpholino, piperidino, pyrrolidino, N-alkylpiperidyl, or (di-lower alkylamino, N-lower alkylpiperazino, morpholino, thiomorpholino, piperidino, pyrrolidino or N-alkylpiperidyl)-lower alkyl; $R_4$ represents lower alkoxy or carbocyclic or heterocyclic aryl-lower alkoxy; or a pharmaceutically acceptable prodrug derivative thereof; or a pharmaceutically acceptable salt thereof.

Further preferred are compounds of formula III wherein R represents monocyclic carbocyclic aryl or monocyclic heterocyclic aryl; $R_1$ and $R_4$ have meaning as defined above; pharmaceutically acceptable prodrug derivatives; and pharmaceutically acceptable salts thereof.

More particularly preferred are said compounds of formula III wherein R represents heterocyclic monocyclic aryl selected from tetrazolyl, triazolyl, thiazolyl, imidazolyl and pyridyl, each unsubstituted or substituted by lower alkyl; or R represents phenyl or phenyl substituted by lower alkyl, lower alkoxy, halogen or trifluoromethyl; $R_1$ represents lower alkyl, cyclohexyl, 2- or 3-tetrahydrofuranyl,(phenyl-, thienyl- or furanyl-)thiomethyl, or $R_3$-CONH-lower alkyl wherein $R_3$ represents (di-lower alkylamino, N-lower alkylpiperazino, morpholino, thiomorpholino, piperidino, pyrrolidino or N-alkylpiperidyl)-lower alkyl; and $R_4$ represents lower alkoxy or phenyl-lower alkoxy; or a pharmaceutically acceptable prodrug derivative thereof; or a pharmaceutically acceptable salt thereof.

A further preferred embodiment relates to said compounds of formula III wherein R represents 2-, 3- or 4-pyridyl or phenyl; $R_1$ represents $C_1$–$C_4$-alkyl, cyclohexyl, 2- or 3-tetrahydrofuranyl, or $R_3$-CONH-$C_1$–$C_4$-alkyl wherein $R_3$ represents di-$C_1$–$C_4$-alkylamino-$C_1$–$C_4$-lower alkyl; and $R_4$ represents lower alkoxy; or a pharmaceutically acceptable prodrug derivative thereof; or a pharmaceutically acceptable salt thereof.

Particularly preferred are said compounds of formula III wherein R represents 3-pyridyl or 4-pyridyl; $R_1$ represents isopropyl, cyclohexyl or 2-tetrahydrofuranyl; and $R_4$ represents lower alkoxy; or a pharmaceutically acceptable prodrug derivative thereof; or a pharmaceutically acceptable salt thereof.

Another embodiment of the invention relates to compounds of Formula III wherein R represents pyridyl, pyridyl substituted by lower alkyl, phenyl, or phenyl substituted by lower alkyl, lower alkoxy, halogen or trifluoromethyl; $R_1$ represents (phenyl-, thienyl- or furanyl-) thio-$C_1$–$C_4$-alkyl; and $R_4$ represents lower alkoxy; or a pharmaceutically acceptable prodrug derivative thereof; or a pharmaceutically acceptable salt thereof.

Further preferred are said compounds of Formula III wherein R represents phenyl or phenyl substituted by lower alkyl, lower alkoxy, halogen or trifluoromethyl; $R_1$ represents (phenyl)-thiomethyl, (2-thienyl)-thiomethyl or (2-furanyl)-thiomethyl; and $R_4$ represents lower alkoxy; or a pharmaceutically acceptable prodrug derivative thereof; or a pharmaceutically acceptable salt thereof.

The invention relates especially to the specific compounds described in the examples, pharmaceutically acceptable prodrug derivatives thereof and pharmaceutically acceptable salts thereof, and in particular to the specific compounds described in the examples and pharmaceutically acceptable salts thereof.

Pharmaceutically acceptable prodrug derivatives are those that may be convertible by solvolysis or under physiological conditions to the free hydroxamic acids of the invention and represent such hydroxamic acids in which the CONHOH group is derivatized in form of an O-acyl or an optionally substituted O-benzyl derivative. Preferred are the optionally substituted O-benzyl derivatives.

The compounds of the invention depending on the nature of the substituents, possess one or more asymmetric carbon atoms. The resulting diastereoisomers and enantiomers are encompassed by the instant invention.

Preferred are the compounds of the invention wherein the asymmetric carbon in the above formulae (to which are attached $R_1$ and/or $R_2$) corresponds to that of a D-aminoacid precursor and is assigned the (R)-configuration.

The general definitions used herein have the following meaning within the scope of the present invention, unless otherwise specified.

The term "lower" referred to above and hereinafter in connection with organic radicals or compounds respectively defines such as branched or unbranched with up to and including 7, preferably up to and including 4 and advantageously one or two carbon atoms.

A lower alkyl group is branched or unbranched and contains 1 to 7 carbon atoms, preferably 1–4 carbon atoms, and represents for example methyl, ethyl, propyl, butyl, isopropyl or isobutyl.

A lower alkoxy (or alkyloxy) group preferably contains 1–4 carbon atoms, advantageously 1–3 carbon atoms, and represents for example ethoxy, propoxy, isopropoxy, or most advantageously methoxy.

Halogen (halo) preferably represents chloro or fluoro but may also be bromo or iodo.

Mono- or poly-halo-lower alkyl represents lower alkyl preferably substituted by one, two or three halogens, preferably fluoro or chloro, e.g. trifluoromethyl or trifluoroethyl.

Aryl represents carbocyclic or heterocyclic aryl.

Prodrug acyl derivatives are preferably those derived from an organic carbonic acid, an organic carboxylic acid or a carbamic acid.

An acyl derivative which is derived from an organic carboxylic acid is, for example, lower alkanoyl, phenyl-lower alkanoyl or unsubstituted or substituted aroyl, such as benzoyl.

An acyl derivative which is derived from an organic carbonic acid is, for example, alkoxycarbonyl, especially lower alkoxycarbonyl, which is unsubstituted or substituted by carbocyclic or heterocyclic aryl or is cycloalkoxycarbonyl, especially $C_3$–$C_7$-cycloalkyloxycarbonyl, which is unsubstituted or substituted by lower alkyl.

An acyl derivative which is derived from a carbamic acid is, for example, amino-carbonyl which is substituted by lower alkyl, carbocyclic or heterocyclic aryl-lower alkyl, carbocyclic or heterocyclic aryl, lower alkylene or lower alkylene interrupted by O or S.

Prodrug optionally substituted O-benzyl derivatives are preferably benzyl or benzyl mono-, di-, or tri-substituted by e.g. lower alkyl, lower alkoxy, amino, nitro, halogen and/or trifluoromethyl.

Carbocyclic aryl represents monocyclic or bicyclic aryl, for example phenyl or phenyl mono-, di- or tri-substituted by one, two or three radicals selected from lower alkyl, lower alkoxy, hydroxy, halogen, cyano, trifluoromethyl, lower alkylenedioxy and oxy-$C_2$–$C_3$-alkylene; or 1- or 2-naphthyl. Lower alkylenedioxy is a divalent substituent attached to two adjacent carbon atoms of phenyl, e.g. methylenedioxy or ethylenedioxy. Oxy-$C_2$–$C_3$-alkylene is also a divalent substituent attached to two adjacent carbon atoms of phenyl, e.g. oxyethylene or oxypropylene. An example for oxy-$C_2$–$C_3$-alkylene-phenyl is 2,3-dihydrobenzofuran-5-yl.

Preferred as carbocyclic aryl is phenyl or phenyl monosubstituted by lower alkoxy, halogen, lower alkyl or trifluoromethyl, especially phenyl or phenyl monosubstituted by lower alkoxy, halogen or trifluoromethyl, and in particular phenyl.

Heterocyclic aryl represents monocyclic or bicyclic heteroaryl, for example pyridyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono- or all-substituted, by e.g. lower alkyl or halogen. Pyridyl represents 2-, 3- or 4-pyridyl, advantageously 2- or 3-pyridyl. Thienyl represents 2- or 3-thienyl, advantageously 2-thienyl. Quinolinyl represents preferably 2-, 3- or 4-quinolinyl, advantageously 2-quinolinyl. Isoquinolinyl represents preferably 1-, 3- or 4-isoquinolinyl. Benzopyranyl, benzothiopyranyl represent preferably 3-benzopyranyl or 3-benzothiopyranyl, respectively. Thiazolyl represents preferably 2- or 4-thiazolyl, advantageously 4-thiazolyl. Triazolyl is preferably 1-, 2- or 5-(1,2,4-triazolyl). Tetrazolyl is preferably 5-tetrazolyl. Imidazolyl is preferably 4-imidazolyl.

Preferably, heterocyclic aryl is pyridyl, quinolinyl, pyrrolyl, thiazolyl, isoxazolyl, triazolyl, tetrazolyl, pyrazolyl, imidazolyl, thienyl, or any said radical substituted, especially mono- or di-substituted, by lower alkyl or halogen; and in particular pyridyl.

Biaryl is preferably carbocyclic biaryl, e.g. biphenyl, namely 2, 3 or 4-biphenyl, advantageously 4-biphenyl, each optionally substituted by e.g. lower alkyl, lower alkoxy, halogen, trifluoromethyl or cyano.

$C_3$–$C_{10}$-Cycloalkyl represents a saturated cyclic hydrocarbon optionally substituted by lower alkyl which contains 3 to 10 ring carbons and is advantageously cyclopentyl, cyclohexyl, cycloheptyl or cyclooctyl optionally substituted by lower alkyl.

(Oxa or thia)-$C_3$–$C_6$-cycloalkyl represents a saturated cyclic radical wherein 1 or 2, preferably 1, oxygen or sulfur atom(s) and preferably 4–5 carbon atoms form a ring, e.g. tetrahydropyranyl, tetrahydrofuranyl, tetrahydrothiopyranyl or tetrahydrothienyl.

Oxa-cyclohexane means tetahydropyran, and thia-cyclohexane means tetrahydrothiopyran.

Carbocyclic aryl-lower alkyl represents preferably straight chain or branched aryl-$C_1$–$C_4$-alkyl in which carbocyclic aryl has meaning as defined above, e.g. benzyl or phenyl-(ethyl, propyl or butyl), each unsubstituted or substituted on phenyl ring as defined under carbocyclic aryl above, advantageously optionally substituted benzyl.

Heterocyclic aryl-lower alkyl represents preferably straight chain or branched heterocyclic aryl-$C_1$–$C_4$-alkyl in which heterocyclic aryl has meaning as defined above, e.g. 2-, 3- or 4-pyridylmethyl or (2-, 3- or 4-pyridyl)-(ethyl, propyl or butyl); or 2- or 3-thienylmethyl or (2- or 3-thienyl)-(ethyl, propyl or butyl); 2-, 3- or 4-quinolinylmethyl or (2-, 3- or 4-quinolinyl)-(ethyl, propyl or butyl); or 2- or 4-thiazolylmethyl or (2- or 4-thiazolyl)-(ethyl, propyl or butyl).

Cycloalkyl-lower alkyl represents e.g. (cyclopentyl- or cyclohexyl)-(methyl or ethyl).

Biaryl-lower alkyl represents e.g. 4-biphenylyl-(methyl or ethyl).

Acyl is derived from an organic carboxylic acid, carbonic acid or carbamic acid.

Acyl represents e.g. lower alkanoyl, carbocyclic aryl-lower alkanoyl, lower alkoxycarbonyl, aroyl, di-lower alkylaminocarbonyl or di-lower alkylamino-lower alkanoyl. Preferably, acyl is lower alkanoyl.

Acylamino represents e.g. lower alkanoylamino or lower alkoxycarbonylamino.

Acylamino-lower alkyl in R and $R_1$ is $R_3$-CONH-lower alkyl in which $R_3$ represents e.g. lower alkyl, lower alkoxy, aryl-lower alkyl, aryl-lower alkoxy, carbocyclic or heterocyclic aryl, di-lower alkylamino, N-lower alkylpiperazino, morpholino, thiomorpholino, piperidino, pyrrolidino, N-alkylpiperidyl, or (di-lower alkylamino, N-lower alkylpiperazino, morpholino, thiomorpholino, piperidino, pyrrolidino, pyridyl or N-lower alkyl-piperidyl)-lower alkyl.

Lower alkanoyl represents e.g. $C_1$–$C_7$-alkanoyl including formyl, and is preferably $C_2$–$C_4$-alkanoyl such as acetyl or propionyl.

Aroyl represents e.g. benzoyl or benzoyl mono- or di-substituted by one or two radicals selected from lower alkyl, lower alkoxy, halogen, cyano and trifluoromethyl; or 1- or 2-naphthoyl; and also e.g. pyridylcarbonyl.

Lower alkoxycarbonyl represents preferably $C_1$–$C_4$-alkoxycarbonyl, e.g. ethoxycarbonyl.

Lower alkylene represents either straight chain or branched alkylene of 1 to 7 carbon atoms and represents preferably straight chain alkylene of 1 to 4 carbon atoms, e.g. a methylene, ethylene, propylene or butylene chain, or said methylene, ethylene, propylene or butylene chain mono-substituted by $C_1$–$C_3$-alkyl (advantageously methyl) or disubstituted on the same or different carbon atoms by $C_1$–$C_3$-alkyl (advantageously methyl), the total number of carbon atoms being up to and including 7.

Esterified carboxyl is for example lower alkoxycarbonyl or benzyloxycarbonyl.

Amidated carboxyl is for example aminocarbonyl, mono- or di-lower alkylaminocarbonyl.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The compounds of the invention exhibit valuable pharmacological properties in mammals including man and are particularly useful as inhibitors of matrix-degrading metalloproteinase enzymes (=metalloproteinases).

As the compounds of the invention are inhibitors of stromelysin, gelatinase, collagenase and macrophage metalloelastase, and inhibit matrix degradation, they are particularly useful in mammals as agents for the treatment of e.g. osteoarthritis, rheumatoid arthritis, corneal ulceration, periodontal disease, tumor metastasis, tumor invasion or progression, progression of HIV-infection and HIV-infection related disorders, atherosclerosis, osteoporosis and emphysema.

Illustrative of the matrix degrading metalloproteinase inhibitory activity, compounds of the invention prevent the degradation of cartilage caused by exogenous or endogenous stromelysin in mammals. They inhibit e.g. the stromelysin-induced degradation of aggrecan (large aggregating proteoglycan), link protein or type IX collagen in mammals.

Beneficial effects are evaluated in pharmacological tests generally known in the art, and as illustrated herein.

The above-cited properties are demonstrable in in vitro and in vivo tests, using advantageously mammals, e.g. rats, guinea pigs, dogs, rabbits, or isolated organs and tissues, as well as mammalian enzyme preparations. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-5}$ molar and $10^{-10}$ molar concentrations. The dosage in vivo may range, depending on the route of administration, between about 0.1 and 50 mg/kg.

One test to determine the inhibition of stromelysin activity is based on its hydrolysis of Substance P using a modified procedure of Harrison et al. (Harrison, R. A., Teahan J., and Stein R., A semicontinuous, high performance chromatography based assay for stromelysin, Anal. Biochem. 180, 110–113 (1989)). In this assay, Substance P is hydrolyzed by recombinant human stromelysin to generate a fragment, Substance P 7–11, which can be quantitated by HPLC. In a typical assay, a 10 mM stock solution of a compound to be tested is diluted in the assay buffer to 50 µM, mixed 1:1 with 8 µg recombinant human stromelysin (mol. wt. 45–47 kDa, 2 Units; where 1 Unit produces 20 mmoles of Substance P 7–11 in 30 minutes) and incubated along with 0.5 mM Substance P in a final volume of 0.125 ml for 30 minutes at 37° C. The reaction is stopped by adding 10 mM EDTA and Substance P7-11 is quantified on RP-8 HPLC. The $IC_{50}$ for inhibition of stromelysin activity and Ki are calculated from control reaction without the inhibitor.

Illustrative of the invention, N-hydroxy-2(R)-[[4-methoxybenzenesulfonyl](3-picolyl)amino]-3-methylbutanamide hydrochloride exhibits a Ki of 17 nM in this assay.

Stromelysin activity can also be determined using human aggrecan as a substrate. This assay allows the confirmation in-vitro that a compound can inhibit the action of stromelysin on its highly negatively-charged natural substrate, aggrecan (large aggregating prtoeoglycan). Within the cartilage, proteoglycan exists as an aggregate bound to hyaluronate. Human proteoglycan aggregated to hyaluronate is used as an enzyme substrate. The assay is set up in 96-well microtiter plates allowing rapid evaluation of compounds. The assay has three major steps:

1) Plates are coated with hyaluronate (human umbilical chord, 400 ug/ml), blocked with BSA (5 mg/ml), and then proteoglycan (human articular cartilage D1 -chondroitinase ABC digested, 2 mg/ml) is bound to the hyaluronate. Plates are washed between each step.
2) Buffers+inhibitor (1 to 5,000 nM)+recombinant human stromelysin (1–3 Units/well) are added to wells. The plates are sealed with tape and incubated overnight at 37° C. The plates are then washed.
3) A primary (3B3) antibody (mouse IgM, 1:10,000) is used to detect remaining fragments. A secondary antibody, peroxictidase-linked anti-IgM, is bound to the primary antibody. OPD is then added as a substrate for the peroxidase and the reaction is stopped with sulfuric acid. The $IC_{50}$ for inhibition of stromelysin activity is graphically derived and Ki is calculated.

Illustrative of the invention, N-hydroxy-2(R)-[[4-methoxybenzenesulfonyl](3-picolyl)amino]-3-methylbutanamide hydrochloride exhibits an $IC_{50}$ of 55 nM in this assay.

Collagenase activity is determined as follows: ninety six-well, flat-bottom microtiter plates are first coated with bovine type I collagen (35 ug/well) over a two-day period at 30° C. using a humidified and then dry atmosphere; plates are rinsed, air dried for 3–4 hours, sealed with Saran wrap and stored in a refrigerator. Human recombinant fibroblast collagenase and a test compound (or buffer) are added to wells (total volume=0.1 ml) and plates are incubated for 2 hours at 35° C. under humidified conditions; the amount of collagenase used per well is that causing approximately 80% of maximal digestion of collagen. The incubation media are removed from the wells, which are then rinsed with buffer, followed by water. Coomasie blue stain is added to the wells for 25 minutes, removed, and wells are again rinsed with water. Sodium dodecyl sulfate (20% in 50% dimethylformamide in water) is added to solubilize the remaining stained collagen and the optical density at 570 nM wave length is measured. The decrease in optical density due to collagenase (from that of collagen without enzyme) is compared to the decrease in optical density due to the enzyme in the presence of test compound, and percent inhibition of enzyme activity is calculated. $IC_{50}$'s are determined from a range of concentrations of inhibitors (4–5 concentrations, each tested in triplicate), and $K_i$ values are calculated.

Illustrative of the invention, N-hydroxy-2(R)-[[4-methoxybenzenesulfonyl](3-picolyl)amino]-3-methylbutanamide hydrochloride exhibits a Ki of 62 nM in this assay.

The effect of compounds of the invention in-vivo can be determined in rabbits. Typically, four rabbits are dosed orally with a compound up to four hours before being injected intra-articularly in both knees (N=8) with 40 Units of recombinant human stromelysin dissolved in 20 mM Tris, 10 mM $CaCl_2$, and 0.15 M NaCl at pH 7.5. Two hours later the rabbits are sacrificed, synovial lavage is collected, and keratan sulfate (KS) and sulfated glycosaminoglycan (S-GAG) fragments released into the joint are quantitated. Keratan sulfate is measured by an inhibition ELISA using the method of Thonar (Thonar, E. J.-M. A., Lenz, M. E., Klinsworth, G. K., Caterson, B., Pachman, L. M., Glickman, P., Katz, R., Huff, J., Keutmer, K. E. Quantitation of keratan sulfate in blood as a marker of cartilage catabolism, Arthr. Rheum. 28, 1367–1376 (1985)). Sulfated glycosaminoglycans are measured by first digesting the synovial lavage with streptomyces hyaluronidase and then measuring DMB dye binding using the method of Goldberg (Goldberg, R. L. and Kolibas, L. An improved method for determining proteoglycan synthesized by chondrocytes in culture. Connect. Tiss. Res. 24,, 265–275 (1990)). For an i.v. study, a compound is solubilized in 1 ml of PEG-400, and for a p.o. study, a compound is administered in 5 ml of fortified corn starch per kilogram of body weight.

Illustrative of the invention, N-hydroxy-2(R)-[[4-methoxybenzenesulfonyl](3-picolyl)-amino]-3-methylbutanamide hydrochloride produces a 72% and 70% inhibition, respectively, in the release of KS and S-GAG fragments into the joint when given to rabbits at a dose of 30 mg/kg, 4 hours prior to the injection of human recombinant stromelysin.

The effect in protecting against cartilage degradation in arthritic disorders can be determined e.g. in a surgical model of osteoarthritis described in Arthritis and Rheumatism, Vol. 26, 875–886 (1983).

Illustrative of the invention, N-hydroxy-2(R)-[[4-methoxybenzenesulfonyl](3-picolyl)-amino]-3-methylbutanamide hydrochloride protects against cartilage degradation in this model.

The effect on ulcerations, e.g. ocular ulcerations, can be determined in the rabbit by measuring the reduction of corneal ulceration following an alkali burn to the cornea.

Macrophage metalloelastase (MME) inhibitory activity can be determined by measuring the inhibition of the degradation of [$^3$H]-elastin by truncated recombinant mouse macrophage metalloelastase as follows:

About 2 ng of recombinant truncated mouse macrophage metalloelastase (FASEB Journal Vol. 8, A151, 1994), purified by Q-Sepharose column chromatography is incubated with test compounds at the desired concentrations in the presence of 5 nM $CaCl_2$, 400 nM NaCl, [$^3$H]elastin (60,000 cpm/tube), and 20 mM Tris, pH 8.0, at 37° C. overnight. The samples are spun in a microfuge centrifuge at 12,000 rpm for 15 minutes. An aliquot of the supernatant is counted in a scintillation counter to quantitate degraded [$^3$H]elastin. $IC_{50}$'s are determined from a range of concentrations of the test compounds and the percent inhibition of enzyme activity obtained.

Illustrative of the invention, N-hydroxy-2(R)-[[4-methoxybenzenesulfonyl](3-picolyl)amino]-3-methylbutanamide hydrochloride inhibits the degradation of [$^3$H]elastin by mouse macrophage metalloelastase with an $IC_{50}$ of about 8 nM.

The effect of the compounds of the invention for the treatment of emphysema can be determined in animal models described in American Review of Respiratory Disease 117, 1109 (1978).

Inhibition of the production and secretion of TNF-α can be determined e.g. as described in Nature 370, 555, 558 (1994). Anti-inflammatory activity can be determined in standard inflammation and arthritic animal models well-known in the art, e.g. the adjuvant arthritis model in rats, and the collagen induced arthritis model in mice.

The antitumor effect of the compounds of the invention can be determined e.g. by measuring the growth of human tumors implanted subcutaneously in Balb/c nude treated mice according to methodology well-known in the art in comparison to placebo treated mice.

Illustrative of the antitumor activity, the compound of example 1 (a), administered at a dose of 30 mg/Kg p.o. twice daily to mice 7–17 days after implantation of human tumors, significantly inhibits the growth of e.g. estrogen dependent human breast carcinoma BT20 and MCF7, human bladder carcinoma T24, human colon carcinoma Colo 205, human lung adenocarcinoma A549 and human ovarian carcinoma NEH-OVCAR$_3$. At oral doses of 30 and 60 mg/Kg twice daily, the compound of example 1 (a) not only inhibits the growth of breast carcinoma MCF-7 but also induces regression of the tumor.

The effect on tumor angiogenesis can be determined e.g. in rats implanted with Walker 256 carcinoma in pellets to stimulate anglogenesis from vessels of the limbus, as described by Galardy et al., Cancer Res. 54, 4715 (1994).

The effect of the compounds of the invention on atherosclerotic conditions can be evaluated using atherosclerotic plaques from cholesterol-fed rabbits which contain activated matrix metalloproteinases as described by Sukhova et al., Circulation 90, 1404 (1994). The inhibitory effect of compounds of the invention, e.g. the compound of example 1(a), on matrix metalloproteinase enzyme activity in rabbit atherosclerotic plaques is determined by in situ zymography, as described by Galis et al., J. Clin. Invest. 94, 2493 (1994), and is indicative of plaque stabilization.

The effect on resterosis and vascular remodeling can be evaluated in the rat ballooned carotid artery model. Indicative of the effect of compounds of the invention in restenosis and vascular remodeling e.g. post-angioplasty or post-atherectomy, the compound of example 1(a) inhibits intimal early lesion formation (at 7 and 9 days) following balloon injury in the rat ballooned carotid artery model.

The effect on demyelinating disorders of the nervous system, such as multiple sclerosis, can be evaluated by measuring the reversal of experimental antioimmune encephalomyelitis in mice, e.g. as described by Gijbels et al., J. Clin. Invest. 94, 2177 (1994).

The compounds of formula I can be prepared e.g. by condensing a carboxylic acid of formula IV,

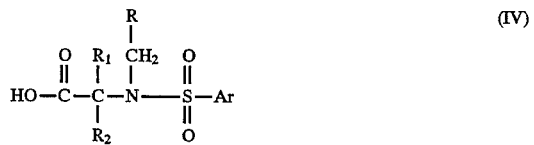

or a reactive functional derivative thereof, wherein R, R$_1$, R$_2$ and Ar having meaning as defined in claim 1, with hydroxylamine of formula V,

optionally in protected form, or a salt thereof;

and, if necessary, temporarily protecting any interfering reactive group(s), and then liberating the resulting compound of the invention; and, if required or desired, converting a resulting compound of the invention into another compound of the invention, and/or, if desired, converting a resulting free compound into a salt or a resulting salt into a free compound or into another salt; and/or separating a mixture of isomers or racemates obtained into the single isomers or racemates; and/or, if desired, resolving a racemate into the optical antipodes.

In starting compounds and intermediates which are convened to the compounds of the invention in a manner described herein, functional groups present, such as amino, carboxyl and hydroxy groups, are optionally protected by conventional protecting groups that are common in preparative organic chemistry. Protected amino, carboxyl and hydroxy groups are those that can be convened under mild conditions into free amino and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1991.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters for example succinimido, phthalimido or 4-nitrophenyl esters; lower alkyl esters are for example the methyl or ethyl esters.

Also, a reactive esterified derivative of an alcohol in any of the reactions cited herein represents said alcohol esterified by a strong acid, especially a strong inorganic acid, such as a hydrohalic acid, especially hydrochloric, hydrobromic or hydroiodic acid, or sulphuric acid, or by a strong organic acid, especially a strong organic sulfonic acid, such as an aliphatic or aromatic sulfonic acid, for example methanesulfonic acid, 4-methylbenzene-sulfonic acid or 4-bromobenzenesulfonic acid. A said reactive esterified derivative is especially halo, for example chloro, bromo or iodo, or aliphatically or aromatically substituted sulfonyloxy, for example methanesulfonyloxy, 4-methylbenzenesulfonyloxy (tosyloxy).

In the above processes for the synthesis of compounds of the invention can be carried out according to methodology generally known in the art for the preparation of hydroxamic acids and derivatives thereof.

The synthesis according to the above process (involving the condensation of a free carboxylic acid of formula IV with an optionally hydroxy protected hydroxylamine derivative of formula V can be carded out in the presence of a condensing agent, e.g. 1,1'-carbonyldiimidazole, or N-(dimethylaminopropyl)-N'-ethylcarbodiimide or dicyclohexylcarbodiimide, with or without 1-hydroxybenzotriazole in an inert polar solvent, such as dimethylformamide or dichloromethane, preferably at room temperature.

The synthesis involving the condensation of a reactive functional derivative of an acid of formula IV as defined above, e.g. an acid chloride or mixed anhydride with optionally hydroxy protected hydroxylamine, or a salt thereof, in presence of a base such as triethylamine can be carried out, at a temperature ranging preferably from about −78° C. to +75° C., in an inert organic solvent such as dichloromethane or toluene.

Protected forms of hydroxylamine (of formula V) in the above process are those wherein the hydroxy group is protected for example as a t-butyl ether, a benzyl ether or tetrahydropyranyl ether, or as a trimethylsilyl derivative. Removal of said protecting groups is carded out according to methods well known in the art, e.g. hydrogenolysis or acid hydrolysis. Hydroxylamine is preferably generated in sire from a hydroxylamine salt, such as hydroxylamine hydrochloride.

The starting carboxylic acids of formula IV can be prepared as follows:

An amino acid of formula VI

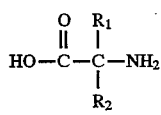 (VI)

wherein $R_1$ and $R_2$ have meaning as defined herein, is first esterified with a lower alkanol, e.g. methanol, in the presence of e.g. thionyl chloride to obtain an aminoester which is treated with a reactive functional derivative of the appropriate arylsulfonic acid of the formula VII

 (VII)

wherein Ar has meaning as defined hereinabove, e.g. with the arylsulfonyl chloride, in the presence of a suitable base such as triethylamine using a polar solvent such as tetrahydrofuran, toluene, acetonitrile to obtain a compound of the formula VIII

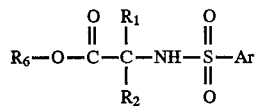 (VIII)

wherein $R_1$, $R_2$ and Ar have meaning as defined herein and $R_6$ is a protecting group, e.g. lower alkyl. Treatment thereof with a reactive esterified derivative of the alcohol of the formula IX

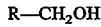 (IX)

wherein R has meaning as defined herein, such as the halide, e.g. the chloride, bromide or iodide derivative thereof, in the presence of an appropriate base, such as potassium carbonate or sodium hydride, in a polar solvent such as dimethylformamide. The resulting compound corresponding to an ester of a compound of formula IV can then be hydrolyzed to the acid of formula IV, using standard mild methods of ester hydrolysis, preferably under acidic conditions. For compounds of formula Ia (wherein R and $R_1$ of formula I are combined) the starting materials are prepared by treating a carboxylic acid of formula X

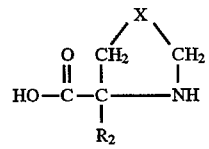 (X)

or an ester thereof, wherein $R_2$ and X have meaning as defined above, with a reactive functional derivative of a compound of the formula $ArSO_3H$ (VII) under conditions described for the preparation of a compound of formula VIII.

The starting materials of formula VI, VII, IX and X are either known in the art, or can be prepared by methods well-known in the art or as described herein.

Optically active D-aminoacids of formula VI (the R-enantiomers) can be prepared according to methods known in the art, e.g. according to methods described in Tetrahedron Letters 28, 39 (1987), J. Am. Chem. Soc. 109, 7151 (1987) and J. Am. Chem. Soc. 110, 1547 (1988).

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carded out, or the process is discontinued at any stage thereof, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials and processes for their manufacture.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The hydroxamic acids or carboxylic acid intermediates can thus be resolved into their optical antipodes e.g. by fractional crystallization of d- or l-(alphamethylbenzylamine, cinchonidine, cinchonine, quinine, quinidine, ephedrine, dehydroabietylamine, brucine or strychnine)-salts.

Finally, acidic compounds of the invention are either obtained in the free form, or as a salt thereof.

Acidic compounds of the invention may be convened into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be convened into the free compounds by treatment with acids. These or other salts can also be used for purification of the compounds obtained.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit matrix-degrading metalloproteinases, and for the treatment of disorders responsive thereto, comprising an effective amount of a pharmacologically active compound of the invention, alone or in combination, with one or more pharmaceutically acceptable carders.

The pharmacologically active compounds of the invention are useful in the manufacture of pharmaceutical compositions comprising an effective amount thereof in conjunction or admixture with excipients or carders suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g. to the skin and eyes, are preferably aqueous solutions, ointments, creams or gels well-known in the art.

The pharmaceutical formulations contain an effective matrix-degrading metalloproteinase inhibiting amount of a compound of the invention as defined above either alone, or in combination with another therapeutic agent, e.g. an antiinflammatory agent with cyclooxygenase inhibiting activity, or other antirheumatic agents such as methotrexate, each at an effective therapeutic dose as reported in the art. Such therapeutic agents are well-known in the art.

Examples of antiinflammatory agents with cyclooxygenase inhibiting activity are diclofenac sodium, naproxen, ibuprofen, and the like.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 10 and 1000 mg, advantageously between about 25 and 250 mg of the active ingredient.

The present invention also relates to methods of using the compounds of the invention and their pharmaceutically acceptable salts, or pharmaceutical compositions thereof, in mammals for inhibiting the matrix-degrading metalloproteinases, e.g. stromelysin, collagenase and macrophage metalloelastase, for inhibiting tissue matrix degradation, and for the treatment of matrix-degrading metalloproteinase dependent conditions as described herein, e.g. osteoarthritis, also tumors (tumor growth, tumor metastasis, progression or invasion), pulmonary disorders, and the like described herein. Tumors (carcinomas) include human breast, lung, bladder, colon, prostate and ovarian cancer, and skin cancer, including melanoma and Kaposi's sarcoma.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art. The concentration for $[\alpha]_D$ determinations is expressed in mg/ml.

Example 1: (a) N-(t-Butyloxy)-2(R)-[[4-methoxybenzenesulfonyl](3-picolyl)amino]-3-methylbutanamide (4.1 g, 9.13 mmol) is dissolved in dichloroethane (150 mL) containing ethanol (0.53 ml, 9.13 mmol) in a round bottom flask, and the reaction is cooled to −10° C. Hydrochloric acid gas (from a lecture bottle) is bubbled through for 30 minutes. The reaction is sealed, allowed to slowly warm to room temperature, and stirred for 2 days. The solvent is reduced to ⅓ volume by evaporation and triturated with ether. The mixture is filtered, filter cake removed, and dried in vacuo to provide N-hydroxy-2(R)-[[4-methoxybenzenesulfonyl](3-picolyl)amino]-3-methylbutanamide hydrochloride as a white solid, m.p. 169°–170° C. (dec), and having the following structure:

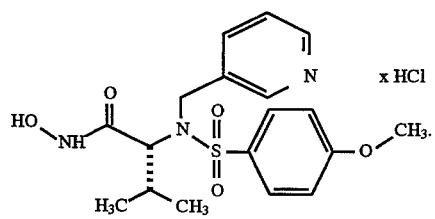

The starting material is prepared as follows:

To a solution of D-valine (15.0 g, 128.0 mmol) in 1:1 dioxane/water (200 mL) containing triethylamine (19.4 g, 192.0 mmol) at room temperature is added 4-methoxybenzene-sulfonyl chloride (29.0 g, 141.0 mmol), and the reaction mixture is stirred at room temperature overnight. The mixture is then diluted with methylene chloride, washed with 1N aqueous hydrochloric acid and water. The organic layer is washed again with brine, dried (Na₂SO₄), and the solvent is evaporated to provide N-[4-methoxybenzenesulfonyl]-(D)-valine as a crude product. A solution of this crude product (15.0 g) in toluene (100 mL) containing N,N-dimethylformamide di-t-butyl acetal (50 mL, 206.5 mmol) is heated to 95° C. for 3 hours. The solvent is then evaporated. The crude product is purified by silica gel chromatography (30% ethyl acetate/hexanes) to provide N-[4-methoxybenzene-sulfonyl]-(D)-valine t-butyl ester.

To a solution of N-[4-methoxybenzenesulfonyl]-(D)-valine t-butyl ester (4.38 g, 13.0 mmol) in dimethylformamide (200 mL) is added 3-picolyl chloride hydrochloride (2.3 g, 14.0 mmol) followed by potassium carbonate (17.94 g, 130.0 mmol). The reaction mixture is stirred at room temperature for 2 days. The mixture is then diluted with water and extracted with ethyl acetate. The combined organic extracts are washed with brine, dried (Na₂SO₄), and the solvent is evaporated. The crude product is purified by silica gel chromatography (ethyl acetate) to give t-butyl 2(R)-[N-[4-methoxybenzenesulfonyl]-(3-picolyl)amino]-3-methylbutanoate.

t-Butyl 2(R)-[[4-methoxybenzenesulfonyl](3-picolyl)amino]-3-methylbutanoate (5.3 g, 12.2 mmol) is dissolved in methylene chloride (150 mL) and cooled to −10° C. Hydrochloric acid gas is bubbled into the solution for 10 minutes. The reaction mixture is then sealed, warmed to room temperature and stirred for 4 hours. The solvent is then evaporated to provide 2(R)-[[4-methoxybenzenesulfonyl](3-picolyl)amino]-3-methyl-butanoic acid hydrochloride.

2(R)-[[4-methoxybenzenesulfonyl](3-picolyl)amino]-3-methylbutanoic acid hydrochloride (5.0 g, 12.06 mmol), 1-hydroxybenzotriazole (1.63 g, 12.06 mmol), 4-methylmorpholine (6.6 mL, 60.31 mmol), and O-t-butylhydroxylamine hydrochloride (54.55 g, 36.19 mmol) are dissolved in methylene chloride (200 mL). N-[Dimethylaminopropyl]-N'-ethylcarbodiimide hydrochloride (3.01 g, 15.68 mmol) is added, and the reaction is stirred overnight. The reaction is then diluted with water and extracted with methylene chloride. The combined organic extracts are washed with brine, dried (Na₂SO₄), and the solvent is evaporated. The crude product is purified by silica gel chromatography (2% methanol/methylene chloride) to give N-(t-butyloxy)-2(R)-[[4-methoxybenzenesulfonyl]-(3-picolyl)amino]-3-methylbutanamide.

(b) L-tartaric acid salt, m.p. 114°–116° C.

(c) Methanesulfonic acid salt, m.p. 139°–141.5° C.

(d) Maleic acid salt, m.p. 133°–134° C.

Example 2: The following compounds are prepared similarly to Example 1:

a) N-Hydroxy-2(S)-[[4-methoxybenzenesulfonyl](3-picolyl)amino]-3-methylbutanamide hydrochloride, m.p. 170.5°–171 ° C., by starting the synthesis with L-valine, and carrying out the subsequent steps as described above.

(b) N-hydroxy-2(R)-[[4-methoxybenzenesulfonyl](3-picolyl)amino]-4-methylpentanamide hydrochloride, m.p. 128°–129° C.

The first two steps are carried out as described in example 1, except the synthesis was started with D-leucine. The alkylation step is different, as described below.

To a solution of t-butyl 2(R)-[[4-methoxybenzenesulfonyl]amino]-4-methylpentanoate (10.0 g, 27.92 mmol) in dimethylformamide (250 mL) at room temperature is added 3-picolyl chloride hydrochloride (4.81 g, 29.32 mmol) followed by sodium hydride (2.79 g, 69.80 mmol, 60% in oil). The reaction mixture is stirred at room temperature for 48 hours. The mixture is quenched with water and extracted with ethyl acetate. The combined organic extracts are washed with brine, dried (Na₂SO₄), and the solvent is evaporated. The crude product is purified by silica gel chromatography (45% ethyl acetate/hexanes) to provide t-butyl 2(R)-[[4-methoxybenzenesulfonyl](3-picolyl)-amino]-4-methylpentanoate.

All of the following steps are carried out as described above in example 1.

(c) N-Hydroxy-2(R)-[[4-methoxybenzenesulfonyl](6-chloropiperonyl)amino]-4-methylpentanamide, m.p. 85°–87° C., by starting the synthesis with D-leucine and alkylating with 6-chloropiperonyl chloride (=6-chloro-3,4-methylenedioxy-benzylchloride) in the third step.

(d) N-Hydroxy-2(R)-[[4-methoxybenzenesulfonyl](piperonyl)amino]-4-methylpentanamide, m.p. 145°–147° C., by starting the synthesis with D-leucine and alkylating with piperonyl chloride (=3,4-methylenedioxybenzylchloride) in the third step.

(e) N-Hydroxy-2(R)-[[4-methoxybenzenesulfonyl](2-picolyl)amino]-4-methylpentanamide, m.p. 89°–90° C., by starting the synthesis with D-leucine and alkylating with 2-picolyl chloride in the third step.

(f) N-Hydroxy-2(R)-[[4-methoxybenzenesulfonyl](2-picolyl)amino]-3-methylbutanamide hydrochloride, m.p. 140°–142° C., by starting the synthesis with D-valine and alkylating with 2-picolyl chloride in the third step.

(g) N-Hydroxy-2(R)-[[4-methoxybenzenesulfonyl](3-picolyl)amino]-4,4-dimethylpentanamide hydrochloride, m.p. 130°–150° C. (slow melt), by starting the synthesis with D-t-butylalanine and alkylating with 3-picolyl chloride in the third step.

(h) N-Hydroxy-2(R)-[[4-methoxybenzenesulfonyl](3-picolyl)amino]-2-cyclohexylacetamide hydrochloride, m.p. 149.5°–152.0° C., by starting the synthesis with (D)-cyclohexylglycine hydrochloride.

The starting amino acid is prepared as follows:

(D)-phenylglycine (10.0 g, 66.2 mmol) is suspended in 2N hydrochloric acid (100 mL) containing platinum (IV) oxide hydrate (267 mg). The mixture is shaken in a Parr hydrogenation apparatus for 24 hours under a hydrogen pressure of 50 psi. The resultant suspended crystalline material, (D)-cyclohexylglycine hydrochloride, was used without further purification.

(i) N-Hydroxy-2(R)-[[(2,3-dihydrobenzofuran)-5-sulfonyl](3-picolyl)amino]3-methylbutanamide hydrochloride, m.p. 150.0°–153.0° C., by starting the synthesis with 2,3-dihydrobenzofuran-5-sulfonyl chloride.

The starting sulfonyl chloride is prepared as follows:

2,3-dihydrobenzofuran (6.0 g, 49.94 mmol) is added over 20 minutes to chlorosulfonic acid (29.09 g, 249.69 mmol) at −20° C. The reaction mixture is quenched by addition of ice followed by water (20 mL). The mixture is then extracted with ethyl acetate. The combined organic extracts are washed with brine, dried (Na₂SO₄), and the solvent is evaporated. The crude product is purified by silica gel chromatography (30% ethyl acetate/hexane) to give 2,3-dihydrobenzofuran-5-sulfonyl chloride (3.3 g).

(j) N-Hydroxy-2-[[4-methoxybenzenesulfonyl](3-picolyl)-amino]-3-methylbutanamide hydrochloride, m.p. 139.5°–142° C., by starting the synthesis with DL-valine.

(k) N-Hydroxy-2(R)-[[4-ethoxybenzenesulfonyl](3-picolyl)-amino]-3-methylbutanamide hydrochloride, [α]$_D^{25}$=+34.35 (c=5.84, CH₃OH).

(l) N-Hydroxy-2(R)-[[4-methoxybenzenesulfonyl](2-picolyl)amino]-2-cyclohexylacetamide hydrochloride, m.p. 127°–140°, by starting the syntheses with (D)-cyclohexylglycine hydrochloride, and carrying out the subsequent steps as described above.

(m) N-Hydroxy-2-[[4-methoxybenzenesulfonyl](2-methylthiazol-4-ylmethyl)amino]-2-cyclohexylacetamide hydrochloride, m.p. 137°–139° C., using 4-chloromethyl-2-methylthiazole in the alkylation step.

(n) N-Hydroxy-2-[[4-methoxybenzenesulfonyl](2-quinolinylmethyl)amino]-2-cyclohexylacetamide hydrochloride, m.p. 121°–123° C., using 2-chloromethylquinoline hydrochloride in the alkylation step.

Example 3: 2(R)-[[4-Methoxybenzenesulfonyl](benzyl) amino]-4-methylpentanoic acid (4.38 g, 11.2 mmol) is dissolved in methylene chloride (56.0 mL). To this solution is added oxalyl chloride (1.95 mL, 22.4 mmol) and dimethylformamide (0.86 mL, 11.2 mmol), and the reaction is stirred at room temperature for 90 minutes. Meanwhile, in a separate flask, hydroxylamine hydrochloride (3.11 g, 44.8 mmol) and triethylamine (9.36 mL, 67.1 mmol) are stirred in tetrahydrofuran (50.0 mL) and water (3.5 mL) at 0° C. for 15 minutes. After 90 minutes, the methylene chloride solution is added in one portion to the second flask, and the combined contents are stirred for three days as the flask gradually warms up to room temperature. The reaction is then diluted with acidic water (pH=~3), and extracted several times with ethyl acetate. The combined organic layers are dried ($Na_2SO_4$), and the solvent is evaporated. The product is purified by silica gel chromatography (1% methanol/methylene chloride) to give N-hydroxy-2(R)-[[4-methoxybenzenesulfonyl](benzyl)amino]-4-methylpentanamide, m.p. 48°–52° C.

The starting material is prepared as follows:

(D)-leucine (7.1 g, 53.9 mmol) is dissolved in dioxane (60.0 mL) and water (60.0 mL). To this solution is added triethylamine (11.3 mL, 80.9 mmol) and 4-methoxybenzenesulfonyl chloride (12.25 g, 59.3 mmol), and the reaction is stirred at room temperature overnight. The reaction is then diluted with methylene chloride and washed successively with 2.5N hydrochloric acid, water, and brine. The organic phase is dried ($Na_2SO_4$), and the solvent is evaporated to give N-[4-methoxybenzenesulfonyl]-(D)-leucine, which is used without further purification.

N-[4-methoxybenzenesulfonyl]-(D)-leucine (14.0 g, 46.5 mmol) is dissolved in toluene (100.0 mL), and heated to 90° C. N,N-Dimethylformamide di-t-butyl acetal (45.0 mL, 186.0 mmol) is added dropwise over 20 minutes, and then the reaction is kept at 90° C. for another 2 hours. After cooling back down, the reaction is diluted with ethyl acetate and washed successively with saturated sodium bicarbonate, water, and brine. The organic phase is dried ($Na_{2SO4}$), and the solvent is evaporated. The product is purified by silica gel chromatography (20% ethyl acetate/hexane) to give N-[4-methoxybenzenesulfonyl]-(D)-leucine t-butyl ester.

To a suspension of sodium hydride (0.68 g, 14.1 mmol) in dimethylformamide (60.0 mL), is added N-[4-methoxybenzenesulfonyl]-(D)-leucine t-butyl ester (5.02 g, 14.06 mmol) in dimethylformamide (10.0 mL). After stirring at room temperature for 20 minutes, benzyl bromide (1.67 mL, 14.06 mmol) is added, and the reaction is stirred overnight at room temperature. The reaction is then partitioned between ethyl acetate and acidic water (pH=5), the organic layer is dried ($Na_2SO_4$), and the solvent is evaporated. The product is purified by silica gel chromatography (10% ethyl acetate/hexane) to give t-butyl 2(R)-[[4-methoxybenzenesulfonyl](benzyl)amino]-4-methylpentanoate.

t-Butyl 2(R)-[[4-methoxybenzenesulfonyl](benzyl) amino]-4-methylpentanoate (5.38 g, 12.02 mmol) is dissolved in methylene chloride (100.0 mL). Hydrochloric acid gas (from a lecture bottle) is bubbled through the solution for 20 minutes. The reaction is sealed and stirred overnight at room temperature. The solvent is then evaporated to give 2(R)-[[4-methoxybenzenesulfonyl](benzyl)amino]-4-methylpentanoic acid.

Example 4: The following compounds are prepared similarly to example 3:

(a) N-Hydroxy-2(R)-[[4-methoxybenzenesulfonyl] (benzyl)amino]-2-phenylacetamide, m.p. 128°–129° C., by starting the synthesis with (D)-phenylglycine, and carrying out the subsequent steps as described in example 3.

(b) N-Hydroxy-2-[[4-methoxybenzenesulfonyl](benzyl) amino]-2-t-butylacetamide, m.p. 69°–73° C., by starting the synthesis with t-butylglycine, and carrying out the subsequent steps as described in example 3.

(c) N-Hydroxy-2(R)-[[4-methoxybenzenesulfonyl](4-fluorobenzyl)amino]-4-methylpentanamide, m.p. 48°–51° C., by starting the synthesis with (D)-leucine, and carrying out the subsequent steps as described in example 3, with the exception that 4-fluorobenzyl bromide is used in place of benzyl bromide.

(d) N-Hydroxy-2(R)-[[4-methoxybenzenesulfonyl] (benzyl)amino]-3-methylbutanamide, m.p. 179°–180° C., by starting the synthesis with (D)-valine, and carrying out the subsequent steps as described in example 3.

(e) N-Hydroxy-2(R)-[[4-methoxybenzenesulfonyl] (benzyl)amino]-4,4-dimethylpentanamide, by starting the synthesis with (D)-neopentylglycine, and carrying out the subsequent steps as described in example 3.

(f) N-Hydroxy-2(R)-[[4-methoxybenzenesulfonyl(benzyl) amino]-3- hydroxypropanamide, m.p. 65°, by starting the synthesis with (D)-serine, and carrying out the subsequent steps as described in example 3.

Example 5: 3-[4-Methoxybenzenesulfonyl]-5,5-dimethylthiazolidine-4(S)-carboxylic acid (2.0 g, 6.0 mmol) is dissolved in methylene chloride (30.0 mL). To this solution is added oxalyl chloride (1.1 mL, 12.1 mmol) and dimethylformamide (0.50 mL, 6.0 mmol), and the reaction is stirred at room temperature for 2 hours. Meanwhile, in a separate flask, hydroxylamine hydrochloride (1.74 g, 25.0 mmol) and triethylamine (5.0 mL, 36.0 mmol) are stirred in tetrahydrofuran (25.0 mL) and water (2.0 mL) at 0° C. for 15 minutes. After 2 hours, the methylene chloride solution is added in one portion to the second flask, and the combined contents are stirred overnight as the flask gradually warms up to room temperature. The reaction is then diluted with acidic water (pH=~3), and extracted several times with ethyl acetate. The combined organic layers are dried ($Na_2SO_4$), and the solvent is evaporated. The product is purified by silica gel chromatography (60% ethyl acetate/hexane) to give N-hydroxy-3-[4-methoxybenzenesulfonyl]-5,5-dimethylthiazolidine-4(S)-carboxamide, m.p. 68°–71° C.

The starting material is prepared as follows:

(D)-5,5-Dimethylthiazolidine-4-carboxylic acid (1.0 g, 6.2 mmol) is dissolved in dioxane (10.0 mL) and water (10.0 mL). To this solution is added triethylamine (1.3 mL, 9.3 mmol) and 4-methoxybenzenesulfonyl chloride (1.41 g, 6.82 mmol), and the reaction is stirred at room temperature for three days. The reaction is then diluted with ethyl acetate and washed successively with 2.5N hydrochloric acid, water, and brine. The organic phase is dried ($Na_2SO_4$), and the solvent is evaporated to give 3-[4-methoxybenzenesulfonyl]-5,5-dimethylthiazolidine-4(S)-carboxylic acid, which is used without further purification.

Example 6: 1-[4-Methoxybenzenesulfonyl]-pyrrolidine-2 (R)-carboxylic acid (1.12 g, 3.93 mmol) is dissolved in methylene chloride (40.0 mL). To this solution is added oxalyl chloride (0.69 mL, 7.85 mmol) and dimethylformamide (0.30 mL, 3.93 mmol), and the reaction is stirred at room temperature for 30 minutes. Meanwhile, in a separate flask, hydroxylamine hydrochloride (1.1 g, 15.7 mmol) and triethylamine (3.3 mL, 23.5 mmol) are stirred in tetrahydrofuran (20.0 mL) and water (4.0 mL) at 0° C. for 15 minutes. After 30 minutes, the methylene chloride solution is added in one portion to the second flask, and the combined contents are stirred overnight as the flask gradually warms up to room temperature. The reaction is then diluted with acidic water (pH=~3), and extracted several times with ethyl acetate. The combined organic layers are dried ($MgSO_4$), and the solvent is evaporated. The product is purified by silica gel chromatography (50% ethyl acetate/hexane) to give N-hydroxy-1-[4-methoxybenzenesulfonyl]-pyrrolidine-2(S)-carboxamide, m.p. 163.5°–165.5° C.

The starting material is prepared as follows:

(D)-proline (0.78 g, 6.77 mmol) is suspended in methylene chloride (25.0 mL). To this solution is added triethylamine (1.13 mL, 8.12 mmol) and 4-methoxybenzenesulfonyl chloride (1.4 g, 6.77 mmol), and the reaction is stirred at room temperature for two days. The reaction is then diluted with methylene chloride and washed successively with 1N hydrochloric acid, water, and brine. The organic phase is dried ($MgSO_4$), and the solvent is evaporated. The product is purified by silica gel chromatography (10% methanol/ethyl acetate) to give 1-[4-methoxybenzenesulfonyl]-pyrrolidine-2(R)-carboxylic acid.

Example 7: N-(t-Butyloxy)-2-[[4-methoxybenzenesulfonyl](benzyl)amino]-2-[2-(4-morpholino)ethyl]acetamide (2.65 g, 5.1 mmol) is dissolved in methylene chloride (30.0 mL) and ethanol (1.0 mL) in a glass sealed tube, and the reaction is cooled to 0° C. Hydrochloric acid gas (from a lecture bottle) is bubbled through the solution for 20 minutes, and then the tube is sealed and kept at room temperature for 3 days. After that time, the solvent is removed, and the reaction is partitioned between ethyl acetate and saturated sodium bicarbonate. The organic phase is dried ($Na_2SO_4$), and the solvent is evaporated. The product is purified by silica gel chromatography (2% methanol/methylene chloride) to give N-hydroxy-2-[[4-methoxybenzenesulfonyl](benzyl)amino]-2-[2-(4-morpholino)ethyl]acetamide, m.p. 56°–60° C.

The starting material is prepared as follows:

N-(2-chloroethyl)morpholine hydrochloride (12.0 g) is dissolved in water (200 mL) and made basic with ammonium hydroxide (100.0 mL) to a pH=~11. The aqueous layer is then extracted several times with ether, the combined organic layers are dried ($Na_2SO_4$), and the solvent is evaporated to yield an oil which is used immediately.

Diethyl acetamidomalonate (11.4 g, 57.08 mmol) is added to a freshly prepared solution of sodium ethoxide in ethanol (made from Na (1.32 g, 57.1 mmol) added to ethanol (34.0 mL)), and the reaction is refluxed for 30 minutes. The reaction is then adjusted to 55° C., and potassium iodide (0.14 g, 0.8 mmol) and dimethylformamide (0.2 mL) are added. Finally, the N-(2-chloroethyl)morpholine (8.9 g, 59.6 mmol) prepared above is added in ethanol (14.0 mL), and the reaction is maintained at 55° C. for 24 hours.

The reaction is diluted with ethyl acetate and filtered through Celite to remove salts. The filtrate is evaporated, and then partitioned between ethyl acetate and brine. The organic layer is dried ($Na_2SO_4$), and the solvent is evaporated. The product is purified by silica gel chromatography (first 50% ethyl/acetate, then 5% methanol/methylene chloride) to give diethyl [2-(4-morpholino)ethyl]acetamidomalonate.

Diethyl [2-(4-morpholino)ethyl]acetamidomalonate (8.0 g, 25.6 mmol) is dissolved in ethanol (128.0 mL). Sodium hydroxide (4.55 mL of a 6N aqueous solution, 27.35 mmol) is added, and the reaction is stirred at room temperature for 24 hours. The ethanol is then evaporated, and the residue is diluted up in water, washed several times with ether, and then the aqueous phase is acidified with concentrated hydrochloric acid to pH=~5. The solution is evaporated to dryness, then suspended in toluene (300.0 mL) and refluxed for 3 hours. After cooling to room temperature, the reaction is diluted with chloroform (300.0 mL), and the mixture is filtered through Celite. The filtrate is evaporated to give ethyl 2-(acetamido)-2-[2-(4-morpholino)ethyl]acetate.

Ethyl 2-(acetamido)-2-[2-(4-morpholino)ethyl]acetate (4.2 g, 16.28 mmol) is dissolved in 6N hydrochloric acid (100.0 mL), and the reaction is refluxed for 4.5 hours. The water is then evaporated, and the product is azeotroped dry using toluene to give 2-amino-2-[2-(4-morpholino)ethyl] acetic acid dihydrochloride.

2-Amino-2-[2-(4-morpholino)ethyl]acetic acid dihydrochloride (4.0 g, 15.33 mmol) is dissolved in a solution of methanol (100.0 mL) and acetyl chloride (5.0 mL), and the reaction is refluxed for 24 hours. The solvent is then evaporated to give methyl 2-amino-2-[2-(4-morpholino) ethyl]acetate dihydrochloride.

Methyl 2-amino-2-[2-(4-morpholino)ethyl]acetate dihydrochloride (6.0 g, 21.82 mmol) is dissolved in chloroform (110.0 mL) and triethylamine (9.12 mL, 65.46 mmol). To this solution is added 4-methoxybenzenesulfonyl chloride (4.51 g, 21.82 mmol), and the reaction is refluxed for 4 hours. After cooling, the reaction is diluted with more chloroform, washed with saturated sodium bicarbonate, the organic layer is dried ($Na_2SO_4$), and the solvent is evaporated to give methyl 2-(4-methoxybenzenesulfonyl)amino-2-[2-(4-morpholino)ethyl]acetate.

To a suspension of sodium hydride (1.03 g, 21.5 mmol) in dimethylformamide (108.0 mL), is added methyl 2-(4-methoxybenzenesulfonyl)amino-2-[2-(4-morpholino)ethyl] acetate (8.0 g, 21.5 mmol) in dimethylformamide (10.0 mL). After stirring at room temperature for 30 minutes, benzyl bromide (2.56 mL, 21.5 mmol) is added, and the reaction is stirred overnight at room temperature. The reaction is then partitioned between ethyl acetate and acidic water (pH=~5), the organic layer is dried ($Na_2SO_4$), and the solvent is evaporated. The product is purified by silica gel chromatography (3% methanol/methylene chloride) to give methyl 2-[[4-methoxybenzenesulfonyl](benzyl)amino]-2-[2-(4-morpholino)ethyl]acetate.

Methyl 2-[[4-methoxybenzenesulfonyl](benzyl)amino]-2-[2-(4-morpholino)ethyl]acetate (7.33 g, 15.86 mmol) is dissolved in methanol (80.0 mL). To this solution is added sodium hydroxide (17.5 mL of a 1N aqueous solution, 17.5 mmol), and the reaction is stirred at room temperature for 8 hours. The reaction is then acidified to pH=~3 using 2.5N hydrochloric acid, and then the solvent is evaporated. The residue is suspended in ethanol, the inorganic salts are filtered away, and the filtrate is evaporated to give 2-[[4-methoxybenzenesulfonyl](benzyl)amino]-2-[2-(4-morpholino)ethyl]acetic acid hydrochloride.

2-[[4-Methoxybenzenesulfonyl](benzyl)amino]-2-[2-(4-morpholino)ethyl]acetic acid hydrochloride (4.24 g, 8.75 mmol), 1-hydroxybenzotriazole (1.34 g, 8.75 mmol), 4-methylmorpholine (3.85 mL, 35.02 mmol), and O-t-butylhydroxylamine hydrochloride (1.10 g, 8.75 mmol) are dissolved in methylene chloride (44.0 mL), and the reaction is cooled to 0° C. To this solution is added N-[dimethylaminopropyl]-N'-ethylcarbodiimide hydrochloride (3.35 g, 17.5 mmol), and the reaction is allowed to warm up to room temperature and stir overnight. The reaction is diluted with more methylene chloride, and the organic layer is washed with saturated sodium bicarbonate, brine, dried (MgSO$_4$), and the solvent is evaporated. The product is purified by silica gel chromatography (2% methanol/methylene chloride) to give N-(t-butyloxy)-2-[[4-methoxybenzenesulfonyl]-(benzyl)amino]-2-[2-(4-morpholino)ethyl]acetamide.

Example 8: The following compounds are prepared similarly to example 7:

(a) N-Hydroxy-2-[[4-methoxybenzenesulfonyl](isobutyl)amino]-2-[2-(4-morpholino)ethyl]acetamide, m.p. 62°–64° C., using isobutyl bromide in the alkylation step in place of benzyl bromide.

(b) N-Hydroxy-2-[[4-methoxybenzenesulfonyl](2-picolyl)amino]-2-[2-(4-morpholino)ethyl]acetamide dihydrochloride, m.p. 195°–197° C., using 2-picolyl chloride in the alkylation step in place of benzyl bromide.

(c) N-Hydroxy-2-[[4-methoxybenzenesulfonyl](3-picolyl)amino]-2-[2-(4-morpholino)ethyl]acetamide dihydrochloride, m.p. >210° C., using 3-picolyl chloride in the alkylation step in place of benzyl bromide.

(d) N-Hydroxy-2-[[4-methoxybenzenesulfonyl](2-methylthiazol-4-ylmethyl)amino]-2-[2-(4-morpholino)ethyl]acetamide dihydrochloride, m.p. 180° C, using 4-chloromethyl-2-methylthiazole in the alkylation step in place of benzyl bromide.

(e) N-Hydroxy-2-[[4-methoxybenzenesulfonyl](benzyl)amino]-2-[2-(4-thiomorpholino)ethyl]acetamide, m.p. 50°–52° C., by starting the synthesis with N-(2-chloroethyl)thiomorpholine, and carrying out the subsequent steps as described in example 7.

(f) N-Hydroxy-2-[[4-methoxybenzenesulfonyl](benzyl)amino]-2-[2-methylthiazol-4-ylmethyl]acetamide, m.p. 79°–81° C., by starting the synthesis with 4-chloromethyl-2-methylthiazole hydrochloride, and carrying out the subsequent steps as described in example 7.

(g) N-Hydroxy-2-[[4-methoxybenzenesulfonyl](benzyl)amino]-2-[6-chloropiperonyl]-acetamide, m.p. 70–74° C., by starting the synthesis with 6-chloropiperonyl chloride, and carrying out the subsequent steps as described in example 7.

(h) N-Hydroxy-2-[[4-methoxybenzenesulfonyl](benzyl)amino]-2-[(1-pyrazolyl)methyl]-acetamide, m.p. 130°–131° C., by starting the synthesis with β-pyrazol-1-yl-alanine (prepared following the procedure of J. Am. Chem. Soc., 110, p. 2237 (1988)), and carrying out the subsequent steps as described in example 7.

(i) N-Hydroxy-2-[[4-methoxybenzenesulfonyl](3-picolyl)amino]-2-[3-picolyl]acetamide dihydrochloride, m.p. >220° C., by starting the synthesis with 3-picolyl chloride, and carrying out the subsequent steps as described in example 7, but in addition, using 3-picolyl chloride in the alkylation step in place of benzyl bromide in example 7.

(j) N-Hydroxy-2-[[4-methoxybenzenesulfonyl](benzyl)amino]-2-[(1-methyl-4-imidazolyl)methyl]acetamide hydrochloride, m.p. >200° C., by starting the synthesis with N-τ-methylhistidine dihydrochloride (prepared following the procedure of Recueil, 97, p.293 (1978)), and carrying out the subsequent steps as described in example 7.

(k) N-Hydroxy-2-[[4-methoxybenzenesulfonyl](isobutyl)amino]-2-[(1-methyl-4-imidazolyl)methyl]acetamide hydrochloride, m.p. 194°–195° C., by starting the synthesis with N-τ-methylhistidine dihydrochloride and carrying out the subsequent steps as described in example 7, using isobutyl iodide in the alkylation step in place of benzyl bromide.

(l) N-Hydroxy-2-[[4-methoxybenzenesulfonyl](3-picolyl)amino]-2-[(1-methyl-4-imidazolyl)methyl]acetamide hydrochloride, m.p. >220° C., by starting the synthesis with N-τ-methylhistidine dihydrochloride and carrying out the subsequent steps as described in example 7, using 3-picolyl chloride in the alkylation step in place of benzyl bromide.

(m) N-Hydroxy-2-[[4-methoxybenzenesulfonyl](2-picolyl)amino]-2-[(1-methyl-4-imidazolyl)methyl]acetamide hydrochloride, m.p. 162°–164° C., by starting the synthesis with N-τ-methylhistidine dihydrochloride and carrying out the subsequent steps as described in example 7, using 2-picolyl chloride in the alkylation step in place of benzyl bromide.

(n) N-hydroxy-2-[[4-methoxybenzenesulfonyl](2-methylthiazol-4-ylmethyl)amino]-2-[(1-methyl-4-imidazolyl)methyl]acetamide hydrochloride, m.p. 160°–163° C., by starting the synthesis with N-τ-methylhistidine dihydrochloride and carrying out the subsequent steps as described in example 7, using 4-chloromethyl-2-methylthiazole in the alkylation step in place of benzyl bromide.

(o) N-hydroxy-2-[[4-methoxybenzenesulfonyl](piperonyl)amino]-2-[(1-methyl-4-imidazolyl)methyl]acetamide hydrochloride, m.p. 195° C., by starting the synthesis with N-τ-methylhistidine dihydrochloride and carrying out the subsequent steps as described in example 7, using piperonyl chloride in the alkylation step in place of benzyl bromide.

Example 9: (a) Methyl 2-[[4-methoxybenzenesulfonyl](benzyl)amino]propionate (2.1 g, 6.01 mmol) is dissolved in methanol (20.0 mL). To this solution is added hydroxylamine hydrochloride (0.84 g, 12.0 mmol), followed by the addition of sodium methoxide (7.0 mL of a 4.37M solution). The reaction is stirred overnight at room temperature. The reaction is worked up by first removing all the solvent, and partitioning between ethyl acetate/hexane (2/1) and saturated sodium bicarbonate. The aqueous phase is extracted well with ethyl acetate/hexane, the combined organic layers are dried (MgSO$_4$), and the solvent is evaporated. The product is purified by silica gel chromatography (ethyl acetate) to give N-hydroxy-2-[[4-methoxybenzenesulfonyl](benzyl)amino]propionamide, m.p. 149°–151° C.

The starting material is prepared as follows:

D.L-Alanine (27.0 g, 300.0 mmol) is dissolved in a solution of methanol (100.0 mL) saturated with HCl gas, and the reaction is refluxed for 2 hours. The solvent is then evaporated, and the residue triturated with ethyl acetate to give alanine methyl ester hydrochloride.

Alanine methyl ester hydrochloride (7.0 g, 50.0 mmol) is dissolved in methylene chloride (100.0 mL) and triethylamine (20.0 mL, 143.0 mmol). To this solution is added 4-methoxybenzenesulfonyl chloride (10.3 g, 50.0 mmol), and the reaction is stirred at room temperature briefly. The reaction is made basic with 1N sodium hydroxide, and washed with methylene chloride. The combined organic layers are dried (Na$_2$SO$_4$), and the solvent is evaporated. Hexane is added to the residue and the precipitate is collected to give N-[4-methoxybenzenesulfonyl]-alanine methyl ester.

To a suspension of sodium hydride (0.60 g, 11.0 mmol) in dimethylformamide (20.0 mL), is added N-[4-methoxybenzenesulfonyl]-alanine methyl ester (2.6 g, 10.0 mmol) in dimethylformamide (10.0 mL). After stirring at room temperature for 30 minutes, benzyl bromide (1.22 mL, 10.0 mmol) is added, and the reaction is stirred for two hours at room temperature. The reaction is then partitioned between ether and brine, the organic layer is dried ($Na_2SO_4$), and the solvent is evaporated. The product is purified by silica gel chromatography (20% ether/hexanes) to give methyl 2-[[4-methoxybenzenesulfonyl]-(benzyl)amino]-propionoate.

(b) Similarly prepared is N-hydroxy-2-[[4-methoxybenzenesulfonyl](benzyl)amino]-4-thiomethylbutyramide, m.p. 104°–106° C., by starting the synthesis with D,L-methionine, and carrying out the subsequent steps as described above.

Example 10: A solution of methyl 2-[[4-methoxybenzenesulfonyl](benzyl)amino]-4-(methylsulfonyl)butyrate (900 mg, 2.0 mmol), sodium methoxide previously generated from sodium metal spheres (100.0 mg, 4.5 mmol), and hydroxylamine hydrochloride (280.0 mg, 4.0 mmol) is refluxed for 2 days. The mixture is cooled to room temperature, concentrated in vacuo, diluted with water, acidified with citric acid, and extracted with ethyl acetate. The combined organic extracts are dried ($MgSO_4$) and the solvent is evaporated. The product is purified by silica gel chromatography (ethyl acetate) to give N-hydroxy-2-[[4-methoxybenzenesulfonyl](benzyl)amino]-4-(methylsulfonyl)butyramide, [M+1]=157.

The starting material is prepared as follows:

To a solution of racemic methionine methyl ester (1.98 g, 10.0 mmol) in methylene chloride (25 mL) containing triethylamine (2.0 mL, 14.3 mmol) is added 4-methoxybenzenesulfonyl chloride (2.1 g, 10.2 mmol). After stirring for 2 hours at room temperature, the mixture is diluted with 1N hydrochloric acid. The organic layer is removed and the aqueous layer is extracted with ether. The combined organic layers are washed with brine, dried ($MgSO_4$), and the solvent is evaporated. The concentrated solution is triturated with ether, and the product is collected by filtration to give methyl 2-[[4-methoxybenzenesulfonyl]amino]-4-(thiomethyl) butyrate.

To a solution of methyl 2-[[4-methoxybenzenesulfonyl]amino]-4-(thiomethyl)butyrate (2.1 g, 6.2 mmol) in dimethylformamide (15 mL) containing potassium carbonate (4.0 g, 29.0 mmol) is added benzyl bromide (1.5 mL, 12.6 mmol). The reaction mixture is stirred for 1 hour at room temperature. The mixture is quenched with water and extracted with ether. The organic extracts are washed with brine, dried ($MgSO_4$), and and the solvent is evaporated. The product is purified by silica gel chromatography (30% ethyl acetate/hexanes) to give methyl 2-[[4-methoxybenzenesulfonyl](benzyl)amino]-4-(thiomethyl) butyrate.

A solution of methyl 2-[[4-methoxybenzenesulfonyl](benzyl) amino]-4-(thiomethyl)butyrate (925.0 mg, 2.17 mmol) in 25% peracetic acid (5 mL) is stirred overnight at room temperature. The mixture is concentrated in vacuo, diluted with water, and extracted with ethyl acetate. The combined organic extracts are dried ($MgSO_4$) and the solvent is evaporated to give methyl 2-[[4-methoxybenzenesulfonyl](benzyl)amino]-4-(methylsulfonyl)butyrate.

Example 11: (a) To a solution of 2R-[[(4-methoxybenzene)sulfonyl](benzyl)amino]-propionic acid (1.04 g, 2.98 mmol) in methylene chloride (50 mL) containing dimethylformamide (230 mL, 2.98 mmol) at room temperature is added oxalyl chloride (520 mL, 5.96 mmol) over 5 minutes dropwise. The mixture is stirred for 30 minutes at room temperature, then added to a pre-formed mixture of hydroxylamine hydrochloride (828 mg, 11.92 mmol) and triethylamine (2.5 mL, 17.9 mmol) in tetrohydrofuran (20 mL)/water (1.5 mL) at 0° C. The reaction mixture is stirred for 45 minutes at 0° C. then slowly warmed to room temperature for 15.5 hours. The mixture is acidified with 1N hydrochloric acid and extracted with methylene chloride. The combined organic extracts are washed with brine, dried ($MgSO_4$), and the solvent is evaporated. The crude product is recrystallized from diethyl ether/ethyl acetate (1:1) to give N-hydroxy-2(R)-[[4-methoxybenzenesulfonyl](benzyl)amino]-propionamide, m.p. 127°–129° C.

The starting material is prepared as follows:

To a solution of D-alanine methyl ester hydrochloride (3.0 g, 21.5 mmol) in methanol (10 mL) is added benzaldehyde (2.3 mL, 22.6 mmol). The reaction mixture is stirred at room temperature for 3 hours. The solvent is then evaporated. To the resultant residue is added acetic acid (15 mL) and methanol (1 mL) followed by portionwise addition of sodium cyanoborohydride (1.35 g, 21.5 mmol) at room temperature. The mixture is stirred overnight, and then the solvent is evaporated. The remaining residue is diluted with water (75 mL) and basified with $Na_2CO_3$. The mixture is extracted with ethyl acetate (3×75 mL). The combined organic extracts are washed with brine (50 mL), dried ($Na_2SO_4$), and the solvent is evaporated to give N-benzyl-D-alanine methyl ester.

To a solution of N-benzyl-D-alanine methyl ester (~2 g) in methylene chloride (40 mL) containing triethylamine (2.47 mL, 17.7 mmol) is added 4-methoxybenzenesulfonyl chloride (2.44 g, 11.8 mmol). The reaction mixture is stirred overnight at room temperature. The mixture is acidified with 1N HCl and extracted with methylene chloride. The combined organic extracts are washed with brine, dried ($Na_2SO_4$), and the solvent is evaporated. The crude product is purified by silica gel chromatography (10%→20% ethyl acetate/hexanes) to provide methyl 2(R)-[[4-methoxybenzenesulfonyl]-(benzyl)amino]propionate.

To a solution of methyl 2(R)-[[4-methoxybenzenesulfonyl](benzyl)amino]propionate (1.05 g, 2.89 mmol) in tetrahydrofuran (60 mL) at room temperature is added 1N aqueous sodium hydroxide (8.6 mL, 8.67 mmol). The reaction mixture is stirred for 19 hours at room temperature. The tetrohydrofuran is then evaporated. The remaining residue is acidified with 1N hydrochloric acid and extracted with ethyl acetate. The combined organic extracts are washed with brine, dried ($Na_2SO_4$), and the solvent is evaporated to give 2(R)-[[4-methoxybenzenesulfonyl](benzyl)amino]propionic acid.

(b) Similarly prepared is N-hydroxy-2(R)-[[4-methoxybenzenesulfonyl](benzyl)amino]-2-benzylacetamide, [M+1]=441, by starting with (R)-phenylalanine, and carrying out the previously described steps.

Example 12: (a) To a solution of N-(t-butyloxy)-2(R)-[[4-methoxybenzenesulfonyl(benzyl)amino]-6-(N,N-dimethylamino)-hexamide (2.13 g, 4.21 mmol) in 1,2-dichloroethane (140 mL) is added ethanol (250 mL, 4.21 mmol). The solution is cooled to −10° C. and hydrogen chloride gas is bubbled in for 30 minutes. The reaction mixture is then sealed and allowed to warm to room temperature, stirring for 2 days. At this time point, the reaction mixture is cooled to −10° C. and hydrogen chloride gas is bubbled in for an additional 30 minutes. The reaction mixture is sealed, warmed to room temperature, and stirred for 24 hours. The mixture is reduced in volume by ½ in vacuo and triturated with ether. The mother liquid is removed and the remaining white solid is dried in vacuo to provide N-hydroxy-2(R)-[[4-methoxybenzenesulfonyl](benzyl)amino]-6-(N,N-dimethylamino)-hexanamide hydrochloride salt, m.p. 175°–177° C.

The starting material is prepared as follows:

To a solution of ε-N-CBZ-(R)-lysine methylester hydrochloride (15.0 g, 45.10 mmol) in methylene chloride (250 mL) containing triethylamine (15.72 mL, 112.75 mmol) is added 4- methoxybenzenesulfonyl chloride (10.25 g, 49.61 mmol) at 0° C. The reaction mixture is warmed to room temperature and stirred overnight. The reaction mixture is diluted with methylene chloride and washed with 1N hydrochloric acid. The organic layer is washed with brine, dried ($Na_2SO_4$), and concentrated in vacuo to yield a yellow oil. The product is purified by silica gel chromatography (50% ethyl acetate/hexanes) to give methyl 2(R)-[[4-methoxybenzenesulfonyl]amino]-6-(N-benzylcarbamoyl) hexanoate.

To a solution of methyl 2(R)-[[4-methoxybenzenesulfonyl]amino]-6-(N-benzylcarbamoyl) hexanoate (12.4 g, 26.5 mmol) in dimethylformamide (100 mL) is added potassium carbonate (7.5 g, 52 mmol) and benzyl bromide (3.3 mL, 28.0 mmol), and the reaction is stirred for 24 hours at room temperature. The mixture is partitioned between water and 50% diethyl ether/ethyl acetate. The aqueous layer is removed and extracted with 50% diethyl ether/ethyl acetate. The combined organic layers are washed with brine, dried ($MgSO_4$) and the solvent is evaporated. The crude product is purified by silica gel chromatography (50% ethyl acetate/hexanes) to give methyl 2(R)-[[4-methoxybenzenesulfonyl](benzyl)amino]-6-(N-benzylcarbamoyl) hexanoate.

To a solution of methyl 2(R)-[[4-methoxybenzenesulfonyl](benzyl)amino]-6-(benzylcarbamoyl) hexanoate (8.61 g, 15.53 mmol) in 95% ethanol (150 mL) is added 1N hydrochloric acid (15.5 mL, 15.53 mmol) followed by 10% Pd/C (4.0 g). The reaction mixture is stirred at room temperature under 1 atmosphere of hydrogen gas for 2 hours. The mixture is filtered through Celite and the solvent is evaporated to provide methyl 2(R)-[[4-methoxybenzenesulfonyl](benzyl)amino]-6-aminohexanoate.

To a solution of methyl 2(R)-[[4-methoxybenzenesulfonyl](benzyl)amino]-6-aminohexanoate (5.05 g, 12.02 mmol) in refluxing formic acid (120 mL) containing sodium formate (2.45 g, 36.07 mmol) is added 37% aqueous formaldehyde (2.70 mL, 36.07 mmol). While continuing to reflux the reaction mixture, three more aliquots of 37% aqueous formaldehyde (2.70 mL, 36.07 mmol each aliquot) are added at 10 minute intervals. The mixture is concentrated in vacuo to yield a yellow oil. The crude product is purified by silica gel chromatography (10:1:0.5; ethylacetate/methanol/ammonium hydroxide) to provide methyl 2(R)-[[4-methoxybenzenesulfonyl](benzyl)amino]-6-(N,N-dimethylamino) hexanoate. This procedure is repeated and the combined product is used in the next reaction.

To a solution of methyl 2(R)-[[4-methoxybenzenesulfonyl](benzyl)amino]-6-(N,N-dimethylamino) hexanoate (4.55 g, 10.7 mmol) in tetrahydrofuran (100 mL) is added 1N aqueous lithium hydroxide (20 mL, 20.33 mmol). The reaction mixture is stirred at room temperature overnight. The reaction mixture is directly concentrated to dryness in vacuo to give the lithium salt of 2(R)-[[4-methoxybenzenesulfonyl](benzyl)amino]-6-(N,N-dimethylamino) hexanoic acid.

To a solution of 2(R)-[[4-methoxybenzenesulfonyl](benzyl)amino]-6-(N,N-dimethylamino) hexanoic acid lithium salt (4.42 g, 10.18 mmol) in methylene chloride (100 mL) containing N- methylmorpholine (6.73 mL, 61.06 mmol), 1-hydroxybenzotriazole monohydrate (1.64 g, 10.687 mmol) and O-t-butylhydroxyl amine hydrochloride (1.41 g, 11.20 mmol) is added N-[dimethylaminopropyl]-N'-ethylcarbodiimide hydrochloride (3.90 g, 20.36 mmol) at 0° C. The reaction mixture is allowed to warm to room temperature and stirring is continued overnight. The mixture is diluted with methylene chloride, washed with saturated sodium bicarbonate, then with brine, dried ($Na_2SO_4$) and the solvent is evaporated. The crude product is purified by silica gel chromatography (10:1:0.5 ethyl acetate/methanol/ammonium hydroxide) to provide N-(t-butyloxy)-2(R)-[[4-methoxybenzenesulfonyl](benzyl)amino]-6-(N,N-dimethylamino) hexanamide.

(b) Similarly prepared is N-hydroxy-2-(R)-[[4-methoxybenzenesulfonyl](3-picolyl)amino]-6-(N,N-dimethylamino)-hexanamide dihydrochloride, m .p . 179°–180° C.

The first step is carried out as described above. The alkylation step is carried out as follows:

To a solution of methyl 2(R)-[[4-methoxybenzenesulfonyl]amino]-6-(benzylcarbamoyl) hexanoate (10.48 g, 22.43 mmol) in dimethylformamide (220 mL) at 0° C. is added 3-picolyl chloride hydrochloride (3.86 g, 23.55 mmol) followed by sodium hydride (2.24 g, 56.07 mmol, 60% in oil). The reaction mixture is warmed to room temperature and stirred for 24 hours. The reaction mixture is quenched with water and extracted with ethyl acetate. The combined organic extracts are washed with brine, dried ($Na_2SO_4$), and the solvent is evaporated. The crude product is purified by silica gel chromatography (75% ethyl acetate/hexanes) to provide methyl 2(R)-[[4-methoxybenzenesulfonyl](3-picolyl)amino]-6-(benzylcarbamoyl) hexanoate.

All of the following steps are carried out as described above.

(c) Similarly prepared is N-hydroxy-2(R)-[[4-methoxybenzenesulfonyl](2-picolyl)amino]-6-(N,N-dimethylamino)-hexanamide dihydrochloride, m.p. 134°–136° C., by alkylating with 2-picolyl chloride in the second step and carrying out the subsequent steps as described above.

Example 13: N-(t-Butyloxy)-2(R)-[[4-methoxybenzenesulfonyl](benzyl)amino]-6-[(N,N-dimethylglycyl)amino]hexanamide (2.17 g, 3.86 mmol) is dissolved in dichloroethane (12 mL) containing ethanol (0.22 mL, 3.86 mmol), and the reaction is cooled to –10° C. Hydrochloric acid gas is bubbled through this solution for 30 minutes. The reaction is sealed, warmed to room temperature and stirred for 2 days. The solvent is reduced to ½ volume by evaporating solvent, and triturated with ether. The resulting solid is removed and dried in vacuo to provide N-hydroxy-2(R)-[[4-methoxybenzenesulfonyl](benzyl)amino]-6-[(N,N-dimethylglycyl)amino]hexanamide hydrochloride, m.p. 105°–108° C.

The starting material is prepared as follows:

To a solution of methyl 2(R)-[[4-methoxybenzenesulfonyl](benzyl)amino]-6-amino hexanoate hydrochloride (7.5 g, 16.44 mmol) in methylene chloride (170 mL) is added 1-hydroxybenzotriazole monohydrate (2.64 g, 1726 mmol), N-methylmorpholine (5.44 mL, 49.34 mmol), and N,N-dimethylglycine (1.86 g, 18.08 mmol), and the reaction is cooled to 0° C. N-[dimethylaminopropyl]-N'-ethylcarbodiimide hydrochloride (6.30 g, 32.88 mmol) is added at 0° C. The reaction mixture is warmed to room temperature and stirred overnight. The mixture is diluted with methylene chloride and washed with saturated aqueous sodium bicarbonate, and then with brine. The organic layer is dried ($Na_2SO_4$), filtered, and and the solvent is evaporated. The crude product is purified by silica gel chromatography (10/0.5/0.5 ethyl acetate/methanol/ammonium hydroxide) to provide methyl 2(R)-[[4-methoxybenzenesulfonyl](benzyl)amino]-6-[(N,N-dimethylglycyl)amino]hexanoate (6.04 g).

To a solution of methyl 2(R)-[[4-methoxybenzenesulfonyl](benzyl)amino]-6-[(N,N-dimethylglycyl)amino]hexanoate (3.95 g, 7.82 mmol) in tetrahydrofuran (75 mL) at 0° C. is added 1N lithium hydroxide (15.64 ml, 15.64 mmol). The reaction mixture is warmed to room temperature and stirred overnight. The tetrahydrofuran is removed and the remaining aqueous layer is acidified with 1N hydrochloric acid. The mixture is evaporated to dryness to yield 2(R)-[[4-methoxybenzenesulfonyl](benzyl)amino]-6-[(N,N-dimethylglycyl)amino]hexanoic acid hydrochloride.

To a solution of 2(R)-[[4-methoxybenzenesulfonyl](benzyl)amino]-6-[(N,N-dimethylglycyl)amino]hexanoic acid hydrochloride (4.12 g, 7.82 mmol) in methylene chloride (78 mL) and dimethylformamide (5 mL) is added 1-hydroxybenzotriazole monohydrate (1.26 g, 8.21 mmol), N-methylmorpholine (2.58 ml, 23.45 mmol), and O-t-butyhydroxylamine hydrochloride (1.08 g, 8.60 mmol). The reaction is cooled to 0° C., and N-[dimethylaminopropyl]-N'-ethylcarbodiimide hydrochloride (3.0 g, 15.64 mmol) is added. The reaction mixture is warmed to room temperature and stirred overnight. The mixture is then diluted with methylene chloride and washed with saturated aqueous sodium bicarbonate, and then with brine. The organic layer is dried (Na$_2$SO$_4$), filtered, and and the solvent is evaporated. The crude product is purified by silica gel chromatography (10/0.5/0.5 ethyl acetate/methanol/ammonium hydroxide) to provide N-(t-butyloxy)-2(R)-[[4-methoxybenzenesulfonyl](benzyl)amino]-6-[(N,N-dimethylglycyl)amino]hexanamide.

Example 14: (a) To a solution of 4-[[4-methoxybenzenesulfonyl](benzyl)amino]-4-carboxy-tetrahydrothiopyran (413.0 mg, 1.0 mmol) in methylene chloride (10 mL) containing dimethylformamide (80.0 mg, 1.1 mmol) is added a 2N solution of oxalyl chloride in methylene chloride (1.0 ml, 2.0 mmol) at −10° C. The mixture is allowed to warm to 20° C. for 30 minutes. This mixture is added to a pre-stirred mixture of hydroxylamine hydrochloride (280.0 mg, 4.0 mmol) in tetrahydrofuran (10 ml)/water (1 ml) containing triethylamine (650.0 mg, 6.0 mmol) at 0° C. dropwise. The reaction mixture is allowed to slowly warm to room temperature and stirring is continued for 1.5 days. The reaction is worked up by partitioning between 1N hydrochloric acid and ethyl acetate. The aqueous layer is removed and repeatedly extracted with ethyl acetate. The combined organic layers are dried (Na$_2$SO$_4$) and the solvent is evaporated. The crude product is purified by silica gel chromatography (2% methanol/methylene chloride) to give 4-[N-hydroxy-carbamoyl]-4-[[4-methoxybenzenesulfonyl](benzyl)amino]-tetrahydrothiopyran, m.p. 179°–181° C.

The starting material is prepared as follows:

A solution of tetrahydrothiopyran-4-one (4.64 g, 40.0 mmol) in methanol (10 mL) is added to a mixture of sodium cyanide (2.0 g, 40.0 mmol) and ammonium chloride (2.36 g, 44.0 mmol) in water (8 mL). The reaction mixture is heated to reflux for 14 hours. The mixture is diluted with water, basified with potassium carbonate, and extracted with diethyl ether. The organic extract is dried (MgSO$_4$) and filtered. The solution is acidified with hydrochloric acid saturated with methylene chloride. The resulting precipitate is filtered off providing 4-amino-4-cyano-tetrahydrothiopyran hydrochloride salt.

A solution of 4-amino-4-cyano-tetrahydrothiopyran (5.4 g, 30.3 mmol) in 6N aqueous hydrochloric (250 mL) acid is heated to reflux for 24 hours. The mixture is triturated by addition of methanol/toluene, and filtered. To the crude product, 4-amino-4-carboxy-tetrahydrothiopyran is added 40 ml of methanol followed by careful addition of thionyl chloride (3.0 ml, 41.1 mmol). The reaction mixture is heated to reflux for 12 hours, cooled to room temperature, and concentrated in vacuo to a reduced volume. The remaining mixture is triturated with ethyl acetate/diethyl ether, and the product is collected by filtration, to give 4-amino-4-carbomethoxy-tetrahydrothiopyran hydrochloride.

To a solution of 4-amino-4-carbomethoxy-tetrahydrothiopyran hydrochloride (3.1 g, 15.0 mmol) in methylene chloride (75 mL) containing triethylamine (3.5 g, 330.0 mmol) is added 4-methoxybenzenesulfonyl chloride (4.1 g, 20.0 mmol) at room temperature. The reaction mixture is stirred at room temperature for 18 hours. The mixture is diluted with water and the organic layer is removed. The aqueous layer is extracted with diethyl ether and the organic extracts are washed with brine, dried (MgSO$_4$) and the solvent is evaporated. The product is purified by silica gel chromatography (50% ethylacetate/hexanes) to provide 4-[[4-methoxybenzenesulfonyl]amino]-4-carbomethoxy-tetrahydrothiopyran.

To a solution of 4-[[(4-methoxybenzene)sulfonyl]amino]-4-carbomethoxy-tetrahydrothiopyran (690.0 mg, 2.0 mmol) in dimethylformamide (20 mL) at 0° C. is added sodium hydride (100.0 mg, 2.5 mmol, 60% in oil) and benzyl bromide (0.5ml, 4.2 mmol). The reaction mixture is allowed to warm to room temperature and stirred for 16 hours. The mixture is quenched by addition of water and extracted with 50% ethyl acetate/diethyl ether. The combined organic extracts are dried (MgSO$_4$), filtered, and the solvent is evaporated. The product is purified by silica gel chromatography (50% diethyl ether/hexanes) to provide 4-[[4-methoxybenzenesulfonyl](benzyl)amino]-4-carbomethoxy-tetrahydrothiopyran.

To a solution of 4-[[4-methoxybenzenesulfonyl](benzyl)amino]-4-carbomethoxy-tetrahydrothiopyran (800.0 mg, 1.9 mmol) in methanol (50 mL) is added 1N sodium hydroxide (25 mL). The mixture is heated to reflux for 10 hours, and then solid sodium hydroxide is added (3.0 g, excess) and refluxing is continued for 18 hours. The mixture is concentrated to a volume of approximately 30 mL and acidified with citric acid (pH=5). The mixture is partitioned between ethyl acetate and water. The organic layer is removed, washed with brine, dried (MgSO$_4$), and the solvent is evaporated to give 4-[[4-methoxybenzenesulfonyl](benzyl)amino]-4-carboxytetrahydrothiopyran.

(b) Similarly prepared is 4-[N-hydroxy-carbamoyl]-4-[[4-methoxybenzenesulfonyl]-(benzyl)amino]-tetrahydropyran, m.p. 137°–140° C., by starting with tetrahydropyran-4-one in the first step, and carrying out the subsequent steps as described above.

(c) Similarly prepared is 1-[N-hydroxy-carbamoyl]-1-[[4-methoxybenzenesulfonyl]-(benzyl)amino]-cyclohexane, m.p. 149°–151° C., by using commercially available 1-amino-cyclohexanecarboxylic acid in the second step, and carrying out the subsequent steps as described above.

(d) Similarly prepared is 1-[N-hydroxy-carbamoyl]-1-[[4-methoxybenzenesulfonyl]-(benzyl)amino]-cyclopentane, m.p. 67.0°–68.0° C., by using commercially available 1-aminocyclopentane carboxylic acid in the second step, and carrying out the subsequent steps as described above.

(e) Similarly prepared is 1-[N-hydroxy-carbamoyl]-1-[[4-methoxybenzenesulfonyl](3-picolyl)amino]-cyclohexane, m.p. 115° C., by using 1-aminocyclohexanecarboxylic acid in the second step, alkylating 1-[carbomethoxy]-1-[[(4-methoxybenzene)sulfonyl]amino]-cyclohexane with 3-picolyl chloride in the third step, and carrying out the other steps as described above.

(f) Similarly prepared is 1-[N-hydroxy-carbamoyl]-1-[[4-methoxybenzenesulfonyl]-(3-picolylamino]-cyclopropane hydrochloride, m.p. 205°–207° C., starting with 1-amino-1-cyclopropanecarboxylic acid.

Example 15:  4-[N-t-Butyloxycarbamoyl]-4-[[4-methoxybenzenesulfonyl](benzyl)amino]-1-[benzyl] piperidine is dissolved in dichloroethane (60 mL) and ethanol (1.0 mL) in a glass sealed tube. Hydrochloric acid gas (from a lecture bottle) is bubbled through the solution for 30 minutes at −10° C. The tube is sealed, gradually warmed to room temperature, and stirred overnight. At this point, hydrochloric acid gas is again bubbled through the reaction mixture as done previously and stirred at room temperature for an additional 24 hours. The reaction mixture is reduced to ⅓ volume in vacuo and triturated with diethyl ether. The solid is filtered off and dried in vacuo to provide 4-[N-hydroxy-carbamoyl]-4-[[4-methoxybenzenesulfonyl](benzyl)amino]-1-[benzyl]-piperidine, m.p. 135.5°–142° C.

The starting material is prepared as follows:

A mixture of N-carboethoxy-4-piperidone (88.6 g, 517.2 mmol), sodium cyanide (30.0 g, 612.1 mmol) in water (54 mL), ammonium chloride (34.0 g, 635.5 mmol) in water (72 mL), and ammonium hydroxide (76 ml) is heated to 60°–65° C. for 5 hours, and then stirred at room temperature overnight. The resulting solid is filtered off, dissolved in methylene chloride, and washed with a small amount of brine. The organic layer is dried (MgSO₄), concentrated in vacuo to ½ volume, and triturated with hexane. The resulting precipate is collected by filtration and dried under vacuum, to give N-carboethoxy-4-amino-4-cyanopiperidine.

A solution of N-carboethoxy-4-amino-4-cyanopiperidine (82.0 g) in water (700 mL) containing concentrated hydrochloric acid (800 mL) is stirred at room temperature for 4 days. The solvent is then evaporated to give 4-amino-4-carboxypiperidine dihydrochloride.

Into a heterogeneous mixture of 4-amino-4-carboxypiperidine dihydrochloride (61.0 g, 0.34 mmol) in methanol (600 mL) is bubbled hydrogen chloride gas at room temperature. The reaction mixture is concentrated to dryness in vacuo, dissolved in 1,4-dioxane (200 mL), and concentrated in vacuo. The residue is redissolved in methanol (1600 mL) into which hydrogen chloride gas is bubbled for 45 minutes. The reaction mixture is refluxed for 18 hours. Most of the solvent is then evaporated, the product is collected by filtration, and washed with ethyl acetate to give 4-amino-4-carbomethoxypiperidine dihydrochloride.

To a mixture of 4-amino-4-carbomethoxypiperidine dihydrochloride (6.60 g, 28.7 mmol) and potassium carbonate (18.8 g, 143.5 mmol) in dioxane/water (350 ml/176 ml) at 0° C. is added di-t-butyl-dicarbonate (8.14 g, 37.31 mmol) in dioxane (60 mL) over 2 hours. The reaction mixture is warmed to room temperature and stirred for 8 hours. To this mixture is added a solution of 4-methoxybenzenesulfonyl chloride (7.71 g, 37.31 mmol) in dioxane (60 mL) at 0° C. The reaction mixture is stirred at room temperature overnight. An additional portion of 4-methoxybenzenesulfonyl chloride (7.71 g, 37.31 mmol) in dioxane (60 mL) is added to the mixture at 0° C. The reaction mixture is allowed to warm to room temperature and stirred overnight. The mixture is concentrated in vacuo, diluted with water, and extracted with ethyl acetate. The aqueous layer is removed, saturated with sodium chloride, and re-extracted with ethyl acetate. The combined extracts are dried (MgSO₄), and the solvent is evaporated. The crude product is purified by silica gel chromatography (50% ethylacetate/hexane) to provide 4-[[4-methoxybenzenesulfonyl]-amino]-1-[(t-butoxycarbonyl]-4-[carbomethoxy]-piperidine, contaminated with a small amount of 4-methoxybenzene-sulfonic acid.

To a solution of 4-[[4-methoxybenzenesulfonyl]amino]-1-[(t-butoxycarbonyl]-4-[carbomethoxy]-piperidine (4.0 g, 9.30 mmol) in dimethylformamide (150 mL) at 0° C. is added sodium hydride (1.12 g, 28.0 ml, 60% in oil) followed by benzyl bromide (4.8 g, 28.0 mmol). The reaction mixture is allowed to warm to room temperature for 1 hour. The mixture is quenched with water and extracted with diethyl ether. The organic extract is dried (MgSO₄) and the solvent is evaporated. The crude product is purified by silica gel chromatography (50% ethyl acetate/hexanes) to provide 4-[[4-methoxybenzenesulfonyl]-(benzyl)amino]-1-[(t-butoxycarbonyl]-4-[carbomethoxy]piperidine.

To a solution of 4-[[4-methoxybenzenesulfonyl](benzyl)amino]- 1-[(t-butoxycarbonyl]-4-[carbomethoxy]-piperidine (1.8 g, 3.47 mmol) in ethyl acetate (10 mL) is added a hydrogen chloride gas saturated methylene chloride solution (15 mL). The reaction mixture is stirred for 4 hours at room temperature. The mixture is concentrated in vacuo to give 4-[[4-methoxybenzenesulfonyl](benzyl)amino]-4-[carbomethoxy]-piperidine.

To a solution of 4-[[4-methoxybenzenesulfonyl](benzyl) amino]-4-[carbomethoxy]-piperidine (1.0 g, 2.39 mmol) in dimethylformamide (160 mL) is added sodium hydride (287.0 mg, 7.18 mmol, 60% in oil) at 0° C., followed by benzyl bromide (450.0 mg, 2.63 mmol). The reaction mixture is slowly warmed to room temperature and stirred overnight. The mixture is quenched with water and extracted with ethyl acetate. The combined organic layers are washed with brine, dried (Na₂SO₄) and the solvent is evaporated to give 4-[[4-methoxybenzenesulfonyl](benzyl)amino]-1-[benzyl]-4-[carbomethoxy]-piperidine.

A heterogeneous mixture of 4-[[4-methoxybenzenesulfonyl](benzyl)amino]-1-[benzyl]-4-[carbomethoxy]-piperidine (1.2 g, 2.26 mmol) in 50% aqueous sodium hydroxide (10 mL) and methanol (50 mL) is heated to reflux for 16 hours. The methanol is evaporated and the residue is neutralized with 4N hydrochloric acid. The aqueous solution is extracted with ethyl acetate. The combined organic extracts are dried (NaSO₄) and the solvent is evaporated to give 4-[[4-methoxybenzenesulfonyl] (benzyl)amino]-1-[benzyl]-4-[carboxy]-piperidine.

To a mixture of 4-[[4-methoxybenzenesulfonyl](benzyl) amino]-1-[benzyl]-4-[carboxy]-piperidine (850.0 mg, 1.64 mmol) in methylene chloride (100 mL) containing N-methylmorpholine (0.6 ml, 5.48 mmol) and O-t-butylhydroxyl amine hydrochloride (620.0 mg, 4.94 mmol) is added N-[dimethylaminopropyl]-N'-ethylcarbodiimide hydrochloride (1.1 g, 5.74 mmol). The reaction mixture is stirred overnight at room temperature. The mixture is diluted with water and extracted with methylene chloride.

The combined organic extracts are dried (Na₂SO₄) and the solvent is evaporated. The crude product is purified by silica gel chromatography (ethyl acetate) to provide 4-[N-t-butyloxy-carbamoyl]-4-[[4-methoxybenzenesulfonyl] (benzyl)amino]-1-[benzyl]-piperidine.

Alternately, 4-[[4-methoxybenzenesulfonyl]amino]-1-[(t-butoxycarbonyl]-4-carbomethoxy]-piperidine is first hydrolyzed with sodium hydroxide to 4-[[4-methoxybenzenesulfonyl]amino]-1-[(t-butoxycarbonyl]-4-[carboxy]-piperidine. Treatment with O-t-butylhydroxylamine under conditions described above gives 4-[N-t-butyloxy-carbamoyl]-4-[[4-methoxybenzenesulfonyl](benzyl)amino]-1-[t-butoxycarbonyl]-piperidine. Reaction with 1N hydrochloric acid in ethyl acetate yields 4-[N-t-butyloxy-carbamoyl]-4-[[4-methoxybenzenesulfonyl](benzyl)amino]-piperidine, which is treated with benzyl bromide as described above.

Similarly prepared, starting from 4-[[4-methoxybenzenesulfonyl(benzyl)amino]-4-[carbomethoxy]-piperidine, are the following:

(a) 4-[N-Hydroxy-carbamoyl]-4-[[4-methoxybenzenesulfonyl](benzyl)-amino]-1-[dimethylaminoacetyl]-piperidine hydrochloride, m.p. 145° C.;

(b) 4-[N-Hydroxy-carbamoyl]-4-[[4-methoxybenzenesulfonyl(benzyl)-amino]-1-[3-picolyl]-piperidine dihydrochloride, m.p. 167° C.;

(c) 4-[N-Hydroxy-carbamoyl]-4-[[4-methoxybenzenesulfonyl](benzyl)-amino]-1-[[carbomethoxymethyl]-piperidine hydrochloride, m.p. 183.5°–185° C.;

(d) 4-[N-Hydroxy-carbamoyl]-4-[[4-methoxybenzenesulfonyl](benzyl)-amino]-piperidine trifluoroacetate;

(e) 4-[N-Hydroxy-carbamoyl]-4-[[4-methoxybenzenesulfonyl](benzyl)-amino]-1-[t-butoxycarbonyl]-piperidine;

(f) 4-[N-Hydroxycarbamoyl]-4-[[4-methoxybenzenesulfonyl](benzyl)-amino]-1-[methylsulfonyl]-piperidine;

(g) 4-[N-Hydroxycarbamoyl]-4-[[4-methoxybenzenesulfonyl](benzyl)amino]-1-[methyl]piperidine hydrochloride, m.p. 185.5°–187° C.;

(h) 4-[N-Hydroxycarbamoyl]-4-[[methoxybenzenesulfonyl](benzyl)amino]-1-[morpholinocarbonyl]piperidine, m.p. 89°–91° C.;

(i) 4-[N-Hydroxycarbamoyl]-4-[[4-methoxybenzenesulfonyl](benzyl)amino]-1-[4-picolyl]piperidine dihydrochloride, m.p. 168° C.

Example 16: Ethyl 2-[[4-methoxybenzenesulfonyl](benzyl)amino]acetate (11.20 g, 30.9 mmol) is dissolved in methanol (100 mL). To this solution is added hydroxylamine hydrochloride (4.31 g, 62.0 mmol), followed by the addition of sodium methoxide, freshly prepared from sodium (2.14 g, 93.0 mmol) dissolved in methanol (55 mL). The reaction is stirred overnight at room temperature. The reaction is worked up by partitioning between dilute hydrochloric acid (pH=~3) and ethyl acetate. The aqueous phase is extracted well with ethyl acetate, the combined organic layers are dried (Na$_2$SO$_4$), and the solvent is evaporated. The product is purified by silica gel chromatography (75% ethyl acetate/hexane) to give N-hydroxy-2-[[4-methoxybenzenesulfonyl](benzyl)amino]-acetamide, m.p. 112°–114° C.

The starting material is prepared as follows:

Benzylamine (16.0 mL, 145.2 mmol) is dissolved in chloroform (110 mL), and the solution is cooled to 0° C. To this solution is added 4-methoxybenzenesulfonyl chloride (10.0 g, 48.4 mmol). The reaction is stirred at room temperature for 1 hour, and then refluxed for 1 hour. After cooling back to room temperature, the reaction is washed three times with 4N hydrochloric acid (200 mL), twice with water (100 mL), once with brine (50 mL), then dried (Na$_2$SO$_4$), and the solvent is evaporated to give N-[4-methoxybenzenesulfonyl]-benzylamine.

Sodium hydride (1.56 g of a 50% oil dispersion, 33.0 mmol) is suspended in tetrahydrofuran (85 mL). To this is added a solution of N-[4-methoxybenzenesulfonyl]-benzylamine (9.0 g, 32.5 mmol) also in tetrahydrofuran (85 mL), and the reaction is stirred for 30 minutes at room temperature. Then ethyl bromoacetate (5.40 mL, 48.8 mmol) is added, and the reaction is stirred overnight at room temperature. The reaction is quenched with a small amount of water, and all the solvent is removed. The crude mixture is partitioned between ethyl acetate and water, the aqueous phase is extracted several times with ethyl acetate, the combined organic layers are dried (Na$_2$SO$_4$), and the solvent is evaporated. The product is purified by silica gel chromatography (30% ethyl acetate/hexane) to give ethyl 2-[[4-methoxybenzenesulfonyl](benzyl)amino]acetate.

Example 17: The following compounds are prepared similarly to Example 16:

(a) N-Hydroxy-2-[[4-methoxybenzenesulfonyl](isobutyl)amino]acetamide, m.p. 133°–134° C., by coupling isobutylamine with 4-methoxybenzenesulfonyl chloride in the first step, and carrying out the subsequent steps as described in example 16.

(b) N-Hydroxy-2-[[4-methoxybenzenesulfonyl](cyclohexylmethyl)amino]acetamide, m.p. 145°–146° C., by coupling cyclohexanemethylamine with 4-methoxybenzenesulfonyl chloride in the first step, and carrying out the subsequent steps as described in example 16.

(c) N-Hydroxy-2-[[4-methoxybenzenesulfonyl](cyclohexyl)amino]acetamide, m.p. 148°–149° C., by coupling cyclohexylamine with 4-methoxybenzenesulfonyl chloride in the first step, and carrying out the subsequent steps as described in example 16.

(d) N-Hydroxy-2-[[4-methoxybenzenesulfonyl](phenethyl)amino]acetamide, m.p. 137°–138° C., by coupling phenethylamine with 4-methoxybenzenesulfonyl chloride in the first step, and carrying out the subsequent steps as described in example 16.

(e) N-Hydroxy-2-[[4-methoxybenzenesulfonyl](3-methylbutyl)amino]acetamide, m.p. 108° C., by coupling 1-amino-3-methylbutane with 4-methoxybenzenesulfonyl chloride in the first step, and carrying out the subsequent steps as described in example 16.

(f) N-Hydroxy-2-[[4-methoxybenzenesulfonyl](sec-butyl)amino]acetamide, m.p. 138° C., by coupling (sec)-butylamine with 4-methoxybenzenesulfonyl chloride in the first step, and carrying out the subsequent steps as described in example 16.

(g) N-Hydroxy-2-[[4-methoxybenzenesulfonyl](tert-butyl)amino]acetamide, m.p. 150°–151° C., by coupling (tert)-butylamine with 4-methoxybenzenesulfonyl chloride in the fast step, and carrying out the subsequent steps as described in example 16.

(h) N-Hydroxy-2-[[4-methoxybenzenesulfonyl](4-fluorobenzyl)amino]acetamide, m.p. 115°–119° C., by coupling 4-fluorobenzylamine with 4-methoxybenzenesulfonyl chloride in the first step, and carrying out the subsequent steps as described in example 16.

(i) N-Hydroxy-2-[[4-methoxybenzenesulfonyl](4-chlorobenzyl)amino]acetamide, m.p. 121°–123° C., by coupling 4-chlorobenzylamine with 4-methoxybenzenesulfonyl chloride in the first step, and carrying out the subsequent steps as described in example 16.

(j) N-Hydroxy-2-[[4-methoxybenzenesulfonyl](isopropyl)amino]acetamide, m.p. 139°–141° C., by coupling isopropylamine with 4-methoxybenzenesulfonyl chloride in the fast step, and carrying out the subsequent steps as described in example 16.

(k) N-Hydroxy-2-[[4-methoxybenzenesulfonyl](4-methylbenzyl)amino]acetamide, m.p. 133°–135° C., by coupling 4-methylbenzylamine with 4-methoxybenzenesulfonyl chloride in the first step, and carrying out the subsequent steps as described in example 16.

(l) N-Hydroxy-2-[[4-methoxybenzenesulfonyl](3-phenyl-1-propyl)amino]acetamide by coupling 3-phenyl-1-propylamine with 4-methoxybenzenesulfonyl chloride in the first step, and carrying out the subsequent steps as described in example 16.

(m) N-Hydroxy-2-[[4-methoxybenzenesulfonyl](4-phenylbutyl)amino]acetamide, m.p. 109°–112° C., by coupling 4-phenylbutylamine with 4-methoxybenzenesulfonyl chloride in the first step, and carrying out the subsequent steps as described in example 16.

(n) N-Hydroxy-2-[[4-methoxybenzenesulfonyl](2-cyclohexylethyl)amino]acetamide, m.p. 143°–144° C., by coupling 2-cyclohexylethylamine with 4-methoxybenzenesulfonyl chloride in the first step, and carrying out the subsequent steps as described in example 16.

(o) N-Hydroxy-2-[[4-methoxybenzenesulfonyl](4-phenylbenzyl)amino]acetamide by coupling 4-phenylbenzylamine with 4-methoxybenzenesulfonyl chloride in the first step, and carrying out the subsequent steps as described in example 16.

(p) N-Hydroxy-2-[[4-methoxybenzenesulfonyl](2,2,2-trifluoroethyl)amino]acetamide, m.p. 142–143° C., by coupling 2,2,2-trifluoroethylamine with 4-methoxybenzenesulfonyl chloride in the first step, and carrying out the subsequent steps as described in example 16.

(q) N-Hydroxy-2- [[benzenesulfonyl](isobutyl)amino]acetamide, m.p. 130°–131 ° C., by coupling isobutylamine with benzenesulfonyl chloride in the first step, and carrying out the subsequent steps as described in example 16.

(r) N-Hydroxy-2-[[4-trifluoromethylbenzenesulfonyl](isobutyl)amino]acetamide, m.p. 130°–131 ° C., by coupling isobutylamine with 4-trifluoromethylbenzenesulfonyl chloride in the first step, and carrying out the subsequent steps as described in example 16.

(s) N-Hydroxy-2-[[4-chlorobenzenesulfonyl](isobutyl) amino]acetamide, m.p. 126°–127° C., by coupling isobutylamine with 4-chlorobenzenesulfonyl chloride in the first step, and carrying out the subsequent steps as described in example 16.

(t) N-Hydroxy-2-[[4-methylbenzenesulfonyl](isobutyl) amino]acetamide, m.p. 138°–140° C., by coupling isobutylamine with 4-methylbenzenesulfonyl chloride in the first step, and carrying out the subsequent steps as described in example 16.

(u) N-Hydroxy-2-[[4-fluorobenzenesulfonyl](isobutyl) amino]acetamide, m.p. 144°–146° C., by coupling isobutylamine with 4-fluorobenzenesulfonyl chloride in the first step, and carrying out the subsequent steps as described in example 16.

(v) N-Hydroxy-2-[[2-thiophenesulfonyl](isobutyl)amino] acetamide by coupling isobutylamine with 2-thiophenesulfonyl chloride in the first step, and carrying out the subsequent steps as described in example 16.

(w) N-Hydroxy-2-[[benzenesulfonyl](benzyl)amino] acetamide, m.p. 90°–93° C., by coupling benzylamine with benzenesulfonyl chloride in the first step, and carrying out the subsequent steps as described in example 16.

(x) N-Hydroxy-2-[[4-nitrobenzenesulfonyl](isobutyl) amino]acetamide, m.p. 128°–130° C., by coupling isobutylamine with 4-nitrobenzenesulfonyl chloride in the first step, and carrying out the subsequent steps as described in example 16.

(y) N-Hydroxy-2-[[4-(tert)-butylbenzenesulfonyl] (isobutyl)amino]acetamide, m.p. 113°–114° C., by coupling isobutylamine with 4-(tert)-butylbenzenesulfonyl chloride in the first step, and carrying out the subsequent steps as described in example 16.

(z) N-Hydroxy-2-[[4-methylsulfonylbenzenesulfonyl] (isobutyl)amino]acetamide, m.p. 159°–161° C., by coupling isobutylamine with 4-methylsulfonylbenzenesulfonyl chloride in the first step, and carrying out the subsequent steps as described in example 16.

(aa) N-Hydroxy-2-[[3-trifluoromethylbenzenesulfonyl] (isobutyl)amino]acetamide, m.p. 140°–141° C., by coupling isobutylamine with 3-trifluoromethylbenzenesulfonyl chloride in the first step, and carrying out the subsequent steps as described in example 16.

(bb) N-Hydroxy-2-[[2,4,6-trimethylbenzenesulfonyl] (isobutyl)amino]acetamide, m.p. 142°–143° C., by coupling isobutylamine with 2,4,6-trimethylbenzenesulfonyl chloride in the first step, and carrying out the subsequent steps as described in example 16.

(cc) N-Hydroxy-2-[[2,5-dimethoxybenzenesulfonyl] (isobutyl)amino]acetamide, m.p. 50°–53° C., by coupling isobutylamine with 2,5-dimethoxybenzenesulfonyl chloride in the first step, and carrying out the subsequent steps as described in example 16.

(dd) N-Hydroxy-2-[[3,4-dimethoxybenzenesulfonyl] (isobutyl)amino]acetamide, m.p. 146°–148° C., by coupling isobutylamine with 3,4-dimethoxybenzenesulfonyl chloride in the first step, and carrying out the subsequent steps as described in example 16.

(ee) N-Hydroxy-2-[[2,4,6-triisopropylbenzenesulfonyl] (isobutyl)amino]acetamide, m.p. 131°–133° C., by coupling isobutylamine with 2,4,6-triisopropylbenzenesulfonyl chloride in the first step, and carrying out the subsequent steps as described above.

(ff) N-Hydroxy-2-[[3,5-dimethylisoxazole-4-sulfonyl (benzyl)amino]acetamide, m.p. 140° C., by coupling benzylamine with 3,5-dimethylisoxazole-4-sulfonyl chloride in the first step, and carrying out the subsequent steps as described in example 16.

(gg) N-Hydroxy-2-[[2,4-dimethylthiazole-5-sulfonyl (benzyl)amino]acetamide, m.p. 55° C., by coupling benzylamine with 2,4-dimethylthiazole-5-sulfonyl chloride in the first step, and carrying out the subsequent steps as described in example 16.

Example 18: Ethyl 2-[[4-methoxybenzenesulfonyl](4-methoxybenzyl)amino]acetate (0.90 g, 2.3 mmol) is dissolved in methanol (20 mL). To this solution is added hydroxylamine hydrochloride (0.80 g, 11.5 mmol), followed by the addition of sodium methoxide (5.2 mL of a 2.67M solution). The reaction is stirred overnight at room temperature. The reaction is worked up by partitioning between dilute hydrochloric acid (pH=~3) and ethyl acetate. The aqueous phase is extracted well with ethyl acetate, the combined organic layers are washed with brine, dried ($Na_2SO_4$), and the solvent is evaporated. The product is recrystallized from ether/ethyl acetate to give N-hydroxy-2-[[4-methoxybenzenesulfonyl]-(4-methoxybenzyl)amino] acetamide, m.p. 134°–135.5° C.

The starting material is prepared as follows:

Glycine ethyl ester hydrochloride (31.39 g, 225.0 mmol) is dissolved in dioxane (150 mL) and water (150 mL), triethylamine (69.0 mL, 495.0 mmol) is added, and the solution is cooled to 0° C. To this solution is added 4-methoxybenzenesulfonyl chloride (51.15 g, 248.0 mmol) over 10 minutes. The reaction is warmed to room temperature and stirred overnight. The next day the mixture is reduced to one-half volume by evaporating solvent, diluted with 1N sodium hydroxide, and extracted well with ether. The combined organic layers are washed with brine, dried ($Na_2SO_4$), and the solvent is evaporated. The product is recrystallized from ether/ethyl acetate/hexanes to give ethyl 2-[[4-methoxybenzenesulfonyl]amino]acetate.

To a suspension of sodium hydride (0.906 g, 22.67 mmol) in dimethylformamide (50.0 mL), is added ethyl 2-[[4-methoxybenzenesulfonyl]amino]acetate (4.13 g, 15.11 mmol) and 4-methoxybenzyl chloride (2.17 mL, 15.87 mmol), and the reaction is stirred overnight at room temperature. The reaction is cooled to 0° C., quenched with 1N hydrochloric acid, and extracted well with ether. The combined organic layers are washed with brine, dried ($Na_2SO_4$), and the solvent is evaporated. The product is recrystallized from ether/hexanes to give ethyl 2-[[4-methoxybenzenesulfonyl](4-methoxybenzyl)amino]acetate.

Example 19: The following compounds are prepared similarly to example 18:

(a) N-Hydroxy-2-[[4-methoxybenzenesulfonyl](2-picolyl)amino]acetamide, m.p. 138.5°–139.5° C., by alkylating ethyl 2-[[4-methoxybenzenesulfonyl]amino]acetate with 2-picolyl chloride in the second step, and carrying out the other steps as described in example 18.

(b) N-Hydroxy-2-[[4-methoxybenzenesulfonyl](3-picolyl)amino]acetamide, m.p. 144°–145° C., by alkylating ethyl 2-[[4-methoxybenzenesulfonyl]amino]acetate with 3-picolyl chloride in the second step, and carrying out the other steps as described in example 18.

(c) N-Hydroxy-2-[[4-methoxybenzenesulfonyl](piperonyl)amino]acetamide, m.p. 143°–144° C., by alkylating ethyl 2-[[4-methoxybenzenesulfonyl]amino]acetate with piperonyl chloride in the second step, and carrying out the other steps as described in example 18.

(d) N-Hydroxy-2-[[4-methoxybenzenesulfonyl](2-piperidinylethyl)amino]acetamide, m.p. 120°–122° C., by alkylating ethyl 2-[[4-methoxybenzenesulfonyl]amino]acetate with N-(2-chloroethyl)-piperidine in the second step, and carrying out the other steps as described in example 18.

Example 20: (a) N-(t-Butyloxy)-2-[[4-methoxybenzenesulfonyl](2-quinolinylmethyl)amino]acetamide (1.15 g, 2.42 mmol) is dissolved in methylene chloride (30.0 mL) and ethanol (0.20 mL) in a glass sealed tube. Hydrochloric acid gas (from a lecture bottle) is bubbled through the solution for 20 minutes, and then the tube is sealed and stands at room temperature overnight. The next day, additional hydrochloric acid gas is bubbled through the solution for 20 minutes, more ethanol (0.20 mL) is added, and then the tube is sealed and stands at room temperature for two days. After that time, the solvent is removed. The product is purified by silca gel chromatography (5% to 15% methanol/methylene chloride with ~1% ammonium hydroxide) to give N-hydroxy-2-[[4-methoxybenzenesulfonyl](2-quinolinylmethyl)amino]acetamide, m.p. 177°–178° C.

The starting material is prepared as follows:

To a suspension of sodium hydride (0.84 g, 35.0 mmol) in dimethylformamide (120.0 mL), is added ethyl 2-[[4-methoxybenzenesulfonyl]amino]acetate (3.19 g, 11.67 mmol) and 2-(chloromethyl)quinoline (2.62 g, 12.26 mmol), and the reaction is stirred for three days at room temperature. Then, additional NaH (0.46 g, 11.67 mmol) is added, and the reaction is heated to 50° C. for 5 hours. The reaction is cooled to 0° C., quenched with water, and extracted well with ether. The combined organic layers are washed with brine, dried ($Na_2SO_4$), and the solvent is removed to give ethyl 2-[[4-methoxybenzenesulfonyl]-(2-quinolinylmethyl)amino]acetate.

Ethyl 2-[[4-methoxybenzenesulfonyl](2-quinolinylmethyl)amino]acetate (4.0g, 9.63 mmol) is dissolved in tetrahydrofuran (70.0 mL). To this solution is added lithium hydroxide (18.0 mL of a 1N aqueous solution, 18.0 mmol), and the reaction is stirred at room temperature overnight. The tetrahydrofuran is evaporated, the reaction is then acidified to pH=~3 using 1N hydrochloric acid, and extracted well with ethyl acetate. The combined organic layers are dried ($Na_2SO_4$), and the solvent is evaporated to give 2-[[4-methoxybenzenesulfonyl](2-quinolinylmethyl)amino]acetic acid hydrochloride. 2-[[4-methoxybenzenesulfonyl](2-quinolinylmethyl)amino]acetic acid hydrochloride (1.49 g, 3.35 mmol), 1-hydroxybenzotriazole (0.539 g, 3.52 mmol), 4-methylmorpholine (1.55 mL, 14.9 mmol), and O-t-butylhydroxyl amine hydrochloride (0.464 g, 3.70 mmol) are dissolved in methylene chloride (50.0 mL), and the reaction is cooled to 0° C. To this solution is added N-[dimethylaminopropyl]-N'-ethylcarbodiimide hydrochloride (1.35 g, 7.04 mmol), and the reaction is allowed to warm up to room temperature and stir overnight. The reaction is diluted with more methylene chloride, and the organic layer is washed with saturated sodium bicarbonate, brine, dried ($MgSO_4$), and the solvent is evaporated. The product is purified by silica gel chromatography (1% methanol/methylene chloride) to give N-(t-butyloxy)-2-[[4-methoxybenzenesulfonyl](2-quinolinylmethyl)amino]acetamide.

(b) Similarly prepared is N-hydroxy-2-[[4-methoxybenzenesulfonyl](4-picolyl)amino]-acetamide hydrochloride, m.p. 193° C., by alkylating ethyl 2-[[4-methoxybenzenesulfonyl]-amino]acetate with 4-picolyl chloride in the second step, and carrying out the other steps as described above.

Example 21: (a) 2-[[4-Methoxybenzenesulfonyl](6-chloropiperonyl)amino]acetic acid (1.87 g, 4.51 mmol) is dissolved in methylene chloride (45.0 mL). To this solution is added oxalyl chloride (0.784 mL, 9.02 mmol) and dimethylformamide (0.35 mL, 4.51 mmol), and the reaction is stirred at room temperature for 60 minutes. Meanwhile, in a separate flask, hydroxylamine hydrochloride (1.25 g, 18.04 mmol) and triethylamine (3.77 mL, 27.06 mmol) are stirred in tetrahydrofuran (20.0 mL) and water (5.0 mL) at 0° C. for 15 minutes. After 60 minutes, the methylene chloride solution is added in one portion to the second flask, and the combined contents are stirred overnight as the flask gradually warms up to room temperature. The reaction is then diluted with acidic water (pH=~3), and extracted several times with ethyl acetate. The combined organic layers are dried ($Na_2SO_4$), and the solvent is evaporated. The product is recrystallized from ethyl acetate/methanol/acetone to give N-hydroxy-2-[[4-methoxybenzenesulfonyl](6-chloropiperonyl)amino]acetamide, m.p. 168°–169° C.

The starting material is prepared as follows:

To a suspension of sodium hydride (1.08 g, 27.06 mmol) in dimethylformamide (180.0 mL), is added ethyl 2-[[4-methoxybenzenesulfonyl]amino]acetate (4.93 g, 18.04 mmol) and 6-chloropiperonyl chloride (3.88 g, 19.0 mmol), and the reaction is stirred overnight at room temperature. The reaction is cooled to 0° C., quenched with 1N hydrochloric acid, and extracted well with ether. The combined organic layers are washed with brine, dried ($Na_2SO_4$), and the solvent is evaporated. The product is recrystallized from ether/hexanes to give ethyl 2-[[4-methoxybenzenesulfonyl](6-chloropiperonyl)amino]acetate.

Ethyl 2-[[4-methoxybenzenesulfonyl](6-chloropiperonyl)amino]acetate (2.12g, 4.79 mmol) is dissolved in tetrahydrofuran (40.0 mL). To this solution is added lithium hydroxide (10.0 mL of a 1N aqueous solution, 10.0 mmol), and the reaction is stirred at room temperature overnight. The tetrahydrofuran is evaporated, the reaction is then acidified to pH=~3 using 1N hydrochloric acid, and extracted well with ethyl acetate. The combined organic layers are dried ($Na_2SO_4$), and the solvent is evaporated to give 2-[[4-methoxybenzenesulfonyl](6- chloropiperonyl) amino]acetic acid.

(b) Similarly prepared is N-hydroxy-2-[[4-methoxybenzenesulfonyl](3,4,5-trimethoxybenzyl)amino] acetamide, m.p. 116°–118° C., by alkylating ethyl 2-[[4-methoxybenzenesulfonyl]amino]acetate with 3,4,5-trimethoxybenzyl chloride in the second step, and carrying out the other steps as described above.

(c) Similarly prepared is N-hydroxy-2-[[4-methoxybenzenesulfonyl](3-methoxybenzyl)amino] acetamide, m.p. 118°–119° C., by alkylating ethyl 2-[[4-methoxybenzenesulfonyl]-amino]acetate with 3-methoxybenzyl chloride in the second step, and carrying out the other steps as described above.

Example 22: Ethyl 2-[[4-methoxybenzenesulfonyl](2-[4-morpholino]ethyl)amino]acetate (7.1 g, 18.4 mmol) is dissolved in ethanol (100 mL), followed by the addition of sodium spheres (1.1 g). To this solution is added hydroxylamine hydrochloride (2.47 g, 35.5 mmol). The reaction is refluxed overnight. The reaction is worked up by removing most of the solvent, and partitioning between saturated sodium bicarbonate and ethyl acetate. The aqueous phase is extracted well with ethyl acetate, the combined organic layers are washed with brine, dried ($MgSO_4$), and the solvent is evaporated. The product is purified by silica gel chromatography (80% ethyl acetate/16% methanol/4% acetic acid). The solvent is removed to give the product containing residual acetic acid. The product is partitioned between ethyl acetate and water (pH=7.1), the organic phase is dried ($MgSO_4$), and the solvent is concentrated and then triturated with ether to give N-hydroxy-2-[[4-methoxybenzenesulfonyl](2-[4-morpholino]ethyl)amino] acetamide, m.p. 108°–112° C.

The starting material is prepared as follows:

Ethyl 2-[[4-methoxybenzenesulfonyl]amino]acetate (13.7 g, 50.0 mmol) is dissolved in ethanol (500 mL), followed by the addition of sodium spheres (2.5 g, 109.0 mmol). To this solution is added N-(2-chloroethyl)morpholine hydrochloride (10.0 g, 53.7 mmol), the reaction is stirred at room temperature for 2 hours, and then refluxed for 1.5 hours. The reaction is partitioned between ethyl acetate and brine. The aqueous phase is extracted well with ethyl acetate, the combined organic layers are dried ($MgSO_4$), and the solvent is evaporated to give ethyl 2-[[4-methoxybenzenesulfonyl] (2-[4-morpholino]amino]-acetate.

Example 23: N-Hydroxy-2-[[4-aminobenzenesulfonyl] (isobutyl)amino]acetamide, m.p. 50°–55° C., is obtained by hydrogenation of N-hydroxy-2-[[4-nitrobenzenesulfonyl]-(isobutyl)amino]acetamide (see example 17x), m.p. 128°–130°, using 10% palladium on carbon.

The starting material is prepared according to example 16 by coupling isobutylamine and 4-nitrobenzenesulfonyl chloride in the first step thereof.

Example 24: N-Hydroxy-2-[[4-dimethylaminobenzenesulfonyl](isobutyl)amino]-acetamide, m.p. 127°–129° C., is obtained by methylation of N-hydroxy-2-[[4-aminobenzenesulfonyl](isobutyl)amino] acetamide using the procedure from Synthesis p. 709, 1987.

Example 25: Ethyl 2-[[4-hexyloxybenzenesulfonyl] (isobutyl)amino]acetate (1.22 g, 3.05 mmol) is dissolved in methanol (15 mL). To this solution is added hydroxylamine hydrochloride (0.43 g, 6.11 mmol), followed by the addition of sodium methoxide, freshly prepared from sodium (0.35 g, 15.3 mmol) dissolved in methanol (5 mL). The reaction is stirred for 36 hours at room temperature. The reaction is worked up by partitioning between dilute hydrochloric acid (pH=~3) and ethyl acetate. The aqueous phase is extracted well with ethyl acetate, the combined organic layers are dried ($Na_2SO_4$), and the solvent is evaporated. The product is crystallized from hexnae/ethyl acetate and collected by filtration to give N-hydroxy-2-[[4-hexyloxybenzenesulfonyl](isobutyl)amino]acetamide, m.p. 108°–110° C.

The starting material is prepared as follows:

A solution of ethanethiol (15 mL) and methylene chloride (15 mL) is cooled to 0° C. Aluminum trichloride (9.62 g, 72.2 mmol) is added (the solution turns green), and the reaction is warmed to room temperature. Ethyl 2-[[4-methoxybenzenesulfonyl](isobutyl)amino]acetate (4.75 g, 14.44 mmol) is added in methylene chloride (5 mL), and the reaction is stirred for 3.5 hours at room temperature. The reaction is then slowly quenched with water, and the crude reaction is partitioned between water and methylene chloride. The aqueous layer is extracted well with methylene chloride, the combined organic layers are dried ($Na_2SO_4$), and the solvent is evaporated. The product is purified by silica gel chromatography (25% to 50% ethyl acetate/ hexane) to give ethyl 2-[[4-hydroxybenzenesulfonyl] (isobutyl)amino]acetate.

Ethyl 2-[[4-hydroxybenzenesulfonyl](isobutyl)amino] acetate (1.0 g, 3.17 mmol) is dissolved in dimethylformamide (16 mL). Cesium carbonate (1.03 g, 3.17 mmol) is added, followed by 1-iodohexane (0.47 mL, 3.17 mmol), and the reaction is stirred overnight at room temperature. The reaction is then partitioned between water and ethyl acetate, the aqueous layer is extracted well with ethyl acetate, the combined organic layers are dried ($Na_2SO_4$), and the solvent is evaporated. The product is purified by silica gel chromatography (10% ethyl acetate/hexane) to give ethyl 2-[[4-hexyloxybenzenesulfonyl](isobutyl)amino] acetate.

Example 26: The following compounds are prepared similarly to example 25:

(a) N-Hydroxy-2-[[4-ethoxybenzenesulfonyl](isobutyl) amino]acetamide, by using ethyl iodide in the cesium carbonate alkylation step, and carrying out the subsequent steps as described in example 25.

(b) N-Hydroxy-2-[[4-butyloxybenzenesulfonyl](isobutyl) amino]acetamide, m.p. 125°–127° C., by using iodobutane in the cesium carbonate alkylation step, and carrying out the subsequent steps as described in example 25.

(c) N-Hydroxy-2-[[4-(3-methyl) butyloxybenzenesulfonyl](isobutyl)amino]acetamide, m.p. 93°–96° C., by using 1-iodo-3-methylbutane in the cesium carbonate alkylation step, and carrying out the subsequent steps as described in example 25.

(d) N-Hydroxy-2-[[4-heptyloxybenzenesulfonyl] (isobutyl)amino]acetamide, m.p. 120°–123° C., by using 1-iodoheptane in the cesium carbonate alkylation step, and carrying out the subsequent steps as described in example 25.

(e) N-Hydroxy-2-[[4-(cyclohexylmethoxy) benzenesulfonyl](isobutyl)amino]acetamide, m.p. 75°–80° C., by using cyclohexylmethyl bromide in the cesium carbonate alkylation step, and carrying out the subsequent steps as described in example 25.

(f) N-Hydroxy-2-[[4-isopropyloxybenzenesulfonyl] (isobutyl)amino]acetamide, m.p. 65°–66° C., by using isopropyl bromide in the cesium carbonate alkylation step, and carrying out the subsequent steps as described in example 25.

(g) N-Hydroxy-2-[[4-ethoxyethoxybenzenesulfonyl] (isobutyl)amino]acetamide, m.p. 111°–114° C., by using 2-bromoethyl ethyl ether in the cesium carbonate alkylation step, and carrying out the subsequent steps as described in example 25.

Example 27: (a) N-(t-butyloxy)-2-[[4-methoxybenzenesulfonyl](benzyl)amino]-2-[(2-methyl-5-tetrazolyl)methyl]acetamide (0.77 g, 1.55 mmol) is dissolved in methylene chloride (2.0 mL) and ethanol (0.1 mL) in a glass sealed tube, and the reaction is cooled to 0° C. Hydrochloric acid gas (from a lecture bottle) is bubbled through the solution for 20 minutes, and then the tube is sealed at room temperature for 3 days. After that time, the solvent is removed, and the reaction is partitioned between ethyl acetate and saturated sodium bicarbonate. The organic phase is dried (Na$_2$SO$_4$), and the solvent is evaporated. The product is purified by silica gel chromatography (2% methanol/methylene chloride) to give N-hydroxy-2-[[4-methoxybenzenesulfonyl](benzyl)amino]-2-[(2-methyl-5-tetrazolyl)methyl]acetamide, m.p. 72°–75° C.

The starting material is prepared as follows:

D-asparagine (13.2 g, 100.0 mmol) is dissolved in dioxane (75.0 mL) and water (125.0 mL), triethylamine (21.0 mL, 150.0 mmol) is added, and the solution is cooled to 0° C. To this solution is added 4-methoxybenzenesulfonyl chloride (22.7 g, 110.0 mmol) over 10 minutes. The reaction is warmed to room temperature and stirred for 3 days. The precipitate is then filtered off, the filtrate is acidified to pH=~4, and extracted well with ethyl acetate. A first crop of pure product precipitates from the ethyl acetate and is collected by filtration. A second crop is obtained by evaporating off the ethyl acetate, and rinsing the solid obtained with water to remove inorganic salts. The two crops are combined to give N-[4-methoxybenzenesulfonyl]-(D)-asparagine.

N-[4-methoxybenzenesulfonyl]-(D)-asparagine (10.1 g, 33.3 mmol) is dissolved in dimethylformamide (167.0 mL). Cesium carbonate (5.43 g, 16.66 mmol) is added, followed by the addition of methyl iodide (2.22 mL, 33.3 mmol), and the reaction is stirred overnight. The reaction is then diluted with saturated ammonium chloride (366.0 mL), and extracted well with ethyl acetate. The combined organic extracts are washed with brine, dried (Na$_2$SO$_4$), and the solvent is evaporated. The crude product is recrystallized from toluene to provide N-[4-methoxybenzenesulfonyl]-(D)-asparagine methyl ester.

To a suspension of N-[4-methoxybenzenesulfonyl]-(D)-asparagine methyl ester (8.54 g, 27.0 mmol) in methylene chloride (47.0 mL) is added pyridine (10.9 mL, 135.0 mmol). Para-toluenesulfonyl chloride (10.3 g, 54.0 mmol) is added, and the reaction mixture is allowed to stand without stirring at room temperature overnight. The next day, saturated sodium bicarbonate is added (125.0 mL), and the mixture is stirred for 1 hour. The mixture is then diluted with water and extracted well with ethyl acetate. The combined organic extracts are washed with brine, dried (Na$_2$SO$_4$), and the solvent is evaporated. The crude product is recrystallized from 20% tetrahydrofuran/methanol to provide methyl 2(R)-[[4-methoxybenzenesulfonyl]amino]-4-cyano-propionate.

To a suspension of sodium hydride (0.93 g, 23.2 mmol) in dimethylformamide (95.0 mL), is added methyl 2(R)-[[4-methoxybenzenesulfonyl]amino]-4-cyano-propionate (6.92 g, 23.2 mmol) in dimethylformamide (10.0 mL). After stirring at room temperature for 20 minutes, benzyl bromide (3.1 mL, 25.5 mmol) is added, and the reaction is stirred overnight at room temperature. The reaction is then partitioned between ethyl acetate and acidic water (pH=~5), the organic layer is dried (Na$_2$SO$_4$), and the solvent is evaporated. The product is purified by silica gel chromatography (40% ethyl acetate/hexane) to give methyl 2(R)-[[4-methoxybenzenesulfonyl](benzyl)amino]-4-cyano-propionate.

To a solution of methyl 2(R)-[[4-methoxybenzenesulfonyl](benzyl)amino]-4-cyanopropionate (1.34 g, 3.47 mmol) in dimethylformamide (5.4 mL) is added triethylamine hydrochloride (0.95 g, 6.93 mmol) and sodium azide (0.45 g, 6.93 mmol). The reaction is stirred at 110° C. overnight. The next day, the solvent is evaporated, the residue is acidified with 1N hydrochloric acid (16.0 mL), and extracted well with ethyl acetate. The combined organic extracts are washed with brine, dried (Na$_2$SO$_4$), and the solvent is evaporated to yield methyl 2(R)-[[4-methoxybenzenesulfonyl](benzyl)amino]-2-[(5-tetrazolyl)methyl]acetate.

This crude tetrazole is dissolved in dimethylformamide (17.4 mL). Cesium carbonate (0.56 g, 1.73 mmol) is added, followed by the addition of methyl iodide (0.23 mL, 3.47 mmol), and the reaction is stirred overnight. The reaction is then diluted with brine and extracted well with ethyl acetate. The combined organic extracts are washed with brine, dried (Na$_2$SO$_4$), and the solvent is evaporated. The product is purified by silica gel chromatography (40% ethyl acetate/hexane) to give separately the two regioisomers: methyl 2(R)-[[4-methoxybenzenesulfonyl](benzyl)amino]-2-[(1-methyl-5-tetrazolyl)methyl]acetate (0.50 g); and methyl 2(R)-[[4-methoxybenzenesulfonyl](benzyl)amino]-2-[(2-methyl-5-tetrazolyl)methyl]acetate.

Methyl 2(R)-[[4-methoxybenzenesulfonyl](benzyl) amino]-2-[(2-methyl-5-tetrazolyl)methyl]acetate (1.0 g, 2.27 mmol) is dissolved in tetrahydrofuran (11.3 mL) and water (11.3 mL). To this solution is added lithium hydroxide hydrate (0.095 g, 2.27 mmol), and the reaction is stirred at room temperature for 2 hours. The reaction is then acidified to pH=~3 using 1N hydrochloric acid, and extracted well with ethyl acetate. The combined organic extracts are washed with brine, dried (Na$_2$SO$_4$), and the solvent is evaporated to provide 2(R)-[[4-methoxybenzenesulfonyl] (benzyl)amino]-2-[(2-methyl-5-tetrazolyl)methyl]acetic acid (0.96 g).

2(R)-[[4-methoxybenzenesulfonyl](benzyl)amino]-2-[(2-methyl-5-tetrazolyl)methyl]acetic acid (0.96 g, 2.24 mmol), 1-hydroxybenzotriazole (0.30 g, 2.24 mmol), 4-methylmorpholine (0.86 mL, 7.89 mmol), and O-t-butylhydroxylamine hydrochloride (0.30 g, 2.24 mmol) are dissolved in methylene chloride (75.0 mL). N-[dimethylaminopropyl]-N'-ethylcarbodiimide hydrochloride (0.86 g, 4.48 mmol) is added, and the reaction is stirred overnight. The reaction is then diluted with water and extracted with methylene chloride. The combined organic extracts are washed with brine, dried (Na$_2$SO$_4$), and the solvent is evaporated. The crude product is purified by silica gel chromatography (50% ethyl acetate/hexane) to give N-(t-butyloxy)-2-[[4-methoxybenzenesulfonyl](benzyl) amino]-2-[(2-methyl-5-tetrazolyl)methyl]acetamide.

(b) Similarly prepared is the other tetrazole regioisomer, N-hydroxy-2-[[4-methoxybenzenesulfonyl](benzyl)amino]-2-[(1-methyl-5-tetrazolyl)methyl]acetamide, m.p. 92°–96° C., by completing the synthesis as described above.

(c) Similarly prepared is N-hydroxy-2-[[4-methoxybenzenesulfonyl](benzyl)amino]-2-[(5-tetrazolyl) methyl]acetamide, m.p. 91°–94° C., by completing the synthesis as described above, except trityl chloride is used to protect the tetrazole ring in place of methyl iodide.

(d) Similarly prepared is N-hydroxy-2-[[4-methoxybenzenesulfonyl](4-phenylbenzyl)amino]-2-[(5-tetrazolyl)methyl]acetamide, m.p. 184° C., by completing the synthesis as described above, except 4-chloromethylbiphenyl is used in place of benzyl bromide in the alkylation step.

Example 28: Oxalyl chloride (106 mL, 1.22 mol) is added over 1 hour to dimethylformamide (92 mL) in methylene chloride (1250 mL) at 0° C. To this is added a solution of 2(R)-[[4-methoxybenzenesulfonyl](3-picolyl)amino]-3-methylbutanoic acid hydrochloride (248 g, 0.6 mol) in dimethylformamide (450 mL) over 1 hour, maintaining the temperature at 0° C. This solution is stirred an additional 2 hours at room temperature, and then added dropwise to a mixture of hydroxylamine (460 g of a 50% aqueous solution, 6.82 mol) in tetrahydrofuran (2400 mL). The reaction is stirred an additional 3 hours at 5° C., and then at room temperature overnight. The reaction mixture is filtered, the organic layer is collected, and the solvent is evaporated. The crude product is re-dissolved in methylene chloride (2 L), washed with water (2×1 L), saturated sodium bicarbonate (4×1 L), brine (1 L), dried (Na$_2$SO$_4$), and the solvent is evaporated. The product is dissolved in ethyl acetate (700 mL) and diluted with ether (1400 mL) to induce precipitation. The pure product is collected by filtration to provide N-hydroxy-2(R)-[[4-methoxybenzenesulfonyl](3-picolyl)amino]-3-methylbutanamide. After conversion to the hydrochloride salt, a white solid is obtained, m.p. 169°–170° C. (dec).

The starting material is prepared as follows:

To a solution of D-valine (2000 g, 17.09 mol) in water (16.9 L) and acetone (9.5 L), cooled to 5° C., is added triethylamine (4769 mL, 34.22 mol), and the reaction is stirred for 30 minutes. Then a solution of 4-methoxybenzenesulfonyl chloride (3524 g, 18.48 mol) in acetone (7.4 L) is added over 30 minutes, and the reaction is stirred at room temperature overnight. Most of the acetone is evaporated off, and the pH is adjusted to pH=8.25 with 6N sodium hydroxide. The crude product is washed with toluene (2×10 L), and then the pH is re-adjusted to pH=2.2 with 6N hydrochloric acid. The mixture is then extracted with methylene chloride (3×12 L), the combined organic layers are washed with 2N hydrochloric acid, water, dried (Na$_2$SO$_4$), and the solvent is evaporated to provide N-[4-methoxybenzenesulfonyl]-(D)-valine.

To a solution of N-[4-methoxybenzenesulfonyl]-(D)-valine (8369 g, 29.13 mol) in methanol (30 L) at 5° C. is added thionyl chloride (2176 mL, 29.7 mol) over 2.5 hours. After stirring for 3 hours at 5° C., the reaction is stirred for 36 hours at room temperature. Most of the solvent is evaporated, and the crude product is dissolved in toluene (80 L). The toluene layer is then washed with water (20 L), saturated sodium bicarbonate (20 L), water again (20 L), 2N hydrochloric acid (20 L), brine (20 L), dried (Na$_2$SO$_4$), and the solvent is evaporated. The solid obtained is dissolved in ethyl acetate (8 L) and heptane (16 L) is added to induce crystallization. The precipitated product is collected by filtration to provide methyl 2(R)-[[4-methoxybenzenesulfonyl]amino]-3-methylbutanoate.

To a solution of methyl 2(R)-[[4-methoxybenzenesulfonyl]amino]-3-methylbutanoate (1662 g, 5.52 mol) in dimethylformamide (10.9 L) is added 3-picolyl chloride hydrochloride (947.3 g, 5.77 mol) followed by powdered potassium carbonate (2409.9 g, 17.36 mol). The reaction mixture is stirred at room temperature for 2 days. At that time, additional quantities of 3-picolyl chloride hydrochloride (95 g) and powdered potassium carbonate (241 g) are added, and the reaction is stirred for 3 more days. The solids are then filtered away, the crude product is poured into water (22 L), and the pH is adjusted to pH=8 with 6N sodium hydroxide. This solution is extracted well with toluene (4×10 L), the combined organic layers are washed with water (2×12 L), and then with 6N hydrochloric acid (3×1600 mL). This aqueous layer is then re-adjusted to pH=8 with 6N sodium hydroxide, extracted with toluene (4×10 L), dried (Na$_2$SO$_4$), and the solvent is evaporated. The oil obtained is re-dissolved in ethyl acetate (12 L), cooled to 5° C., and to this is added methanolic HCl (834 mL). After stirring for 2 hours, the precipitated product is collected by filtration to give methyl 2(R)-[[4-methoxybenzenesulfonyl](3-picolyl)amino]-3-methylbutanoate hydrochloride.

Methyl 2(R)-[[4-methoxybenzenesulfonyl](3-picolyl)amino]-3-methylbutanoate hydrochloride (7164 g, 16.7 mol) is added to a solution of water (27 L) and concentrated hydrochloric acid (9 L), and heated to 120° C. for 3 days. After cooling down to room temperature, charcoal (350 g) is added, stirring is continued for 45 minutes, the reaction is filtered, and the solvent is evaporated. The crude solid is re-dissolved in methanol (7.1 L) and ethyl acetate (73 L), and cooled to 3° C. for 2 hours. The precipitated product is collected by filtration to give 2(R)-[[4-methoxybenzenesulfonyl](3-picolyl)amino]-3-methylbutanoic acid hydrochloride.

Example 29: N-Benzyloxy-2(R)-[[4-methoxybenzenesulfonyl](3-picolyl)amino]-3-methylbutanamide (see example 29a) is reacted with hydrogen in the presence of 10% palladium on charcoal catalyst at room temperature and atmospheric pressure to yield N-hydroxy-2(R)-[[4-methoxybenzenesulfonyl](3-picolyl)amino]-3-methylbutanamide. After conversion to the hydrochloride salt, a white solid is obtained, m.p. 169°–170° C. (dec).

(a) The N-(benzyloxy) substituted prodrug derivative of the above compound is prepared as follows:

2(R)-[[4-methoxybenzenesulfonyl](3-picolyl)amino]-3-methylbutanoic acid hydrochloride is reacted with O-benzylhydroxylamine hydrochloride under conditions described for reaction with O-t-butylhydroxylamine hydrochloride to yield N-(benzyloxy)-2(R)-[[4-methoxybenzenesulfonyl](3-picolyl)amino]-3-methylbutanamide, m.p. 74.5°–76° C.

(b) The corresponding N-(4-methoxybenzyloxy) substituted prodrug derivative, N-(4-methoxybenzyloxy)-2(R)-[[4-methoxybenzenesulfonyl](3-picolyl)amino]-3-methylbutanamide, is prepared as follows:

2(R)-[[4-methoxybenzenesulfonyl](3-picolyl)amino]-3-methylbutanoic acid hydrochloride (2.41 g, 5.82 mmol), 1-hydroxybenzotriazole (0.786 g, 5.82 mmol), 4-methylmorpholine (1.9 mL, 17.46 mmol), and O-(4-methoxybenzyl)hydroxylamine (1.78 g, 11.63 mmol) (prepared according to Pol. J. Chem. 55, 1163–1167 (1981)) are dissolved in methylene chloride (55 mL). N-[dimethylaminopropyl]-N'-ethylcarbodiimide hydrochloride (1.45 g, 7.57 mmol) is added, and the reaction is stirred overnight. The reaction is then diluted with water and extracted with methylene chloride. The combined organic extracts are washed with brine, dried (Na$_2$SO$_4$), and the solvent is evaporated. The crude product is purified by silica gel chromatography (ethyl acetate followed by 5% methanol/ethyl acetate) to give N-(4-methoxybenzyloxy)-2(R)-[[4-methoxybenzenesulfonyl]-(3-picolyl)amino]-3-methylbutanamide, m.p. 45°–53° C.

Similarly prepared are: (c) the N-(2,4-dimethoxybenzyloxy)-substituted prodrug derivative, N-(2,4-dimethoxybenzyloxy)-2(R)-[[4-methoxybenzenesulfonyl](3-picolyl)amino]-3-methyl-butanamide, m.p. 45°–60° C.;

(d) the N-(2-methoxybenzyloxy)-substituted prodrug derivative, N-(2-methoxybenzyloxy)-2(R)-[[4-methoxybenzenesulfonyl](3-picolyl)amino]-3-methyl-butanamide, m.p. 46°–56° C.

Example 30: N-(t-Butyloxy)-2(R)-[[4-methoxybenzenesulfonyl](3-picolyl)amino]- 3(R)-(3-picolyloxy)butanamide (1.3 g, 2.4 mmol) is dissolved in methylene chloride (50 mL) containing ethanol (0.14 mL, 2.4 mmol) in a round bottom flask, and the reaction is cooled to −10° C. Hydrochloric acid gas (from a lecture bottle) is bubbled through for 20 minutes. The reaction is sealed, allowed to slowly warm to room temperature, and stirred for two days. The solvent is reduced to ⅓ the volume by evaporation and the residue is triturated with ether. The mixture is filtered, the filter cake is removed and dried in vacuo to provide N-hydroxy-2(R)-[[4-methoxybenzenesulfonyl](3-picolyl)amino]-3(R)-(3-picolyloxy)-butanamide dihydrochloride as a white solid; $[\alpha]_D^{25}$=+35.26° (c=5.58, DMSO).

The starting material is prepared as follows:

To a solution of D-threonine (5.0 g, 0.042 mol) in water (50 mL) and dioxane (50 mL) containing triethylamine (8.9 mL, 0.063 mol) at room temperature is added 4-methoxybenzenesulfonyl chloride (9.54 g, 0.046 mol). The reaction mixture is stirred overnight at room temperature. Most of the dioxane is evaporated off, and the pH is adjusted to pH=2 with 1N HCl. The mixture is then extracted with ethyl acetate. The combined organic extracts are washed with brine, dried ($Na_2SO_4$), and concentrated in vacuo to provide N-[4-methoxybenzenesulfonyl]-(D)-threonine.

N-[4-methoxybenzenesulfonyl]-(D)-threonine (4.0 g, 13.84 mmol), 1-hydroxybenzotriazole (1.87 g, 13.84 mmol), 4-methylmorpholine (7.9 mL, 69.2 mmol), and O-t-butyl-hydroxylamine hydrochloride (5.22 g, 41.52 mmol) are dissolved in methylene chloride (100 mL). To this solution is added N-[dimethylaminopropyl]-N'-ethylcarbodiimide hydrochloride (3.45 g, 17.99 mmol), and the reaction is stirred overnight. The mixture is then diluted with water and extracted with methylene chloride. The combined organic extracts are washed with brine, dried ($Na_2SO_4$), and concentrated in vacuo. The crude product is purified by silica gel chromatography (ethyl acetate) to give N-(t-butyloxy)-2(R)-[[4-methoxybenzenesulfonyl]-amino]-3(R)-hydroxybutanamide.

To a solution of N-(t-butyloxy)-2(R)-[[4-methoxybenzenesulfonyl]amino]-3(R)-hydroxybutanamide (3.04 g, 8.44 mmol) in dimethylformamide (150 mL) is added 3-picolyl chloride hydrochloride (1.45 g, 8.87 mmol) followed by potassium carbonate (11.65 g, 84.4 mmol). The reaction mixture is stirred at room temperature overnight, then heated to 45° C. for 5 hours. An additional mount of 3-picolyl chloride hydrochloride (692.0 mg, 4.23 mmol) is added at this point. The reaction mixture is stirred at 45° C. for 10 hours. The reaction mixture is diluted with water and extracted with ethyl acetate. The combined organic extracts were washed with brine, dried ($Na_2SO_4$), and concentrated in vacuo. The crude product is purified by silica gel chromatography (ethyl acetate, then 5% methanol/methylene chloride) to give N-(t-butyloxy)-2(R)-[[4-methoxybenzenesulfonyl]-(3-picolyl)amino]-3(R)-(3-picolyloxy)butanamide.

Example 31: (a) N-(t-Butyloxy)-2(R)- [[4-methoxybenzenesulfonyl](4-picolyl)amino]-cyclohexylacetamide (1.9 g, 3.9 mmol) is dissolved in dichloroethane (50 mL) containing ethanol (0.21 ml, 3.9 mmol) in a round bottom flask, and the reaction is cooled to −10° C. Hydrochloric acid gas (from a lecture bottle) is bubbled through for 30 minutes. The reaction is sealed, allowed to slowly warm to room temperature, and stirred for 4 days. The solvent is reduced to ⅓ volume by evaporation and triturated with ether. The mixture is filtered, filter cake removed, and dried in vacuo to provide N-hydroxy-2(R)-[[4-methoxybenzenesulfonyl](4-picolyl)amino]-2-cyclohexylacetamide hydrochloride as a white solid, m.p. 154.5°–156° C.

The starting material is prepared as follows:

To a solution of D-cyclohexylglycine hydrochloride (10.4 g, 53.7 mmol) in 1:1 dioxane/water (200 mL) containing triethylamine (37.0 g, 366.0 mmol) at room temperature is added 4-methoxybenzenesulfonyl chloride (15.0 g, 73.0 mmol), and the reaction mixture is stirred at room temperature overnight. The mixture is then diluted with methylene chloride, washed with 1N aqueous hydrochloric acid and water. The organic layer is washed again with brine, dried ($Na_2SO_4$), and the solvent is evaporated to provide N-[4-methoxybenzenesulfonyl]-(D)-cyclohexylglycine as a crude product. A solution of this crude product in toluene (200 mL) containing N,N-dimethylformamide di-t-butyl acetal (48.5 mL, 200.0 mmol) is heated to 95° C. for 3 hours. The solvent is then evaporated. The crude product is purified by silica gel chromatography (30% ethyl acetate/hexanes) to provide N-[4-methoxybenzenesulfonyl](D)-cyclohexylglycine t-butyl ester.

To a solution of N-[4-methoxybenzenesulfonyl]-(D)-cyclohexylglycine t-butyl ester (2.0 g, 4. 1 mmol) in dimethylformamide (100 mL) is added 4-picolyl chloride hydrochloride (0.74 g, 4.5 mmol) followed by potassium carbonate (5.61 g, 40.7 mmol). The reaction mixture is stirred at room temperature for 4 days. The mixture is then diluted with water and extracted with ethyl acetate. The combined organic extracts are washed with brine, dried ($Na_2SO_4$), and the solvent is evaporated. The crude product is purified by silica gel chromatography (ethyl acetate) to give t-butyl 2(R)-[[4-methoxybenzenesulfonyl]-(4-picolyl)amino]-2-cyclohexylacetate.

t-Butyl 2(R)-[[4-methoxybenzenesulfonyl](4-picolyl)amino]-cyclohexylacetate (2.0 g, 4.2 mmol) is dissolved in methylene chloride (80 mL) and cooled to −10° C. Hydrochloric acid gas is bubbled into the solution for 10 minutes. The reaction mixture is then sealed, warmed to room temperature and stirred overnight. The solvent is then evaporated to provide 2(R)-[[4-methoxybenzenesulfonyl](4-picolyl)amino]-2-cyclohexylacetic acid hydrochloride.

2(R)-[[4-Methoxybenzenesulfonyl](4-picolyl)amino]-cyclohexylacetic acid hydrochloride (1.8 g, 4.2 mmol), 1-hydroxybenzotriazole (0.65 g, 4.81 mmol), 4-methylmorpholine (2.4 mL, 24.04 mmol), and O-t-butylhydroxylamine hydrochloride (1.81 g, 14.4 mmol) are dissolved in methylene chloride (100 mL). N-[dimethylaminopropyl]-N'-ethyl-carbodiimide hydrochloride (1.2 g, 6.25 mmol) is added, and the reaction is stirred overnight. The reaction is then diluted with water and extracted with methylene chloride. The combined organic extracts are washed with brine, dried ($Na_2SO_4$), and the solvent is evaporated. The crude product is purified by silica gel chromatography (5% methanol/methylene chloride) to give N-(t-butyloxy)-2(R)-[[4-methoxybenzenesulfonyl]-(4-picolyl)amino]-2-cyclohexylacetamide.

(b) Similarly prepared is N-hydroxy-2(R)-[[4-methoxybenzenesulfonyl](2-(2-pyridyl)ethyl)amino]-2-cyclohexylacetamide, m.p. 131.5°–134.0° C.

The first two steps are carried out as described above. A Mitsunobu step is substituted for the alkylation step as described below.

To a stirring solution of N-[4-methoxybenzenesulfonyl]-(D)-cyclohexylglycine-t-butyl ester (2.0 g, 5.25 mmol) in tetrahydrofuran (50 mL) is added u-iphenylphosphine (4.13 g, 15.75 mmol) and 2-(2-hydroxyethyl)-pyridine (646.0 mg, 5.25 mmol) followed by diethyl azodicarboxylate (2.28 g, 13.1 mmol). The reaction mixture is stirred at room temperature for 48 hours. The mixture is concentrated directly in vacuo. The crude mixture is applied to a column of silica gel (30% ethylacetate/hexane) to provide t-butyl 2(R)-[N-[4-methoxybenzenesulfonyl](2-(2-pyridyl)ethyl)amino]-2-cyclohexylacetate.

All of the subsequent steps are carried out as described under (a).

(c) Similarly prepared is N-hydroxy-2(R)-[[4-methoxybenzenesulfonyl](3-(3-pyridyl)propyl)amino]-2-cyclohexylacetamide, m.p. 136.0°–138° C., by using 3-pyridinepropanol in the Mitsunobu step, and carrying out the subsequent steps as described above.

(d) Similarly prepared is N-hydroxy-2(R)-[[4-methoxybenzenesulfonyl](2-methylpyrid-5-ylmethyl)amino]-2-cyclohexylacetamide, m.p. 156.5°–157.0° C., by using 6-methyl-3-pyridinemethanol (prepared as in J. Org. Chem. 53, 3513 (1988)) in the Mitsunobu step, and carrying out the subsequent steps as described above.

(e) Similarly prepared is N-hydroxy-2(R)-[[4-methoxybenzenesulfonyl](4-tetrahydropyranmethyl)amino]-2-cyclohexylacetamide, m.p. 75.0°–87.0° C., by using 4-(hydroxymethyl)tetrahydropyran (prepared as in Okrytiya. Izobret. 82 (1985)) in the Mitsunoba step, and carrying out the subsequent steps as described above.

Example 32: (a) N-(t-Butyloxy)-2(R)-[(4-methoxybenzenesulfonyl)(benzyl)amino]-2-(4-N-methylpiperidinyl)acetamide (733.0 mg, 1.46 mmol) is dissolved in methylene chloride (60 mL) containing ethanol (67.0 mg, 146 mmol), and the reaction is cooled to −10° C. Hydrochloric acid gas (from a lecture bottle) is bubbled through for 15 minutes. The reaction is sealed, allowed to slowly warm to room temperature, and stirred for 6 days. The solvent is reduced to ⅓ volume by evaporation and triturated with ether. The mixture is filtered, filter cake removed, and dried in vacuo to provide N-hydroxy-2(R)-[(4-methoxybenzenesulfonyl)(benzyl)amino]-2-(4-N-methylpiperidinyl)acetamide hydrochloride as a light tan solid, m.p. >160° C. (dec).

The starting material is prepared as follows:

To a solution of ethyl 4-pyridylacetate (11.17 g, 67.62 mmol) in 2N hydrochloric acid (100 mL) is added platinum (IV) oxide (275 mg). The mixture is shaken in a Parr hydrogenation apparatus for 60 hours under a hydrogen pressure of 50 psi (=3.45 bar). The reaction mixture is basified to pH 8–9 with saturated aqueous sodium carbonate and then washed with methylene chloride. The aqueous layer is concentrated in vacuo providing sodium 4-piperidyl acetate as a white solid. To a solution of the crude product (5.0 g, 30.3 mmol) in 3:1 water/dioxane (200 mL) at 0° C. is added a solution of di-tert-butyldicarbonate (6.38 g, 29.3 mmol) in dioxane (25 mL) in one portion. The cloudy reaction mixture is warmed to room temperature and stirred overnight. The mixture is then filtered, cooled to 0° C. and acidified with cold 6N hydrochloric acid (pH=2–3). This solution is extracted with ethyl acetate. The combined organic layers are dried (Na$_2$SO$_4$), and the solvent is evaporated to provide N-t-BOC-piperidine-4-acetic acid as a white crystalline solid.

To a solution of N-t-BOC-piperidine-4-acetic acid (4.67 g, 19.22 mmol) in tetrahydrofuran at −78° C. is added triethylamine (2.53 g, 24.99 mmol) followed by pivaloyl chloride (2.55 g, 21.14 mmol). The resulting white slurry is stirred at −78° C. for 15 minutes, warmed to 0° C. for 45 minutes, then recooled to −78° C. In a separate flask, (R)-(+)-4-benzyl-2-oxazolidinone (4.09 g, 23.1 mmol) is dissolved in tetrahydrofuran (50 mL) and 1 M n-butyl lithium in hexanes (14.4 mL, 23.06 mmol) is added dropwise at −78° C. The solution is added via cannula to the aforementioned white slurry at −78° C. The reaction mixture is stirred at −78° C. for 15 minutes, then warmed to room temperature over 2.5 hours. The mixture is quenched with saturated aqueous sodium carbonate and the tetrahydrofuran is evaporated in vacuo. The remaining aqueous layer is diluted with water and extracted with ethyl acetate. The combined organic extracts are washed with brine, dried (Na$_2$SO$_4$), and the solvent is evaporated under vacuum. The product is purified by silica gel chromatography (75% to 50% hexane/ethyl acetate) to give 3-[2-(N-t-BOC-4-piperidinyl)-1-oxoethyl]-4(R)- (benzyl)-2-oxazolidinone.

To a solution of 3-[2-(N-t-BOC-4-piperidinyl)-1-oxoethyl]-4(R)-(benzyl)-2-oxazolidinone (7.54 g, 18.76 mmol) in tetrahydrofuran (175 mL) at −78° C. is added a 0.5 M solution of potassium bis (trimethylsilylamide in toluene (37.5 mL, 18.76 mmol) dropwise. After stirring for 20 minutes at −78° C., a pre-cooled solution of trisylazide (7.25 g, 23.4 mmol) in tetrahydrofuran (55 mL) is added via cannula at −78° C. The mixture is stirred for 15 minutes at −78° C., then acetic acid 3.38 g, 56.28 mmol) is added followed by immediate warming to room temperature through immersion in a water bath. The reaction mixture is stirred for 1.5 hours at room temperature. The tetrahydrofuran is removed under vacuum and the resulting residue is partitioned between saturated aqueous sodium carbonate and ethyl acetate. The aqueous layer is removed and extracted with ethyl acetate. The combined organic extracts are washed with brine, dried (Na$_2$SO$_4$), and concentrated in vacuo. The product is purified by silica gel chromatography (30% to 50% ethyl acetate/hexanes) to give 3-[2-(R)-azido-2-(N-t-BOC-4-piperidinyl)-1-oxo-ethyl]-4(R)-Coenzyl)-2-oxazolidinone.

To a solution of 3-[2-(R)-azido-2-(N-BOC-4-piperidinyl)-1-oxoethyl]-4(R)-(benzyl)-2-oxazolidinone (5.84 g, 13.17 mmol) in 3:1 tetrahydrofuran/water/200 mL) at 0° C. is added 30% aqueous hydrogen peroxide (5.12 mL, 52.67 mmol) followed by lithium hydroxide monohydrate (1.11 g, 26.34 mmol). The reaction mixture is stirred at 0° C. for 1 hour. The mixture is quenched by addition of sodium sulfite (7.1 g) at 0° C. The tetrahydrofuran is removed in vacuo and the remaining aqueous layer is further diluted with water. This aqueous layer is then washed with methylene chloride and acidified with 1N hydrochloric acid. The resulting acidic aqueous layer is extracted with ethyl acetate. The combined organic extracts are dried (Na$_2$SO$_4$) and concentrated in vacuo to provide crude 2-(R)-azido-2-(N-t-BOC-4-piperidinyl)acetic acid.

To a pre-stirred solution of tin (II) chloride (3.14 g, 16.55 mmol) in methanol (100 mL) at 0° C. is added 2-(R)-azido-2-(N-t-BOC-4-piperidinyl)acetic acid (2.35 g, 8.27 mmol) in methanol (25 mL) dropwise. The reaction mixture is stirred at 0° C. for 10 minutes then warmed to room temperature overnight. The methanol is removed in vacuo to provide crude R-(N-t-BOC-4-piperidinyl) glycine, which is used directly in the next reaction without purification. The crude product from the above reaction is dissolved in 2:1 dioxane/water (120 mL) and triethylamine (7.53 g, 74.43 mmol) and cooled to 0° C. To this mixture is added 4-methoxybenzenesulfonyl chloride (2.22 g, 10.75 mmol) and then the reaction mixture is warmed to room temperature overnight. The dioxane is removed in vacuo and the residue is partitioned between dilute aqueous sodium bicarbonate and ethyl acetate. The basic aqueous layer is removed, acidifed with 1N hydrochloric acid, and extracted with ethyl acetate. The resulting emulsion is passed through a celite pad washing with ethyl acetate. The organic filtrate is dried ($Na_2SO_4$) and concentrated in vacuo to provide 2(R)-[(4-methoxybenzenesulfonyl)amino]-2-(N-t-BOC-4-piperidinyl) acetic acid as crude product.

A solution of crude 2(R)-[(4-methoxybenzenesulfonyl) amino]-2-(N-t-BOC-4-piperidinyl)-acetic acid (2.88 g) in dimethylformamide (60 mL) containing N,N-dicyclohexylamine (1.22 g, 6.73 mmol) and benzyl bromide (1.15 g, 6.73 mmol) is stirred at room temperature for 3.5 hours. To this same reaction mixture is again added benzyl bromide (1.26 g, 7.4 mmol) followed by potassium carbonate (6.5 g, 47.11 mmol). The reaction mixture is stirred over the weekend at room temperature. The mixture is diluted with water and extracted with ethylacetate. The combined organic extracts are washed with brine, dried ($Na_2SO_4$), and concentrated in vacuo. The crude product is purified by silica gel chromatography (15% to 25% ethyl acetate/ hexanes) to provide benzyl 2(R)-[(4-methoxybenzenesulfonyl)(benzyl)-amino]-2-(N-t-BOC-4-piperidinyl)acetate.

A solution of benzyl 2(R)-[(4-methoxybenzenesulfonyl) (benzyl)amino]-2-(N-t-BOC-4-piperidinyl) acetate (2.0 g, 3.3 mmol) in dichloromethane (50 mL) is cooled to 0° C. and hydrochloric acid gas (from a lecture bottle) is bubbled through for 10 minutes. The reaction mixture is warmed to room temperature over 30 minutes. The solvent is removed in vacuo to yield benzyl 2(R)-[(4-methoxybenzenesulfonyl) (benzyl)-amino]-2-(N-t-BOC-4-piperidinyl) acetate hydrochloride as a white foam.

To a solution of benzyl 2(R)-[(4-methoxybenzene sulfonyl)(benzyl)amino]-2-(N-t-BOC-4-piperidinyl) acetate hydrochloride salt (1.28 g, 2.35 mmol) heated to reflux is added sodium formate (480.0 mg, 7.06 mmol) and formaldehyde (0.57 mL, 7.06 mmol). The reaction mixture is refluxed for 10 minutes, then two additional aliquots of formaldehyde (0.57 mL, 7.06 mmol) are added at 10 minute intervals. The reaction mixture is refluxed for an additional 3 hours. The formic acid is removed in vacuo and the residue is partioned between saturated aqueous sodium bicarbonate and ethyl acetate. The basic aqueous layer is further extracted with ethyl acetate. The combined organic extracts are washed with brine, dried ($Na_2SO_4$) and concentrated in vacuo to provide benzyl 2(R)-[(4-methoxybenzenesulfonyl) benzyl)amino]-2-(4-N-methylpiperidinyl) acetate as a crude product. A solution of this crude product (1.23 g) in 3N HCl (40 mL) is refluxed at 120° C. for 2 days. The mixture is concentrated in vacuo to provide acid as a crude product. To a solution of this crude product (1.08 g) in methylene chloride (75 mL) is added 1-hydroxybenzotriazole (0.312 g, 2.31 mmol), 4-methylmorpholine (1.64 g, 16.17 mmol), O-t-butylhydroxylamine hydrochloride (870.0 mg, 6.93 mmol), followed by N-[dimethylaminopropyl]-N'-ethylcarbodiimide hydrochloride (576.0 mg, 3.0 mmol). The reaction mixture is stirred at room temperature overnight. The reaction is then diluted with water and extracted with methylene chloride. The combined organic extracts are washed with brine, dried ($Na_2SO_4$), and the solvent is evaporated. The crude product is purified by silica gel chromatography (3% to 7% methanol/methylene chloride containing 0.5% ammonium hydroxide) to give N-(t-butyloxy)-2(R)-[(4-methoxybenzenesulfonyl)-(benzyl) amino]-2- (4- N -methylpipeddinyl) acetamide.

(b) Similarly prepared is N-hydroxy-2(R)-[(4-methoxybenzenesulfonyl)(benzyl)amino]-2-[N-(dimethylaminoacetyl)-4-piperidinyl]acetamide, m.p. 130°–150° C.;

The required intermediate is prepared as follows:

A solution of benzyl 2(R)-[(4-methoxybenzenesulfonyl) (benzyl)amino]2-(N-t-BOC-4-piperidinyl) acetate hydrochloride salt (0.96 g), in methylene chloride (25 ml) is cooled to 0° C. and HCl gas is bubbled through the solution for 30 minutes. The solution is evaporated to dryness to yield benzyl 2(R)-[(4-methoxybenzenesulfonyl)(benzyl)amino]-2-(4-piperidinyl) acetate hydrochloride.

To benzyl 2-(R)-[(4-methoxybenzenesulfonyl)(benzyl) amino]-2-(4-piperidinyl)acetate (0.866 g) in methylene chloride (50 ml) is added N,N-dimethylglycine (0.172 g), N-methylmorpholine (0.7 ml), 1-hydroxybenzotriazole (0.215 g) and 1-(3-dimethylaminopropyl)-3-ethylcarbodiimide (0.610 g). The mixture is stirred at room temperature over the weekend, diluted with water and extracted with methylene chloride. The combined organic extracts are dried over $Na_2SO_4$ and evaporated to dryness to yield benzyl 2(R)-[(4-methoxybenzenesulfonyl)(benzyl) amino]-2[(N-dimethylaminoacetyl)-4-piperidinyl]acetate.

A mixture of benzyl 2(R)-[(4-methoxybenzenesulfonyl) (benzyl)-amino]-2-[N-(dimethylaminoacetyl)-4-piperidinyl]acetate, ethanol (15 ml), 10% palladium on charcoal (0.106 g) and 1N hydrochloric acid (5.4 mL) is hydrogenated at 1 atmosphere pressure (for about 1 hour). The reaction mixture is filtered through celite, washed with water and ethanol, and evaporated to dryness to yield 2(R)-[(4-methoxybenzenesulfonyl)(benzyl)aminol-2-[N-dimethylaminoacetyl)-4-piperidinyl]acetic acid hydrochloride.

(c) Similarly prepared is N-hydroxy-2-(R)-[(4-methoxybenzenesulfonyl)(benzyl)amino]-2-(3-pyrrolidinyl)-acetamide hydrochloride, m.p. 160° C. dec.

(d) Similarly prepared is N-hydroxy-2(R)-[(4-methoxybenzenesulfonyl)(benzyl)amino]-2-(N-t-butoxycarbonyl-3-pyrrolidinyl)-acetamide, m.p. 120° C. dec., starting with N-t-butoxycarbonyl-3-pyrrolidineacetic acid.

(e) Similarly prepared is N-hydroxy-2(R)-[(4-methoxybenzenesulfonyl)(4-picolyl)amino]-2-(4-tetrahydropyranyl)-acetamide hydrochloride, m.p. >152° C. dec. starting with tetrahydropyranyl-4-acetic acid.

Example 33: Prepared similarly to the previous examples is N-hydroxy-2(R)-[(4-methoxybenzenesulfonyl)(3-picolyl) amino]-2(trans 4-hydroxycyclohexyl)-acetamide hydrochloride, m.p. 130°–155° C.

The starting material is prepared as follows:

D-4-hydroxyphenylglycine (10 g) is dissolved in 3N sodium hydroxide (20 ml). Water (180 ml) and then Raney nickel (27 g) are added. The reaction mixture is hydrogenated at about 3 atmospheric pressure and 50°–80° C. overnight.

The reaction mixture is filtered and reduced in volume to about 85 ml and dioxane (85 ml) is added. The solution of 4-hydroxycyclohexylglycine (see Coll. Czech. Chem. Comm. 49, 712–742 (1984)) is cooled to 0° C. and treated with triethylamine (11.37 ml) and 4-methoxybenzenesulfonyl chloride (10.95 g). The reaction mixture is allowed to warm to room temperature and stirred over the weekend. The dioxane is removed in vacuo and the remaining aqueous solution is diluted with 1N hydrochloride acid. The resulting precipitate is collected, washed with water and ether to yield (R)-N-(4-methoxybenzenesulfonyl)-4-hydroxycyclohexylglycine which is converted to the methyl ester with methanol in the presence of thionyl chloride. To a solution of (R)-N-(4-methoxybenzenesulfonyl)-4-hydroxycyclohexylglycine methyl ester (0.859 g) in methylene chloride (8 ml) are added acetic arthydride (2.26 ml) and pyridine (3.90 ml). The reaction mixture is stirred at room temperature overnight, quenched with methanol, washed with 1N hydrochloric acid and extracted with methylene chloride. The methylene chloride extract is dried over sodium sulfate and evaporated to dryness to yield (R)-N-(4-methoxybenzenesulfonyl)-4-acetyloxycyclohexylglycine methyl ester. Heating with 3 NHCl at reflux for 24 hours yields (R)-N-(4-methoxybenzenesulfonyl)-4-hydroxycyclohexylglycine.

Example 34: Prepared similarly to the previous examples are (a) N-hydroxy-2(R)-[(4-methoxybenzenesulfonyl)(benzyl)amino]-2-(trans-4-dimethylaminocyclohexyl)acetamide hydrochloride, m.p. 138°–146° C.

The starting material is prepared as follows:

A solution of oxalyl chloride (1.25 g) in methylene chloride (30 ml) is cooled to −78° C. and dimethylsulfoxide (1.16 ml) is slowly added. The reaction mixture is stirred at −78° C. for about 30 minutes and a solution of (R)-N-(4-methoxybenzenesulfonyl)-4-hydroxycyclohexyglycine methyl ester (2.34 g) in methylene chloride (30 ml) is added dropwise. Stirring is continued for 30 minutes at −78° C. and then at 0° C. for 30 minutes. The reaction mixture is again cooled to −78° C., triethylamine (7.3 ml) is added dropwise, and the reaction mixture is stirred at −78° C. for 30 minutes, allowed to warm to room temperature over an hour, diluted with methylene chloride, washed rust with 1N hydrochloric acid and then brine. The organic layer is dried over sodium sulfate, evaporated to dryness, and the resulting product is purified by flash chromatography using 50–60% ethyl acetate in hexane to yield (R)-N-(4-methoxybenzenesulfonyl)-4-oxocyclohexylglycine methyl ester as a white solid. Treatment with benzyl bromide in DMF in the presence of potassium carbonate at room temperature yields (R)-N-(4-methoxybenzenesulfonyl)-N-benzyl-4-oxocyclohexylglycine methyl ester as an oil. The ketone (2.2 g) is dissolved in methylene chloride (3 ml) and isopropanol (60 ml). Molecular sieves (3A°, 1.5 g), sodium cyanoborohydride (0.311 g), and ammonium acetate (3.81 g) are added. The reaction mixture is stirred at room temperature overnight, filtered and evaporated to dryness. The residue is partitioned between water and methylene chloride and the product extracted with methylene chloride. The resulting product is purified by flash chromatography using methanol/methylene chloride/0.5% ammonium hydroxide as eluent to yield (R)-N-(4-methoxybenzenesulfonyl)-N-benzyl-4-aminocyclohexylglycine methyl ester. N-Methylation with formic acid/formaldehyde/sodium formate at reflux temperature followed by hydrolysis with 3N hydrochloric acid at reflux temperature yields 2-(R)-[(4-methoxybenzenesulfonyl)(benzyl)amino]-2-(trans-4-dimethylaminocyclohexyl)acetic acid.

(b) N-hydroxy-2(R)-[(4-methoxybenzenesulfonyl)(benzyl)amino]-2-[trans-4-(dimethylaminoacetylamino)cyclohexyl]acetamide hydrochloride, m.p. 163°–170° C., obtained from (R)-N-(4-methoxybenzenesulfonyl)-N-benzyl-4-aminocyclohexylglycine benzyl ester, which is in turn prepared from (R)-N-(4-methoxybenzenesulfonyl)-4-hydroxycyclohexyl-glycine benzyl ester.

Example 35: A solution of N-benzyloxy-2(R)-[(4-methoxybenzenesulfonyl)(benzyl)amino]-3-hydroxy-4-methylpentanamide (125 mg) in ethanol (100 ml) is hydrogenated in the presence of 5% palladium on charcoal (100 mg) at room temperature and atmospheric pressure to yield N-hydroxy-2(R)-[(4-methoxybenzenesulfonyl)(benzyl)amino]-3-hydroxy-4-methyl-pentanamide, m.p. 81°–82° C.

The starting material is prepared as follows:

(R)-3-hydroxy-4-methyl-2-amino pentanoic acid methyl ester, prepared according to methodology described by Evans in Tetrahedron Letters 28, 39 (1987) and J. Am. Chem. Soc. 109, 7151 (1981) from isobutyraldehyde, is converted, according to methodology in previous examples, to 2(R)-[(4-methoxybenzenesulfonyl)(benzyl)amino]3-hydroxy-4-methylpentanoic acid.

A solution of 2(R)-[(4-methoxybenzenesulfonyl)(benzyl)amino]3-hydroxy-4-methylpentanoic acid (1.4 g) in methylene chloride (3.5 ml) is treated with 2,6-lutidine (1.21 ml) and tert-butyl-dimethylsilyltrifluoromethanesulfonate (2.03 ml) at 0° C. The solution is stirred at 0° C. for 4 hours, then at room temperature for 2 hours, poured into sodium bicarbonate solution (10.0 ml) and extracted with ether. The resulting product is purified by column chromatography on silica gel using gradients of ethyl acetate/hexane as eluent to obtain 2(R)-[(4-methoxybenzenesulfonyl)(benzyl)amino]3-(tert-butyl-dimethylsilyloxy)-4-methylpentanoic acid tert-butyl-dimethylsilyl ester. Treatment of the ester (1.2 g) with potassium carbonate (285 mg) in THF water (1:1) for 30 minutes at 0° under nitrogen, acidification and extraction with ethyl acetate yields 2(R)-[(4-methoxybenzenesulfonyl)(benzyl)amino]3-(tert-butyl-dimethylsilyloxy)-4-methylpentanoic acid.

To a solution of 2(R)-[(4-methoxybenzenesulfonyl)(benzyl)amino]-3-(tert-butyldimethylsilyloxy)-4-methylpentanoic acid (0.5 g) in methylene chloride (10 ml) are added O-benzylhydroxylamine hydrochloride (0.154 g), 1-hydroxy-pyridobenzotriazole (HOPT, 0.131 g), N-methylmorpholine (0.371 ml) at room temperature. Then 1-(3-dimethylaminopropyl)-3-ethyl-carbodiimide (0.370 g) is added at 0° C. and the reaction mixture is stirred at room temperature overnight under nitrogen. The reaction mixture is diluted with ethyl acetate and water, and the ethyl acetate extract is washed with 1N hydrochloric acid, sodium bicarbonate solution, water and brine. The organic phase is dried, evaporated to dryness and the resulting product is purified by flash chromatography using ethyl acetate/hexane gradients as eluent to yield N-benzyloxy-2(R)-[(4-methoxybenzenesulfonyl)(benzyl)amino]-3-ten-butyl-dimethylsilyloxy) 4-methylpentanamide.

A solution of the above (0.4 g) in acetonitrile (6.4 ml) is treated with 48% hydrogen fluoride (0.25 ml) and stirred at room temperature for 4 hours. Workup in the usual manner and purification by chromatography on silica gel with ethyl acetate/hexane gradients as eluent yields N-benzyloxy-2(R)-[(4-methoxybenzenesulfonyl)(benzyl)amino]-3-hydroxy-4-methylpentanamide as an oil.

Similarly prepared are (a) N-hydroxy-2(R)-[(4-methoxybenzenesulfonyl)(n-propyl)amino]-3-hydroxypentanamide, m.p. 129°–131 ° C.;

(b) N-hydroxy-2(R)-[(4-methoxybenzenesulfonyl)(n-propyl)-amino]3-hydroxy-4-methylpentanamide, m.p. 69°–71° C.;

(c) N-hydroxy-2(R)-[(4-methoxybenzenesulfonyl)(benzyl)amino]-3-hydroxy-4-methypentanamide, m.p. 81°–82° C.;

(d) N-hydroxy-2(R)-[(4-methoxybenzenesulfonyl)(n-propyl)amino]-3-hydroxyoctanamide, m.p. 123°–125° C.;

(e) N-hydroxy-2(R)-[(4-methoxybenzenesulfonyl)(n-propyl)amino]-3-hydroxy-5-methylhexanamide, m.p. 97°–99° C.

Example 36: Similarly prepared to the previous examples are:

(a) N-hydroxy-2(R)-[(3-fluoro-4-methoxybenzenesulfonyl)(3-picolyl)amino]-3-methylbutanamide hydrochloride, $[\alpha]_D^{25}$+33.85 (c 10.39 mg/ml, CH$_3$OH);

(b) N-hydroxy-2(R)-[(4-methoxybenzenesulfonyl)(4-picolyl)amino]-2-(2-tetrahydrofuranyl) acetamide, m.p. 89°–92° C., $[\alpha]_D^{25}$+4.82 (c 8, CH$_3$OH).

The starting material, R-(2-tetrahydrofuranyl)-glycine, is prepared according to J. Am. Chem. Soc. 110, 1547 (1988).

(c) N-hydroxy-2(R)-[(4-methoxybenzenesulfonyl)(3-picolyl)amino]-2-(2-tetrahydrofuranyl)-acetamide, m.p. 91°–93° C., $[\alpha]_D^{25}$+0.62 (c 7.0, CH$_3$OH);

(d) N-hydroxy-2(R)-[(4-methoxybenzenesulfonyl)(benzyl)amino]-2-(2-tetrahydrofuranyl)-acetamide, m.p. 143°–144° C.; $[\alpha]_D^{25}$+1.03 (c 6.4, CH$_3$OH);

(e) N-hydroxy-2(S)-[(4-methoxybenzenesulfonyl)(3-picolyl)amino]-2-(2-tetrahydrofuranyl)-acetamide, m.p. 162°–163° C.; $[\alpha]_D^{25}$=4.22 (c 6.5, CH$_3$OH);

(f) N-hydroxy-2(R)-[(4-methoxybenzenesulfonyl)(4-picolyl)amino]-2-cyclopentylacetamide hydrochloride, m.p. >140° dec.; $[\alpha]_D^{25}$+27.9 (c 9.4, CH$_3$OH);

(g) N-hydroxy-2(R)-[(4-methoxybenzenesulfonyl)(benzyl)amino]-2-(trans-4-hydroxy-2-tetrahydrofuranyl) acetamide, m.p. 53°–56° C., as a mixture of diastereoisomers; the starting material, trans-(4-hydroxy-2-tetrahydrofuranyl)glycine is prepared according to J. Am. Chem. Soc. 110, 4533 (1988);

(h) N-hydroxy-2(R)-[(4-methoxybenzenesulfonyl)(benzyl)amino]-2-(4-oxacyclooctyl)acetamide, m.p. 152°–157° C., as a mixture of diastereoisomers;

(i) N-hydroxy-2(R)-[(4-methoxybenzenesulfonyl)(4-picolyl)-amino]-2-(4-oxacycloheptyl)acetamide hydrochloride, m.p. 130°–145° C., as a mixture of diastereoisomers;

(j) N-hydroxy-2(R)-[(4-methoxybenzenesulfonyl)(4-picolyl)amino]-2-cyclooctylacetamide hydrochloride, m.p. 124°–140° C.;

(k) N-hydroxy-2(R)-[(4-methoxybenzenesulfonyl)(4-picolyl)amino]-2-(2-oxohexahydroazepin-5-yl)acetamide hydrochloride, diastereoisomer A, m.p. 160°–172° C. dec.

(l) N-hydroxy-2(R)-[(4-methoxybenzenesulfonyl)(4-picolyl)amino]-2-(2-oxohexahydroazepin-5-yl)acetamide hydrochloride, diastereoisomer B, m.p. 155°–170° C.;

(m) N-hydroxy-2(R)-[(4-methoxybenzenesulfonyl)(benzyl)amino]-2-(2-oxohexahydroazeopin-5-yl)acetamide, diastereoisomer A, m.p. 115°–130° C.;

(n) N-hydroxy-2(R)-[(4-methoxybenzenesulfonyl)(benzyl)amino]-2-(2-oxohexahydroazepin-5-yl)acetamide, diastereoisomer B, m.p. 120°–140° C.;

(o) N-hydroxy-2(R)-[(4-methoxybenzenesulfonyl)(n-propyl)amino]-3,4-dimethoxybutanamide, m.p. 53°–55° C.;

(p) N-hydroxy-2(R)-[(4-methoxybenzenesulfonyl)(n-propyl)amino]-3-methoxy-3-(N-tert-butoxycarbonyl-4-piperidyl)propionamide, m.p. 102°–103° C.;

(q) N-hydroxy-4-[(4-methoxybenzenesulfonyl)(benzyl)amino]-N-(methoxycarbonyl-methyl)-piperidine-4-carboxamide hydrochloride, m.p. 183.5°–185° C.;

(r) N-benzyloxy-4-[(4-methoxybenzenesulfonyl)(n-benzyl)amino]-N-(methoxy-carbonylmethyl)-piperidine-4-carboxamide, m.p. 52.5°–55° C.;

(s) N-hydroxy-2-[[4-methoxybenzensulfonyl](benzyl)amino]-2-[2-thienylthio)methyl]acetamide by starting the synthesis with β-(2-thienylthio)alanine (prepared according to the procedure of J. Am. Chem. Soc. 110, 2237, (1988);

(t) N-hydroxy-2-[[4-methoxybenzenesulfonyl](benzyl)amino]-2-[(2-furanylthio)methyl]-acetamide by starting the synthesis with β-(2-furanylthio)alanine (prepared according to the procedure of J. Am. Chem. Soc. 110, 2237 (1988);

(u) N-hydroxy-2-[[4-methoxybenzenesulfonyl](benzyl)amino]-2-[(phenylthio)methyl]-acetamide by starting the synthesis with β-(phenylthio)alanine (prepared according to the procedure of J. Am. Chem. Soc. 110, 2237 (1988);

(v) N-hydroxy-2(R)-[(4-methoxybenzenesulfonyl)(4-picolyl)amino]-2-(N-ethoxycarbonyl-4-piperidyl)-acetamide hydrochloride, m.p. 145°–158° dec.; $[\alpha]_D$+19.83 (c=5.56 mg/ml, CH$_3$OH);

(w) N-hydroxy-2-[(4-methoxybenzenesulfonyl)(4-picolyl)amino]-2-(tetrahydro-2H-pyran-2-yl)-acetamide hydrochloride, m.p. 169°–170° dec.;

(x) N-hydroxy-2(R)-[(4-methoxybenzenesulfonyl)(4-picolyl)amino]-2-(cis-4-hydroxycyclohexyl)-acetamide hydrochloride, m.p. 175°–180°; $[\alpha]_D^{25}$+14.04 (c 6.37 mg/ml, CH$_3$OH);

(y) N-hydroxy-2(R)-[(4-methoxybenzenesulfonyl)(benzyl)amino]-2-[trans-4-(ethoxycarbonylamino)cyclohexyl]acetamide, m.p. 105°–115°.

Example 37: Preparation of 3000 capsules each containing 25 mg of the active ingredient, for example, N-hydroxy-2(R)-[[4-methoxybenzenesulfonyl](3-picolyl)amino]-3-methylbutanamide hydrochloride:

| Active ingredient | 75.00 g |
|---|---|
| Lactose | 750.00 g |
| Avicel PH 102 (microcrystalline cellulose) | 300.00 g |
| Polyplasdone XL (polyvinylpyrrolidone) | 30.00 g |
| Purified water | q.s. |
| Magnesium stearate | 9.00 g |

The active ingredient is passed through a No. 30 hand screen.

The active ingredient, lactose, Avicel PH 102 and Polyplasdone XL are blended for 15 minutes in a mixer. The blend is granulated with sufficient water (about 500 mL), dried in an oven at 35° C. overnight, and passed through a No. 20 screen.

Magnesium stearate is passed through a No. 20 screen, added to the granulation mixture, and the mixture is blended for 5 minutes in a mixer. The blend is encapsulated in No. 0 hard gelatin capsules each containing an amount of the blend equivalent to 25 mg of the active ingredient.

What is claimed is:

1. A method treating tumors selected from human breast carcinoma, lung carcinoma, bladder carcinoma, colon carcinoma, prostate carcinoma, skin carcinoma and ovarian carcinoma which comprises administering to a subject in need thereof a therapeutically effective amount of N-hydroxy-2(R)-[(4-methoxybenzenesulfonyl)(3-picolyl)amino]-3-methylbutanamide or a pharmaceutically acceptable salt thereof.

2. A method according to claim 1 for the treatment of lung carcinoma.

3. A method according to claim 1 for the treatment of bladder carcinoma.

4. A method according to claim 1 for the treatment of prostate carcinoma.

5. A method according to claim 1 for the treatment of colon carcinoma.

6. A method according to claim 1 for the treatment of skin carcinoma.

7. A method according to claim 1 for the treatment of breast carcinoma.

8. A method according to claim 1 for the treatment of ovarian carcinoma.

9. A method according to claim 1 wherein the compound is N-hydroxy-2(R)-[(4-methoxybenzenesulfonyl)(3-picolyl) amino]-3-methylbutanamide hydrochloride.

10. A method according to claim 2 wherein the compound is N-hydroxy-2(R)-[(4-methoxybenzenesulfonyl)(3-picolyl) amino]-3-methylbutanamide hydrochloride.

11. A method according to claim 3 wherein the compound is N-hydroxy-2(R)-[(4-methoxybenzenesulfonyl)(3-picolyl) amino]-3-methylbutanamide hydrochloride.

12. A method according to claim 4 wherein the compound is N-hydroxy-2(R)-[(4-methoxybenzenesulfonyl)(3-picolyl) amino]-3-methylbutanamide hydrochloride.

13. A method according to claim 5 wherein the compound is N-hydroxy-2(R)-[(4-methoxybenzenesulfonyl)(3-picolyl) amino]-3-methylbutanamide hydrochloride.

14. A method according to claim 6 wherein the compound is N-hydroxy-2(R)-[(4-methoxybenzenesulfonyl)(3-picolyl) amino]-3-methylbutanamide hydrochloride.

15. A method according to claim 7 wherein the compound is N-hydroxy-2(R)-[(4-methoxybenzenesulfonyl)(3-picolyl) amino]-3-methylbutanamide hydrochloride.

16. A method according to claim 8 wherein the compound is N-hydroxy-2(R)-[(4-methoxybenzenesulfonyl)(3-picolyl) amino]-3-methylbutanamide hydrochloride.

* * * * *